(12) United States Patent
Umeda et al.

(10) Patent No.: US 7,553,837 B2
(45) Date of Patent: Jun. 30, 2009

(54) PHENYLAZOLE COMPOUNDS PRODUCTION PROCESS AND ANTIOXIDANTS

(75) Inventors: Nobuhiro Umeda, Odawara (JP); Nobuo Mochizuki, Odawara (JP); Seiichi Uchida, Odawara (JP); Mitsumasa Takada, Odawara (JP); Seiichi Ikeyama, Odawara (JP); Shiro Tsubokura, Odawara (JP); Yasuyuki Shiinoki, Odawara (JP); Fumie Shirato, Odawara (JP); Hiroko Momoe, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 285 days.

(21) Appl. No.: 10/566,820

(22) PCT Filed: Jul. 30, 2004

(86) PCT No.: PCT/JP2004/011297

§ 371 (c)(1),
(2), (4) Date: Jan. 30, 2006

(87) PCT Pub. No.: WO2005/012293

PCT Pub. Date: Feb. 10, 2005

(65) Prior Publication Data

US 2006/0247228 A1 Nov. 2, 2006

(30) Foreign Application Priority Data

| Aug. 1, 2003 | (JP) | 2003-285421 |
| Aug. 11, 2003 | (JP) | 2003-291881 |
| Aug. 22, 2003 | (JP) | 2003-298443 |
| Jan. 30, 2004 | (JP) | 2004-022958 |
| Jan. 30, 2004 | (JP) | 2004-023903 |
| Jan. 30, 2004 | (JP) | 2004-023971 |

(51) Int. Cl.
*A61K 31/497* (2006.01)
*A61K 31/445* (2006.01)
*A01N 43/40* (2006.01)
*C07D 241/04* (2006.01)
*C07D 295/00* (2006.01)
*C07D 211/00* (2006.01)

(52) U.S. Cl. .................. 514/252.12; 514/315; 544/358; 546/184

(58) Field of Classification Search ................ None
See application file for complete search history.

(56) References Cited

U.S. PATENT DOCUMENTS 4,006,243 A 2/1977 Strehlke et al.

(Continued)

FOREIGN PATENT DOCUMENTS

DE 3407505 A1 9/1985

(Continued)

OTHER PUBLICATIONS

Warner. Expert Opinion in Therapeutic Patents, 2000, 10(2), 245-49.*
Martignoni et al. Expert Opinion in Drug Metabolism and Toxicology, 2006, 2(6), 875-94.*

(Continued)

*Primary Examiner*—James O Wilson
*Assistant Examiner*—Noble Jarrell
(74) *Attorney, Agent, or Firm*—Darby & Darby P.C.

(57) ABSTRACT

The present invention is directed to compounds represented by the formula (1): B-D-Z (1), wherein B represent the following formula (B-1), (B-2) or (B-3);

A represents an optionally substituted imidazole or pyrazole group;
E represents the following formula (1a);

X represents an oxygen atom, the formula: SOu, or the formula: N—$R_9$;
Y represents a carbon atom or a nitrogen atom;
D represents an oxygen atom, a sulfur atom or the formula (1a);
Z represents (a chroman-2-yl group, a chroman-4-yl group, a 2,3-dihydrobenzofuran-2-yl group, a 2,3-dihydrobenzofuran-3-yl group, etc.) which is substituted with $NHR_{10}$ or $OR_{11}$)] or pharmaceutically acceptable salts thereof, and to antioxidants, therapeutic agents for kidney diseases or cerebrovascular disorder, and retinal oxidative damage inhibitors, which include the compounds as the active ingredient.

3 Claims, No Drawings

U.S. PATENT DOCUMENTS

| | | | |
|---|---|---|---|
| 4,301,169 | A | 11/1981 | Yamanaka et al. |
| 5,376,681 | A | 12/1994 | Aono et al. |
| 5,393,775 | A | 2/1995 | Le Baut et al. |
| 5,552,552 | A | 9/1996 | Ohkawa et al. |
| 5,859,181 | A | 1/1999 | Zhao et al. |

FOREIGN PATENT DOCUMENTS

| | | | |
|---|---|---|---|
| EP | 1101759 | A1 | 5/2001 |
| FR | 2267101 | | 4/1975 |
| JP | 55-69567 | A | 5/1980 |
| JP | 2-121975 | A | 5/1990 |
| JP | 5-140142 | A | 6/1993 |
| JP | 6-192248 | A | 7/1994 |
| JP | 6-228136 | A | 8/1994 |
| JP | 9-176157 | A | 7/1997 |
| WO | WO-87/05020 | A1 | 8/1987 |
| WO | WO-95/29163 | A1 | 11/1995 |
| WO | WO-96/28437 | A1 | 9/1996 |
| WO | WO9957113 | * | 11/1999 |
| WO | WO-00/06550 | A1 | 2/2000 |

OTHER PUBLICATIONS

"Neuroleptic Activity in 5-Aryltetrapydro-γ-carbolines" by Harbert et al., Journal of Medicinal Chemistry, Jun. 1980, vol. 23, No. 6, pp. 635-643.

"Pyridine Hydrochloride-Catalyzed Fischer Indole Reactions" by Welch, Synthesis—International Journal of Methods in Synthetic Organic Chemistry, Sep. 1977, No. 9, pp. 645-646.

"Synthesis of Some Conformationally Restricted Analogues of Fentanyl[1]", by Berger et al., Journal of Medicinal Chemistry, vol. 20, Apr. 1977, No. 4, pp. 600-602.

"Lipid Peroxidation in Liver: Hydroxy Dimethyl Carbazole, A New Potent Inhibitor" by Malvy, et al., Biochemical and Biophysical Research Communications, vol. 95, No. 2, Jul. 31, 1980, pp. 734-737.

"5-Aminocoumarans: Dual Inhibitors of Lipid Peroxidation and Dopamine Release with Protective Effects against Central Nervous System Trauma and Ischemia" by Ohkawa et al., Journal of Medicinal Chemistry, Feb. 14, 1997, vol. 40, No. 4, American Chemical Society, pp. 559-573.

Measurement of Thiobarbituric acid Value in Liver Homogenate Solubilized with Sodium dodecylsulphate and Variation of the Values Affected by Vitamin E and Drugs by Masugi et al., Vitamins (Japan) 51, 1977, pp. 21-29.

"Cleavage of Structural Proteins during the Assembly of the Head of Bacteriophage T4" by Laemmli, Nature, vol. 227, Aug. 15, 1970, pp. 680-685.

"5-Lipoxygenase Inhibitory Activity of Zileuton1" by Carter et al., The Journal of Pharmacology and Experimental Therapeutics, vol. 256, No. 3, Mar. 1991, pp. 929-937.

"A Spectrophotometric Microtiter-Based Assay for the Detection of Hydroperozy Derivatives of Linoleic Acid" by Auerbach, et al., Analytical Biochemistry, vol. 201, No. 2, Mar. 1992, pp. 375-380.

International Search Report for PCT/JP2004/011297 mailed Sep. 21, 2004.

* cited by examiner

PHENYLAZOLE COMPOUNDS PRODUCTION PROCESS AND ANTIOXIDANTS

CROSS-REFERENCE TO PRIOR APPLICATION

This is a U.S. National Phase Application under 35 U.S.C. §371 of International Patent Application No. PCT/JP2004/011297 filed Jul. 30, 2004, and claims the benefit of Japanese Patent Application Nos. 2003-285421 filed Aug. 1, 2003, 2003-291881 filed Aug. 11, 2003, 2003-298443 filed Aug. 22, 2003, 2004-022958 filed Jan. 30, 2004, 2004-023903 filed Jan. 30, 2004 and 2004-023971 filed Jan. 30, 2004, all of which are incorporated by reference herein. The International Application was published in Japanese on Feb. 10, 2005 as WO 2005/012293 A1 under PCT Article 21(2).

TECHNICAL FIELD

The present invention relates to novel phenylazole compounds, a production process thereof, antioxidants containing the compounds as an active ingredient, and retinal oxidative damage inhibitors, lipoxygenase inhibitors, 20-HETE production inhibitors, and therapeutic agents for kidney diseases, cerebrovascular or circulatory diseases and cerebral infarction using the antioxidants.

BACKGROUND ART

It has recently become apparent that the production of lipid peroxidation in the living body and the radical reaction accompanying the production of lipid peroxidation exert various adverse influences on the living body via membrane damage and cell damage. Therefore, it has been made various attempts of applying antioxidants and lipid peroxidation production inhibitors to drugs, and various kinds of studies on antioxidants have been made. As the antioxidants, for example, pharmaceutical compositions containing a specific quinone derivative used for treatment and prophylaxis of endotoxin shock ascribable to inflammation or infection; hydroxamic acid derivatives having a cell proliferation inhibitory action and a neovascularization inhibitory action used for treatment and prophylaxis of autoimmune diseases; and 2,3-dihydrobenzofuran derivatives which are useful as antioxidizing agents and radical scavengers (for example, Patent Document 1) are known. Also, imidazole-based compounds having an anti-hyperlipidemia action, which are useful for treatment and prophylaxis of arteriosclerosis (for example, Patent Document 2); and benzothiazinecarboxamide which has an anti-arthritis activity and is represented by the following formula (for example, Patent Document 3) are known.

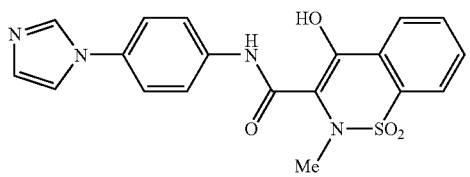

Furthermore, there are carbonylaminophenylimidazole derivatives (refer to Patent Document 4); aminodihydrobenzofuran derivatives having a lipid peroxidation production inhibitory action which is useful as a preventive or therapeutic agent for various diseases such as arteriosclerosis, hepatopathy and cerebrovascular disorder (Patent Document 5); antihyperlipidemic agents containing a phenylazole compound (Patent Document 6); dihydrobenzofuran derivatives which significantly ameliorate damage on lipid, protein, carbohydrate and DNA caused as a result of oxidative stress which arises when an antioxidative defense system is insufficient (Patent Document 7); and optically active aminodihydrobenzofuran derivatives which are useful for amelioration, treatment and prophylaxis of brain functional disorder accompanying rebral apoplexy and head injury (Patent Document 8).

Regardless of large energy need, since supply of energy depends on blood circulation, brain is drastically weak against ischemia. When cerebral blood flow stops by various reasons, resulting in cerebral ischemia, active oxygen species are generated due to mitochondria disorder and an increase in calcium content in nerve cells. Also it is known that oxygen radicals are explosively generated on reopening of blood stream after ischemia. It is considered that these active oxygen species finally exerts an action on lipid, protein and nucleic acid and oxidize them, thereby causing cell death. Antioxidants are used for treatment of these disease states, and edaravone is permitted as a brain protective agent and used in Japan.

As lipoxygenase (LO) which causes the addition of oxygen to an unsaturated fatty acid typified by arachidonic acid, for example, 5-LO, 8-LO, 12-LO and 15-LO are known according to the site to which oxygen is added. Among these, 5-LO is a primary enzyme which synthesizes leukotriene as a strong inflammation mediator. Lukotrienes is involved in various inflammatory diseases such as asthma, rheumatic arthritis, inflammatory colitis and psoriasis and control thereof is useful for treatment of these diseases. It is known that 12-LO and 15-LO react with linoleic acid, cholesterol ester, phospholipids and low density lipoprotein (LDL), in addition to arachidonic acid, and causes the addition of oxygen to the unsaturated fatty acid. It is known that macrophage infinitely incorporate oxidation-modified LDL via a scavenger receptor to form foam cells, which is a first step of formation of arteriosclerotic focus It is also apparent that 12-LO and 15-LO are expressed in a high level in the macrophage and is essential as a trigger of oxidative modification of LDL. Control of them is useful for treatment of various diseases caused by arteriosclerosis.

When arachidonic acid as a precursor of fatty acid is separated from phospholipids of a cellular membrane, it is converted into 20-HETE by a 20-hydroxyeicosatetraenoic acid (HETE) synthase. It is known that 20-HETE contracts or extends microvasculature or causes cell proliferation in main organs such as kidney and brain blood vessel. It is suggested that it is involved in an important physiological effect in the living body and has a close relation with disease states of kidney diseases, cerebrovascular diseases and circulatory diseases. Furthermore, it is reported that a phenylazole derivative has an inhibitory action of the 20-HETE synthase.

It is considered that, regarding most ophthalmic diseases which are frequently caused by aging such as cataract or macular degeneration, oxidative stress involved in free radicals and active oxygen is one of onset factors. It is known that the retina is a tissue which is likely to be influenced by aging, together with crystalline lens. The retina is likely to be influenced by various free radicals because it contains a large amount of a higher unsaturated fatty acid and a nutrient is supplied from both retinal vessel and choriocapillaries, and also consumes a large amount of oxygen. For example, light such as sunlight supplied throughout one's life is a typical one of oxidative stress to the retina. Visible light and infrared light account for almost all of sunlight which arrives at the ground, and several percents of ultraviolet light contained therein strongly interacts with the living body as compared with visible light and infrared light and thus it drastically exerts an adverse influence on health. Ultraviolet light is classified into UV-A (320 to 400 nm), UV-B (280 to 320 nm) and UV-C (190 to 280 nm) according to a difference in wavelength, and the action and intensity to the living body vary. It has been considered that ultraviolet light having a wavelength of 290 nm or less having particularly strong cytotoxicity is absorbed by the ozone layer of stratosphere and hardly arrives at the ground. However, it is considered that the appearance of ozone hole, which is considered to be caused by environmental disruption, recently increases the dose of ultraviolet light which arrives at the earth and also dermatopathy and cutaneous cancer involved in ultraviolet light increase in the south hemisphere, and thus retinopathy may significantly increase by the influence of UV-A which arrives at the retina.

Age-related macular degeneration among ophthalmic diseases is retinopathy which may frequently cause ablepsia, and it is considered that ten million people develop slight symptoms and 450,000 or more are suffering from visual deficit caused by this disease in the States. Also in Japan in which the aging society has already been established rapidly, there is a fear of an increase in this disease. A mechanism of the onset of macular degeneration is unclear. However, it is considered that progression of this lesion is involved in the peroxidation reaction due to light absorption at the retina. Also it is considered that the appearance of a lipofuscin-like fluorescent material referred to as drusen is recognized at the prophase of the onset and also lipofuscin is produced by bonding an aldehyde as a secondary decomposition product of lipid peroxidation with a protein, and thus the lipid peroxidation reaction due to ultraviolet light or visible light at the retina can induce this retinopathy.

A therapeutic agent for retinal diseases containing a specific dihydrofuran derivative, which is useful for prophylaxis and treatment of retinal diseases due to an antioxidation action, and an agent for change in visual acuity and retina, including macular degeneration of the retina, which contains propionyl L-carnitine or pharmaceutically acceptable salts thereof and carotenoid, are known.

Patent Document 1: Japanese Unexamined Patent Application, First Publication No. Hei 2-121975
Patent Document 2: Pamphlet of International Publication No. 95/29163
Patent Document 3: Specification of German Patent Publication DE 3,407,505
Patent Document 4: Japanese Unexamined Patent Application, First Publication No. Sho 55-69567
Patent Document 5: Japanese Unexamined Patent Application, First Publication No. Hei 5-140142
Patent Document 6: Pamphlet of International Publication No. WO00/006550
Patent Document 7: Pamphlet of International Publication No. WO96/28437
Patent Document 8: Japanese Unexamined Patent Application, First Publication No. Hei 6-228136

DISCLOSURE OF THE INVENTION

An object of the present invention is to provide antioxidants which are useful for treatment of ischemic organopathies such as arteriosclerosis, myocardial infarction and cerebral infarction, or treatment of diseases such as kidney diseases due to oxidative cell damage, and to provide retinal oxidative damage inhibitors which inhibit retinopathy due to oxidation, particularly photooxidation, lipoxygenase inhibitors, 20-HETE synthase inhibitors, therapeutic agents for kidney diseases, cerebrovascular or circulatory diseases and cerebral infarction.

The inventors of the present invention have intensively studied so as to achieve the object described above and found that a conventional antioxidant has insufficient potency because the agent does not arrive at the target site or activity is lost before it arrives at the target site, and also they have intensively studied for the purpose of developing an antioxidant which is more excellent in organ migration properties and easily passes a blood brain barrier or a blood retina barrier. Consequently, compounds represented by the formula (1) have attained the expected object. Furthermore, they have found that the compounds have excellent in vivo antioxidation action regardless of an administration path, and the present invention has been completed.

Furthermore, the inventors of the present invention have studied about an influence on the retina by irradiating rat eyes with UV-A at a fixed dose. At the prophase of the onset of retinal diseases such as macular degeneration, which may frequently cause ablepsia, a lipofuscin-like fluorescent material from a product of the reaction of a lipid peroxidation-derived aldehyde and protein is frequently detected. An increase in protein of the protein at about 66 kDa, which is well proportional to a change in retinal tissue of eyes irradiated with UV-A, is recognized and instrumental analysis and the results of study using albumine-free rat reveal that this protein is an albumin-like substance. In vitro autoxidation reaction of the retinal tissue, a significant increase in the lipofuscin-like fluorescent material is recognized by allowing albumin to coexist. Therefore, an abnormal increase in a partial protein in the retinal tissue as a result of irradiation with UV-A has a relation with an increase in the fluorescent material at the retina, and may cause retinopathy. Heretofore, the inventors of the present invention have studied about retinopathy inhibitors considering a change in a retinal protein as a first biochemical indicator. It has been found that, in the process, the compounds having a strong antioxidation ability of the present invention are migrated to the retina within a short time by oral administration and thus remarkably inhibit an increase in 66 kDa protein due to spot irradiation with UV-A. Consequently, it has been found that the compounds of the present invention are effective to retinopathy due to oxidation and are particularly effective to relieve progression and symptoms of age-related macular degeneration of the retina which increases with aging. The present invention has been completed based on this finding.

First, the present invention is directed to a compound represented by the formula (1):

B-D-Z                                                 (1)

[wherein B represents the following formula (B-1), (B-2) or (B-3):

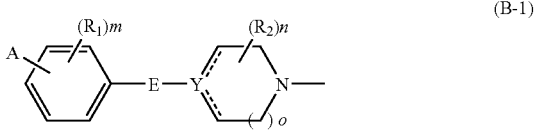

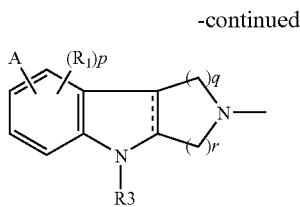

A represents an imidazolyl or pyrazolyl group represented by the following formula (A-1), (A-2), (A-3) or (A-4), or may represent a hydrogen atom or R₁ when B is (B-3):

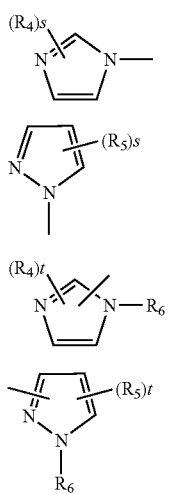

(wherein R₄ and R₅ each independently represents a $C_{1-6}$ alkyl group which may be substituted with G1, a $C_{1-6}$ alkoxy group which may be substituted with G1, a $C_{1-6}$ alkylsulfonyl group which may be substituted with G1, or a halogen atom; R₆ represents a hydrogen atom, a $C_{1-6}$ alkyl group which may be substituted with G1, a $C_{1-6}$ alkylcarbonyl group which may be substituted with G1, a benzoyl group which may be substituted with G1, or a tetrahydropyranyl group;

G1 represents a cyano group, a formyl group, a hydroxyl group, a $C_{1-6}$ alkoxy group, an amino group, a monomethylamino group, a dimethylamino group or a halogen atom, s represents 0 or an integer of 1 to 3, t represents 0 or an integer of 1 or 2, and R₄(s) or R₅(s) may be the same or different when s or t is 2 or more);

R₁ represents a halogen atom, a nitro group, a cyano group, a hydroxyl group, a $C_{1-6}$ alkyl group which may be substituted with G2, a $C_{1-6}$ alkoxy group which may be substituted with G2, a $C_{1-6}$ alkylthio group which may be substituted with G2, a $C_{1-6}$ alkylcarbonyl group which may be substituted with G2, an amino group (which may be substituted with one or two $C_{1-6}$ alkyl groups), a benzoyl group which may be substituted with G2, or a benzyl group which may be substituted with G2;

R₂ represents a $C_{1-6}$ alkyl group which may be substituted with G2;

R₃ represents a hydrogen atom, a $C_{1-6}$ alkyl group which may be substituted with G2, a $C_{1-6}$ alkylcarbonyl group which may be substituted with G2, a benzoyl group which may be substituted with G2, or a benzyl group which may be substituted with G2;

G2 represents a cyano group, a formyl group, a hydroxyl group, a $C_{1-6}$ alkoxy group, a $C_{1-6}$ alkoxycarbonyl group, a nitro group, an amino group, a monomethylamino group, a dimethylamino group or a halogen atom;

m represents 0 or an integer of 1 to 4, and R₁(s) may be the same or different when m is 2 or more;

n represents 0 or an integer of 1 to 10, and R₂(s) may be the same or different when n is 2 or more;

o represents an integer of 1 or 2;

p represents 0 or an integer of 1 to 4, and R₁(s) may be the same or different when p is 2 or more;

q and r each independently represents an integer of 1 or 2;

in the formula (B-1), the dotted line represents a single bond or a double bond and does not simultaneously represent a double bond;

Y represents a carbon atom or a nitrogen atom, which may have a substituent or a multiple bond that satisfies a valence;

E represents an oxygen atom, a sulfur atom or the following formula (1a) when Y represents a carbon atom;

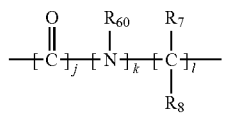

(wherein R₆₀ represents a hydrogen atom, a $C_{1-6}$ alkylcarbonyl group, or a benzoyl group (which may be substituted with a nitro group, a halogen atom, a hydroxyl group, a $C_{1-6}$ alkoxy group, or a $C_{1-6}$ alkyl group); R₇ and R₈ each independently represents a hydrogen atom, a cyano group, a hydroxyl group, a halogen atom, a $C_{1-6}$ alkyl group, a $C_{1-6}$ alkoxy group, a $C_{2-6}$ alkenyl group, a $C_{2-6}$ alkynyl group, a $C_{2-6}$ alkenyloxy group, a $C_{2-6}$ alkynyloxy group, a $C_{1-6}$ acyloxy group, a $C_{3-6}$ cycloalkyl group which may be substituted with G2, or a phenyl group which may be substituted with G2;

j and k independently represent an integer of 0 or 1, and j and k represent 0 when B is (B-2);

l represents 0 or any one of integers of 1 to 16;

R₇(s) and R₈(s) may be the same or different when l is 2 or more);

E represents the formula (1a) when Y represents a nitrogen atom;

D represents an oxygen atom, a sulfur atom or the formula (1a);

X represents an oxygen atom, the formula: SOu (wherein u represents an integer of 0, 1 or 2) or the formula: N—R₉ (wherein R₉ represents a hydrogen atom, a $C_{1-6}$ alkyl group which may be substituted with G2, or a benzyl group which may be substituted with G2);

Z represents a chroman-2-yl group which is substituted with G3, a chroman-4-yl group which is substituted with G3, a 2,3-dihydrobenzofuran-2-yl group which is substituted with G3, a 2,3-dihydrobenzofuran-3-yl group which is substituted with G3, a thiochroman-2-yl group which is substituted with G3, a 2,3-dihydrobenzothiophene-2-yl group which is substituted with G3, a thiochroman-4-yl group which is substituted with G3, a 2,3-dihydrobenzothiophene-3-yl group which is substituted with G3, or a 1,3-benzoxathiol-2-yl group which is substituted with G3;

G3 represents the formula: NHR₁₀

{wherein R₁₀ represents a hydrogen atom, a $C_{1-6}$ alkylcarbonyl group, or a benzoyl group (which may be substitiuted with a nitro group, a halogen atom, a hydroxyl group, a $C_{1-6}$ alkoxy group, or a $C_{1-6}$ alkyl group)};

or the formula: $OR_{11}$

{wherein $R_{11}$ represents a hydrogen atom, a $C_{1-6}$ alkylcarbonyl group, or a benzoyl group (which may be substituted with a hydroxyl group, a $C_{1-6}$ alkoxy group, a halogen atom, or a $C_{1-6}$ alkyl group)}]
or a pharmaceutically acceptable salt thereof.

Second, the present invention is directed to the compound described in claim 1, wherein Z represents a group represented by the following formula (Z-1), (Z-2), (Z-3), (Z-4) or (Z-5):

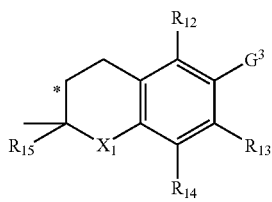
(Z-1)

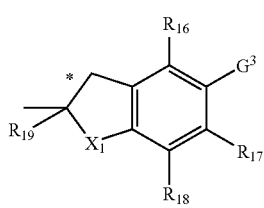
(Z-2)

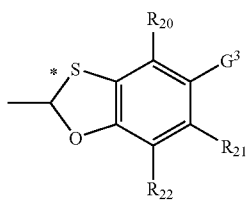
(Z-3)

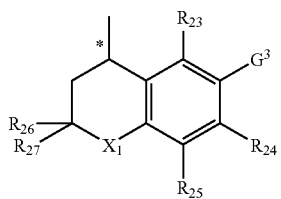
(Z-4)

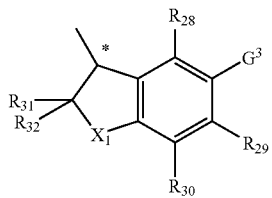
(Z-5)

[wherein * represents an asymmetric carbon atom; $X_1$ represents an oxygen atom or a sulfur atom; $R_{12}$ to $R_{32}$ each independently represents a hydrogen atom or a $C_{1-6}$ alkyl group, and G3 is as defined above] or a pharmaceutically acceptable salt thereof.

Third, the present invention is directed to an antioxidant including, as the active ingredient, one or more compounds or pharmaceutically acceptable salts thereof described in (1) or (2).

Third, the present invention is directed to a therapeutic agent for kidney diseases, including the antioxidant described in (3).

Fourth, the present invention is directed to a therapeutic agent for cerebrovascular diseases, including the antioxidant described in (3).

Fifth, the present invention is directed to a therapeutic agent for circulatory diseases, including the antioxidant described in (3).

Sixth, the present invention is directed to a therapeutic agent for cerebral infarction, including the antioxidant described in (3).

Seventh, the present invention is directed to a therapeutic agent for retinal oxidative damage, including the antioxidant described in (3).

Eighth, the present invention is directed to a therapeutic agent described in (3), wherein the retinal oxidative damage is age-related macular degeneration or diabetic retinopathy.

Ninth, the present invention is directed to a lipoxygenase inhibitor including the antioxidant described in (3).

Tenth, the present invention is directed to a 20-hydroxyeicosatetraenoic acid (20-HETE) synthase inhibitor including the antioxidant described in (3).

The phenylazole compounds or pharmaceutically acceptable salts thereof of the present invention have an antioxidation activity which is effective for treatment of arteriosclerosis, and ischemic organopathy such as myocardial infarction or cerebral infarction, and treatment of diseases such as kidney diseases caused by oxidative cell damage, and can effectively inhibit retinopathy caused by oxidation due to light, and also can give excellent antioxidants containing the phenylazole compounds of the present invention and are useful as retinal oxidative damage inhibitors which exert less side effect, lipoxygenase inhibitors, 20-HETE synthase inhibitors, and therapeutic agents for kidney diseases, cerebrovascular or circulatory diseases and cerebral infarction.

BEST MODE FOR CARRYING OUT THE INVENTION

The present invention provides phenylazole compounds represented by the formula (1):

B-D-Z (1)

[wherein B represents the following formula (B-1), (B-2) or (B-3):

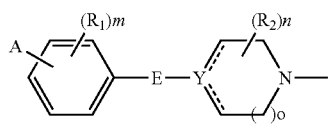
(B-1)

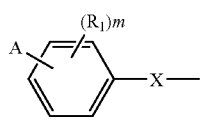
(B-2)

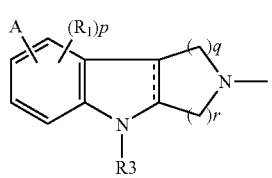
(B-3)

A represents an imidazolyl or pyrazolyl group represented by the following formula (A-1), (A-2), (A-3) or (A-4), or may represent a hydrogen atom or $R_1$ when B is (B-3):

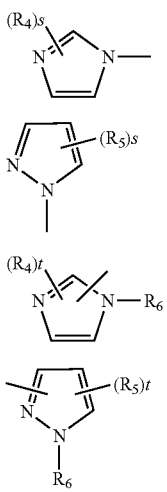

(wherein R₄ and R₅ each independently represents a $C_{1-6}$ alkyl group which may be substituted with G1, such as methyl, ethyl, n-propyl, isopropyl, n-butyl, isobutyl, s-butyl, t-butyl, n-pentyl or n-hexyl; a $C_{1-6}$ alkoxy group which may be substituted with G1, such as methoxy, ethoxy, propoxy, isopropoxy, butoxy, sec-butoxy, isobutoxy or t-butoxy, a $C_{1-6}$ alkylsulfonyl group which may be substituted with G1, such as methylsulfonyl, ethylsulfonyl, propylsulfonyl or butylsulfonyl; or a halogen atom such as fluorine, chlorine, bromine or iodine; R₆ represents a hydrogen atom, a $C_{1-6}$ alkyl group which may be substituted with G1, such as methyl, ethyl, n-propyl, isopropyl, n-butyl, isobutyl, s-butyl, t-butyl, n-pentyl or n-hexyl; a $C_{1-6}$ alkylcarbonyl group which may be substituted with G1, such as methylcarbonyl, ethylcarbonyl, propylcarbonyl or butylcarbonyl, or a benzoyl or which may be substituted with G1, or a tetrahydropyranyl group;

G1 represents a cyano group; a formyl group; a hydroxyl group; a $C_{1-6}$ alkoxy group such as methoxy, ethoxy, propoxy, isopropoxy, butoxy, sec-butoxy, isobutoxy or t-butoxy; an amino group; a monomethylamino group; a dimethylamino group; or a halogen atom such as fluorine, chlorine, bromine or iodine;

s represents 0 or an integer of 1 to 3;

t represents 0 or an integer of 1 or 2;

R₄(s) or R₅(s) may be the same or different when s or t is 2 or more);

an imidazolyl or pyrazolyl group represented by A may have the following tautomeric structure when R6 is a hydrogen atom;

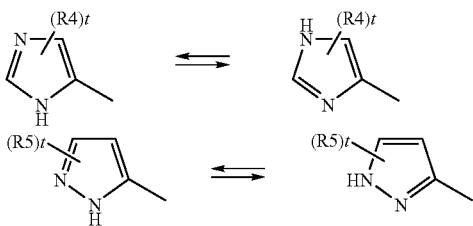

A is preferably a 1-H-imidazol-2-yl group, a 1-H-imidazol-4-yl group, a 1-pyrazole group, a 1-methylimidazol-2-yl group, a 1-methylimidazol-5-yl group, a 1-methylimidazol-4-yl group, a 1-methylpyrazol-4-yl group, a 1-imidazolyl group, a 1H-pyrazol-5-yl group, a 1H-pyrazol-4-yl group, a 1-methylpyrazol-5-yl group, a 1-methylpyrazol-3-yl group, a 1-benzoylpyrazol-4-yl group or a 1-(2-tetrahydropyranyl)-pyrazol-3-yl group, and A is more preferably a 1-imidazolyl group or a 1-H-pyrazol-5-yl group, which is attached to the 3- or 4-position of the benzene ring;

R₁ represents a halogen atom such as fluorine, chlorine, bromine or iodine; a nitro group; a cyano group; a hydroxyl group; a $C_{1-6}$ alkyl group which may be substituted with G2, such as methyl, ethyl, n-propyl, isopropyl, n-butyl, isobutyl, s-butyl, t-butyl, n-pentyl or n-hexyl; $C_{1-6}$ alkoxy group which may be substituted with G2, such as methoxy, ethoxy, propoxy, isopropoxy, butoxy, sec-butoxy, isobutoxy or t-butoxy; a $C_{1-6}$ alkylthio group which may be substituted with G2, such as methylthio, ethylthio, n-propylthio, isopropylthio, n-butylthio, isobutylthio, sec-butylthio or t-butylthio; a $C_{1-6}$ alkylcarbonyl group which may be substituted with G2, such as methylcarbonyl, ethylcarbonyl, propylcarbonyl or butylcarbonyl; an amino group (which may be substituted with one or more $C_{1-6}$ alkyl groups such as methyl, ethyl, n-propyl, isopropyl, n-butyl, isobutyl, s-butyl, t-butyl, n-pentyl or n-hexyl); a benzoyl group which may be substituted with G2; or a benzyl group which may be substituted with G2;

R₂ represents a $C_{1-6}$ alkyl group which may be substituted with G2, such as methyl, ethyl, n-propyl, isopropyl, n-butyl, isobutyl, s-butyl, t-butyl, n-pentyl or n-hexyl;

R₃ represents a hydrogen atom; $C_{1-6}$ alkyl group which may be substituted with G2, such as methyl, ethyl, n-propyl, isopropyl, n-butyl, isobutyl, s-butyl, t-butyl, n-pentyl or n-hexyl; a $C_{1-6}$ alkylcarbonyl group which may be substituted with G2, such as methylcarbonyl, ethylcarbonyl, propylcarbonyl or butylcarbonyl; a benzoyl group hich may be substituted with G2; or a benzyl group which may be substituted with G2;

G2 represents a cyano group; a formyl group; a hydroxyl group; a $C_{1-6}$ alkoxy group such as methoxy, ethoxy, propoxy, isopropoxy, butoxy, sec-butoxy, isobutoxy or t-butoxy; a $C_{1-6}$ alkoxycarbonyl group such as methoxycarbonyl, ethoxycarbonyl, propoxycarbonyl, isopropoxy, butoxycarbonyl or t-butoxycarbonyl; a nitro group; an amino group; a monomethylamino group; a dimethylamino group; or a halogen atom, such as fluorine, chlorine, bromine or iodine;

m represents 0 or an integer of 1 to 4, and R₁(s) may be the same or different when m is 2 or more;

n represents 0 or an integer of 1 to 10, and R₂(s) may be the same or different when n is 2 or more;

o represents an integer of 1 or 2;

p represents 0 or an integer of 1 to 4, and R₁(s) may be the same or different when p is 2 or more;

q and r each independently represents an integer of 1 or 2;

in the formula (B-1), the dotted line represents a single bond or a double bond and does not simultaneously represent a double bond;

Y represents a carbon atom or a nitrogen atom, which may have a substituent or a multiple bond that satisfies a valence;

E represents an oxygen atom, a sulfur atom or the following formula (1a) when Y represents a carbon atom;

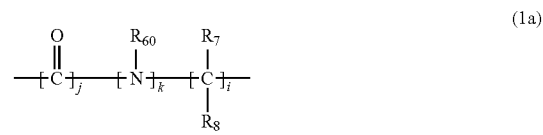

(wherein $R_{60}$ represents a hydrogen atom; a $C_{1-6}$ alkylcarbonyl group or a benzoyl group (which may be substituted with a nitro group; a halogen atom such as fluorine, chlorine, bromine or iodine; a hydroxyl group; a $C_{1-6}$ alkoxy group such as methoxy, ethoxy, propoxy, isopropoxy, butoxy, sec-butoxy, isobutoxy or t-butoxy; or a $C_{1-6}$ alkyl group such as methyl, ethyl, n-propyl, isopropyl, n-butyl, sec-butyl, isobutyl or t-butyl); and $R_7$ and $R_8$ each independently represents a hydrogen atom; a cyano group; a hydroxyl group; a halogen atom such as fluorine, chlorine, bromine or iodine; a $C_{1-6}$ alkyl group such as methyl, ethyl, n-propyl, isopropyl, n-butyl, sec-butyl, isobutyl or t-butyl; a $C_{1-6}$ alkoxy group such as methoxy, ethoxy, propoxy, isopropoxy, butoxy, sec-butoxy, isobutoxy or t-butoxy; a $C_{2-6}$ alkenyl group such as ethenyl, 1-propenyl, 2-propenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl or 5-hexenyl; a $C_{2-6}$ alkynyl group such as ethynyl, 1-propynyl, 2-propynyl, 1-butynyl, 2-butynyl, 3-butynyl, 1-methyl-2-propynyl, 2-methyl-3-butynyl, 1-pentynyl, 2-pentynyl, 3-pentynyl, 4-pentynyl, 1-methyl-2-butynyl, 2-methyl-3-pentynyl, 1-hexynyl or 1,1-dimethyl-2-butynyl; a $C_{2-6}$ alkenyloxy group such as allyloxy, 2-propenyloxy, 2-butenyloxy or 2-methyl-3-propenyloxy; a $C_{2-6}$ alkynyloxy group such as 2-propynyloxy, 2-butynyloxy or 1-methyl-2-propynyloxy; a $C_{1-6}$ acyloxy group such as acetoxy, propionyloxy or butyryloxy; a $C_{3-6}$ cycloalkyl group which may be substituted with G2, such as cyclopropyl, 1-methylcyclopropyl, 2-methylcyclopropyl, 2,2-dimethylcyclopropyl, cyclobutyl, cyclopentyl or cyclohexyl; or a phenyl group which may be substituted with G2;

j and k independently represent an integer of 0 or 1, and j and k represent 0 when B is (B-2);

l represents 0 or an integer of 1 to 16;

$R_7(s)$ and $R_8(s)$ may be the same or different when l is 2 or more);

E represents the formula (1a) when Y represents a nitrogen atom;

D represents an oxygen atom, a sulfur atom or the formula (1a);

X represents an oxygen atom, the formula: $SO_u$ (wherein u represents 0 or an integer of 1 or 2) or the formula: $N-R_9$ (wherein $R_9$ represents a hydrogen atom, a $C_{1-6}$alkyl group which may be substituted with G2, such as methyl, ethyl, n-propyl, isopropyl, n-butyl, sec-butyl, isobutyl or, t-butyl; or a benzyl group which may be substituted with G2);

Z represents a chroman-2-yl group which is substituted with G3, a chroman-4-yl group which is substituted with G3, a 2,3-dihydrobenzofuran-2-yl group which is substituted with G3, a 2,3-dihydrobenzofuran-3-yl group which is substituted with G3, a thiochroman-2-yl group which is substituted with G3, a 2,3-dihydrobenzothiophene-2-yl group which is substituted with G3, a thiochroman-4-yl group which is substituted with G3, a 2,3-dihydrobenzothiophene-3-yl group which is substituted with G3, or a 1,3-benzoxathiol-2-yl group which is substituted with G3;

Z is preferably the following formula (Z-1), (Z-2), (Z-3), (Z-4) or (Z-5);

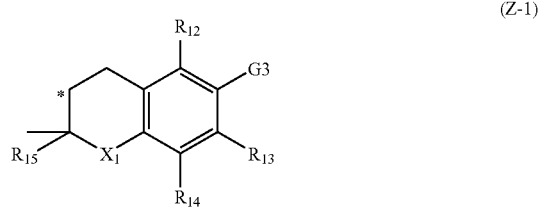

(Z-1)

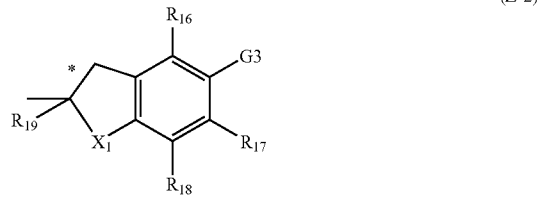

(Z-2)

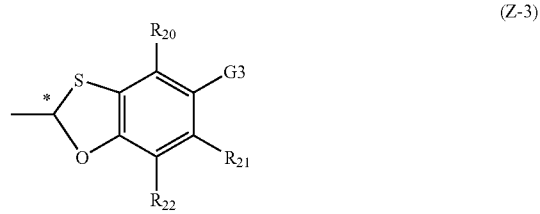

(Z-3)

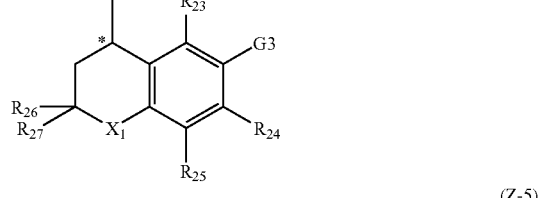

(Z-4)

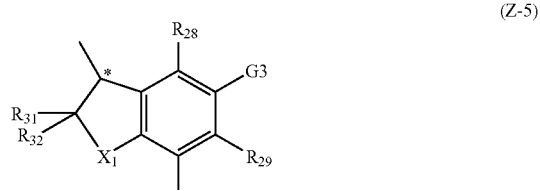

(Z-5)

[wherein * represents an asymmetric carbon atom; $X_1$ represents an oxygen atom or a sulfur atom; $R_{12}$ to $R_{32}$ each independently represents a hydrogen atom, or a $C_{1-6}$ alkyl group such as methyl, ethyl, n-propyl, isopropyl, n-butyl, sec-butyl, isobutyl or t-butyl];

G3 represents the formula: $NHR_{10}$

{wherein $R_{10}$ represents a hydrogen atom; a $C_{1-6}$ alkylcarbonyl group such as methoxycarbonyl, ethoxycarbonyl, propoxycarbonyl, isopropoxy, butoxycarbonyl or t-butoxycarbonyl; or a benzoyl group (which may be substituted with a nitro group; a halogen atom such as fluorine, chlorine, bromine or iodine; a hydroxyl group; a $C_{1-6}$ alkoxy group; or a $C_{1-6}$ alkyl group such as methyl, ethyl, n-propyl, isopropyl, n-butyl, sec-butyl, isobutyl or t-butyl)};

or the formula: $OR_{11}$

{wherein $R_{11}$ represents a hydrogen atom; a $C_{1-6}$ alkylcarbonyl group such as methoxycarbonyl, ethoxycarbonyl, propoxycarbonyl, isopropoxy, butoxycarbonyl or t-butoxycarbonyl; or a benzoyl group (which may be substituted with a hydroxyl group; a $C_{1-6}$ alkoxy group; a nitro group; a halogen atom such as fluorine, chlorine, bromine or iodine; or a $C_{1-6}$ alkyl group such as methyl, ethyl, n-propyl, isopropyl, n-butyl, sec-butyl, isobutyl or t-butyl)}] or pharmaceutically acceptable salts thereof.

(Process for Production of Compounds)

The compound in which the moiety B is B-1 among phenylazole compounds represented by the formula (1) of the present invention can be produced by the following production processes 1 to 7.

Production Process 1: Step 1

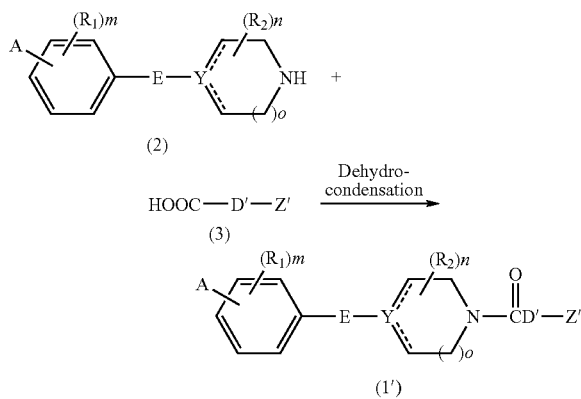

{in the formula (2), A, E, Y, R1, R2, m, n and o are the same as A, E, Y, R1, R2, m, n and o in the formula (1) and, in the formula (3), there is attained equivalence between D in the formula (1) and the formula (C=O)-D', and Z' represents Z when G3 in the formula (Z-1), (Z-2), (Z-3), (Z-4) or (Z-5) is a nitro group or $OR_{11}$}

In the step 1, by dehydrocondensing carboxylic acid represented by the formula (3) with an amine represented by the formula (2) using a conventional process, there can be obtained a phenylazole compound represented by the formula (1') (wherein A, E, Y, R1, R2, m, n and o are the same as A, E, Y, R1, R2, m, n and o in the formula (2), and D' and Z' are the same groups as for D' and Z' in the formula (3)) of the present invention.

This dehydrocondensation reaction can be carried out in the presence of a suitable condensing agent. In this case, as the condensing agent, for example, 1,3-dicyclohexylcarbodiimide, 1-(3-dimethylaminopropyl)-3-ethylcarbodiimide and 2-ethoxy-1-ethoxycarbonyl-1,2-dihydroquinoline can be used.

In this reaction, the reaction can be allowed to proceed more quickly by the coexistence of N-hydroxysuccinic acidimide, 1-hydroxybenzotriazole and 3,4-dihydro-3-hydroxy-4-oxo-1,2,3-benzotriazine in the reaction system.

The reaction solvent is not specifically limited as far as it is a solvent which is inactive to the reaction, and examples thereof include ethers such as diethyl ether, tetrahydrofuran (hereinafter abbreviated to THF) and 1,4-dioxane; aromatic hydrocarbons such as benzene, toluene and xylene; halogenated hydrocarbons such as dichloromethane, chloroform and 1,2-dichloroethane; acetonitrile, dimethyl formamide (hereinafter abbreviated to DMF), dimethyl sulfoxide (hereinafter abbreviated to DMSO) and pyridine.

The reaction is carried out at a temperature within a range from −15° C. to about a boiling point of the solvent, and preferably from 0 to 80° C.

Production Process 2:

Alternatively, the compound can also be produced according to the following reaction scheme.

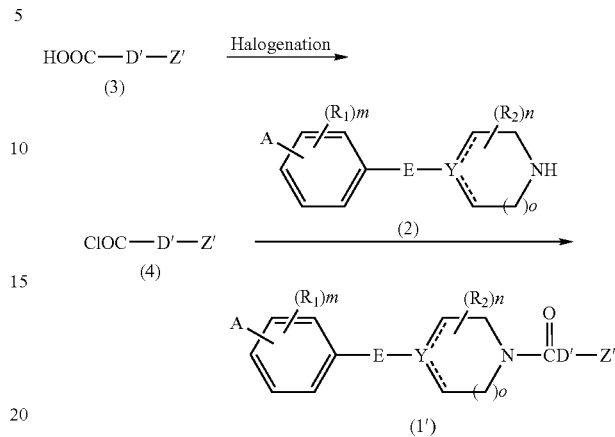

{in the formula (2), A, E, Y, R1, R2, m, n and o are the same as A, E, Y, R1, R2, m, n and o in the formula (1) and, in the formula (3'), there is attained equivalence between D in the formula (1) and the formula (C=O)-D', and Z' represents Z when G3 in the formula (Z-1), (Z-2), (Z-3), (Z-4) or (Z-5) is a nitro group or $OR_{11}$}

That is, an acid chloride (4) is obtained from a carboxylic acid derivative represented by the formula (3') using a halogenating agent such as thionyl chloride, phosphorus pentachloride or oxalic acid dichloride, and the resulting acid chloride is reacted with an amine represented by the formula (2) in an inactive organic solvent in the presence of a base to obtain a phenylazole compound represented by the formula (1') (wherein A, E, Y, R1, R2, m, n and o are the same as A, E, Y, R1, R2, m, n and o in the formula (2,) and D' and Z' are the same groups as for D' and Z' in the formula (3)) of the present invention.

The reaction solvent is not specifically limited as far as it is a solvent which is inactive to the reaction, and there can be used, for example, ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

Examples of the base used in the reaction include amines such as triethylamine, pyridine and 1,8-diazabicyclo[5.4.0]undec-7-ene (hereinafter abbreviated to DBU); and inorganic bases such as sodium hydrogen carbonate, sodium carbonate, potassium carbonate and sodium hydroxide.

The reaction is carried out at a temperature within a range from −15° C. to about a boiling point of the solvent, and preferably from 0 to 80° C.

Production Process 3:

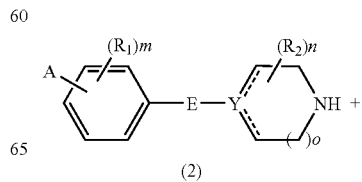

-continued

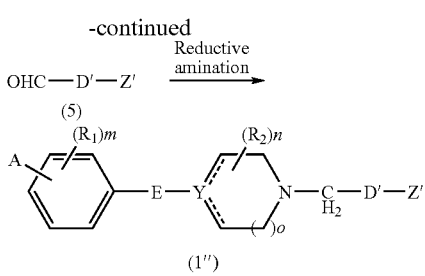

{in the formula (2), A, E, Y, R1, R2, m, n and o are the same as A, E, Y, R1, R2, m, n and o in the formula (1) and, in the formula (5), there is attained equivalence between D in the formula (1) and the formula $CH_2$-D', and Z' represents Z when G3 in the formula (Z-1), (Z-2), (Z-3), (Z-4) or (Z-5) is a nitro group or $OR_{11}$}

That is, by performing reductive amination of an aldehyde represented by the formula (5) and an amine represented by the formula (2) using a conventional process, there can be obtained a phenylazole compound represented by the formula (1″) (wherein A, E, Y, R1, R2, m, n and o are the same as A, E, Y, R1, R2, m, n and o in the formula (2), and D' and Z' are the same groups as for D' and Z' in the formula (5)) of the present invention.

This reductive amination reaction can be carried out by adding a reducing agent in the presence of a suitable acid catalyst. In this case, examples of the acid catalyst include organic acids such as acetic acid and p-toluenesulfonic acid; and inorganic acids such as sulfuric acid and hydrochloric acid. Examples of the reducing agent include $NaBH_4$ and sodium triacetoxyborohydride.

The reaction solvent is not specifically limited as far as it is a solvent which is inactive to the reaction, and examples thereof include ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

The reaction is carried out at a temperature within a range from −15° C. to about a boiling point of the solvent, and preferably room temperature.

Production Process 4: Step 2

An aniline compound as the phenylazole compound of the present invention can be produced by the following process.

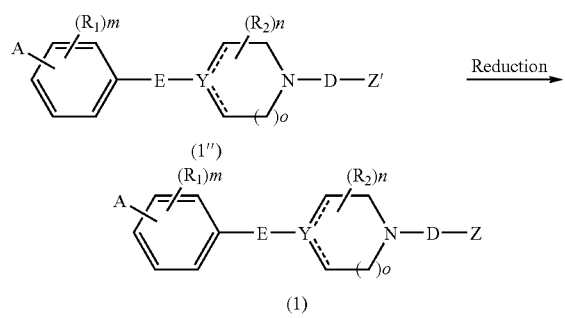

{in the formula (1″), A, E, Y, R1, R2, m, n and o are the same as A, E, Y, R1, R2, m, n and o in the formula (1), and Z' represents Z when G3 in the formula (Z-1), (Z-2), (Z-3), (Z-4) or (Z-5) is a nitro group}

That is, in the step 2, by hydrogenating the phenylazole compound having a nitro group represented by the formula (1″) obtained in the production processes 1 to 3 of the present invention using a catalyst, there is obtained an aniline compound, as the phenylazole-based compound represented by the formula (1) in which a nitro group of the substituent G3 in Z' is converted into $NHR_{10}$ of the present invention.

Examples of the catalyst include palladium carbon, platinum dioxide and Raney nickel.

As the reaction solvent, there can be used alcohols such as methanol and ethanol; ethers such as diethyl ether, THF and 1,4-dioxane; aromatic hydrocarbons such as benzene, toluene, xylene and cyclohexane; amides such as DMF; organic acids such as formic acid and acetic acid; esters such as ethyl acetate; and solvent mixtures thereof.

The reaction is carried out at a temperature within a range from 0° C. to about a boiling point of the solvent, and preferably from 20 to 80° C.

Production Process 5:

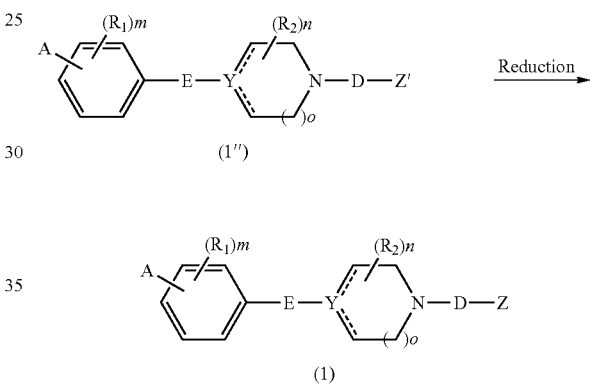

{in the formula (1″), A, E, Y, R1, R2, m, n and o are the same as A, E, Y, R1, R2, m, n and o in the formula (1), and Z' represents Z when G3 in the formula (Z-1), (Z-2), (Z-3), (Z-4) or (Z-5) is a nitro group}

That is, by hydrogenating the phenylazole compound having a nitro group represented by the formula (1″) of the present invention using a metal catalyst and an acid, there is obtained an aniline compound, as the phenylazole compound represented by the formula (1) in which a nitro group of the substituent G3 in Z' is converted into $NHR_{10}$ of the present invention.

Examples of the metal catalyst include stannous chloride.

Examples of the acid include sulfuric acid or hydrochloric acid.

As the reaction solvent, there can be used alcohols such as methanol and ethanol; ethers such as diethyl ether, THF and 1,4-dioxane; hydrocarbons such as benzene, toluene, xylene and cyclohexane; amides such as DMF; and solvent mixtures thereof.

The reaction is carried out at a temperature within a range from 0° C. to about a boiling point of the solvent, and preferably from 60 to 80° C.

Production Process 6:

Step 1:

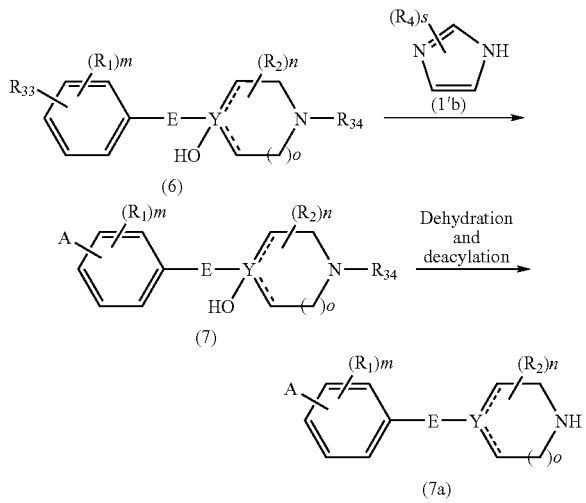

Step 2:

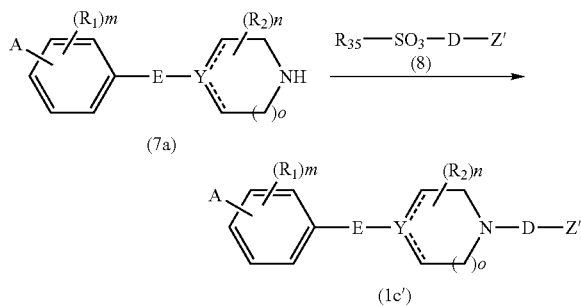

{in the formula (1c'), A, E, R1, R2, m, n and o are the same as A, E, R1, R2, m, n and o in the formula (7a); D is the same group as for D in the formula (1); Z' represents Z when G3 in the formula (Z-1), (Z-2), (Z-3), (Z-4) or (Z-5) is a nitro group or $OR_{11}$, in the formula (6), E, R1, R2, m, n and o are the same as E, R1, R2, m, n and o in the formula (1); Y represents a carbon atom; $R_{34}$ represents an acyl group; $R_{33}$ represents a halogen atom; in the formula (1'b), R4 and s are the same as R4 and s in the formula (A-1); in the formula (7), A, E, R1, R2, m, n, $R_{34}$ and o are the same as A, E, R1, R2, m, n, $R_{34}$ and o in the formula (6); A represents an imidazolyl group derived from the formula (1'b); in the formula (7a), A, E, R1, R2, m, n and o are the same as A, E, R1, R2, m, n and o in the formula (7); in the formula (8), D is the same group as for D in the formula (1); Z' represents Z when G3 in the formula (Z-1), (Z-2), (Z-3), (Z-4) or (Z-5) is a nitro group or $OR_{11}$; and $R_{34}$ represents a perfluoroalkyl group}

The phenylazole compound represented by the formula (1c') can be produced by the process comprising the step 1 of reacting a compound represented by the formula (6) with an imidazole compound represented by the formula (1'b) in a solvent in the presence of a catalyst, and dehydrating and deacylating a compound represented by the formula (7) to obtain a compound represented by the formula (7a), and the second step of reacting a compound represented by the formula (7a) with a perfluoroalkane sulfonate ester compound represented by the formula (8) in a solvent.

In the compound represented by the formula (6) used as a raw material in the step 1, examples of the acyl group as for $R_{34}$ include acetyl group, propionyl group and butyryl group and examples of the halogen atom as for $R_{33}$ include bromine atom, chlorine atom, fluorine atom and iodine atom. The compound having such a group represented by the formula (6) can be reacted with the imidazole compound represented by the formula (1'b) in a BTX solvent such as xylene, toluene or mesitylene using 1,10-phenanthroline, 1,5-diphenyl-1,4-pentadien-3-one, cesium carbonate or a copper (I) trifluoromethane sulfonate benzene complex. The reaction is carried out by heating at reflux (a temperature corresponding to a boiling point of the solvent within a range from 100 to 150° C.) in an argon gas flow to obtain a product represented by the formula (7). The reaction product represented by the formula (7) can be dehydrated by heating at reflux using concentrated hydrochloric acid and, after the reaction, the reaction product is neutralized with an alkali to obtain a compound represented by the formula (7a).

Examples of the perfluoroalkane sulfonate ester compound represented by the formula (8) used in the step 2 include those having a trifluoromethyl group or a perfluoroethyl group as $R_{35}$. Among these groups, a trifluoromethyl group is preferable. The perfluoroalkanesulfonic acid compound can be reacted with the compound represented by the formula (7a) obtained in the step 1 by heating at reflux (a temperature within a range from 100 to 150° C.) in an ether-based solvent such as acetonitrile, dioxane or THF, or a BTX-based solvent such as benzene or toluene using, as a catalyst, a base such as sodium carbonate or potassium carbonate.

Production Process 7:

The aniline compound as the phenylazole compound of the present invention can be produced by the following process.

Step 3:

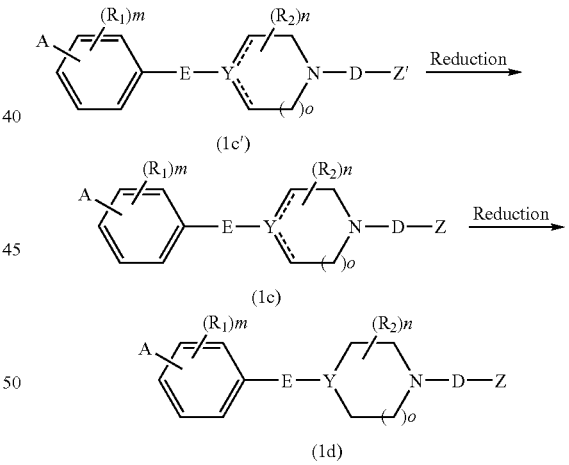

{in the formula (1c), A, E, Y, R1, R2, m, n and o are the same as A, E, Y, R1, R2, m, n and o in the formula (1c'), Z represents a group in which a nitro group of the substituent G3 in Z' in the formula (1c') is converted into $NHR_{10}$ and, in the formula (1d), A, E, Y, R1, R2, m, n and o are the same as A, E, Y, R1, R2, m, n and o in the formula (1c)}

That is, in the step 3, the phenylazole compound having a nitro group represented by the formula (1c') obtained in the step 2 is reduced to obtain a phenylazole-based compound represented by the formula (1c) in which a nitro group of the substituent G3 in Z' is converted into $NHR_{10}$. The phenylazole-based compound represented by the formula (1c') can be carried out by the process of heating at reflux (a temperature within a range from 100 to 150° C.) using a catalyst such as stannous chloride dihydrate and neutralizing with an alkali after the completion of the reaction.

Furthermore, the reaction of reducing the phenylazole-based compound represented by the formula (1c) obtained in the step 3 to obtain a phenylazole-based compound represented by the formula (1d) can be carried out by hydrogenating in a solvent, for example, alcohol such as methanol or ethanol, organic acid such as acetic acid, or a solvent mixture thereof at room temperature or 0 to 60° C. using a catalyst such as palladium.

A 3-imidazole compound can be synthesized by the same process as described above. Also an amide type compound can be synthesized by the same process as described above.

The compound in which the moiety B is (B-2) among phenylazole compounds represented by the formula (1) of the present invention can be produced as shown in the following production processes 8 to 11.

Production Process 8:

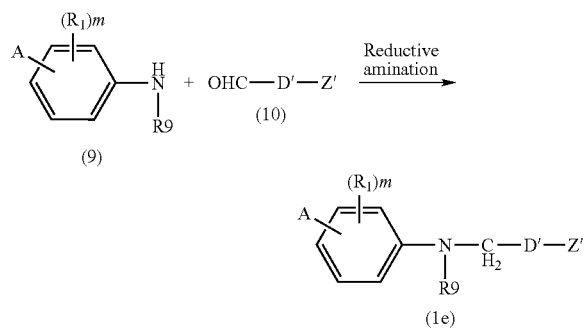

{in the formula (9), A, R1, R9 and m are the same as A, R1, R9 and m in the formula (1) and, in the formula (10), there is attained equivalence between D in the formula (1) and the formula $CH_2$-D', and Z' represents Z when G3 is a nitro group or $OR_{11}$ in the Z in the formula (1)}

That is, a phenylazole derivative (1e) represented by the formula (1) of the present invention is obtained by the reductive amination reaction thorough a conventional process using an aldehyde represented by formula (10) and an amine represented by the formula (9) as a starting material.

Such a reductive amination reaction can be carried by adding a reducing agent in the presence of a suitable acid catalyst. In this case, examples of the acid catalyst include organic acids such as acetic acid and p-toluenesulfonic acid; and inorganic acids such as sulfuric acid and hydrochloric acid. Examples of the reducing agent include $NaBH_4$ and sodium triacetoxyborohydride.

The reaction solvent is not specifically limited as far as it is a solvent which is inactive to the reaction, and examples thereof include ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

The reaction is carried out at a temperature within a range from −15° C. to about a boiling point of the solvent, and preferably room temperature.

Production Process 9:

The phenylazole derivative represented by the formula (1) of the present invention can be produced by the following process.

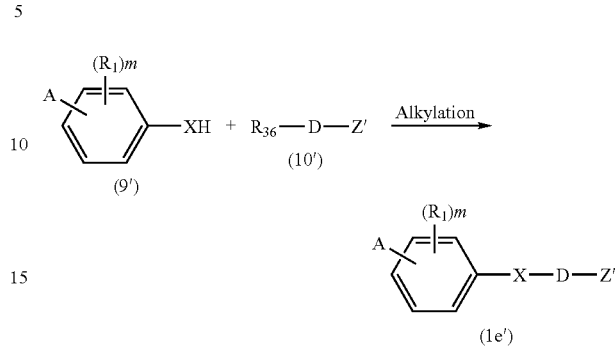

{in the formula (9'), A, R1, m and X are the same as A, R1, m and X in formula (1) and, in the formula (10'), D is the same as D in the formula (1), Z' represents Z when G3 is a nitro group or $OR_{11}$ in Z in the formula (1), and $R_{36}$ represents a leaving group derived from an alcohol, for example, halogen such as chlorine, bromine or iodine; or a sulfonate ester such as methane sulfonate, toluene sulfonate or trifluoromethane sulfonate}

That is, a compound (1e') as the phenylazole derivative represented by the formula (1) of the present invention is obtained by alklylating a compound represented by the formula (9') with a compound represented by the formula (10').

Such a reaction can be carried out in an inactive solvent, for example, ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF and DMSO at a temperature within a range from −15° C. to about a boiling point of the solvent, preferably from 0 to 80° C. in the presence of a base, for example, amines such as triethylamine, pyridine and DBU; and inorganic bases such as sodium hydrogen carbonate, sodium carbonate, potassium carbonate and sodium hydroxide.

A 4-(imidazol-1-yl)thiophenol represented by the formula (6') can be produced by a known process described in the document (for example, Specification of French Patent Publication No. 2267101).

Production Process 10:

The phenylazole derivative represented by the formula (1) of the present invention can be produced as shown in the following scheme.

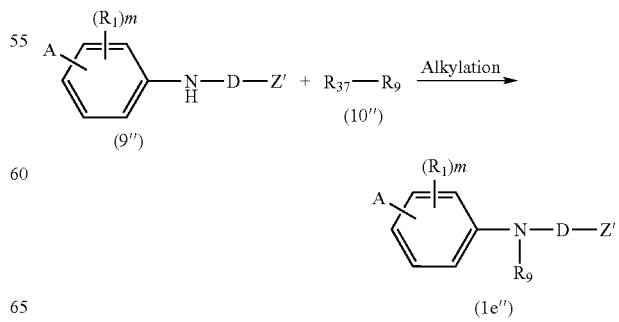

{in the formula (10″), R$_9$ is the same as R$_9$ in the formula (1), in the formula (9″), A, R1, m and D are the same as A, R1, m and D in the formula (1), Z' represents Z when G3 is a nitro group or a OR$_{11}$ group in Z in the formula (1), in the formula (10″), R$_{37}$ represents a leaving group, for example, halogen such as chlorine, bromine or iodine, and a sulfonate ester such as methane sulfonate, toluene sulfonate or trifluoromethane sulfonate}

That is, a compound (1e″) as the phenylazole derivative represented by the formula (1) of the present invention is obtained by alklylating a compound represented by the formula (9″) with a compound represented by the formula (10″).

Such a reaction can be carried out in an inactive solvent, for example, ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF and DMSO at a temperature within a range from −15° C. to about a boiling point of the solvent, preferably from 0 to 100° C. in the presence of a base, for example, amines such as triethylamine, pyridine and DBU; and inorganic bases such as sodium hydrogen carbonate, sodium carbonate, potassium carbonate and sodium hydroxide.

Production Process 11:

The phenylazole derivative represented by the formula (1) of the present invention can be produced as shown in the following scheme.

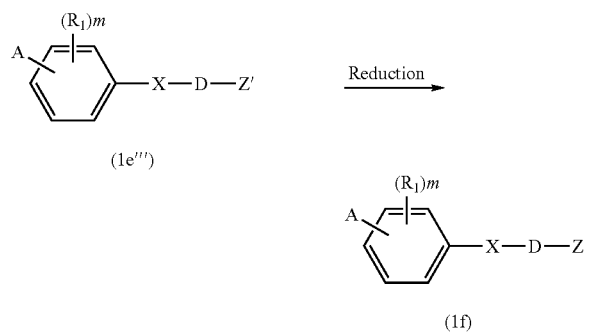

{in the formula (1e‴), A, R1, m, D and X are the same as A, R1, m, D and X in the formula (1), and Z' represents Z when G3 is a nitro group in Z in the formula (1)}

According to this reductive reaction, there can be obtained an aniline compound (1f) as the phenylazole derivative represented by the formula (1) of the present invention in which a nitro group of the substituent G3 in Z' is converted into NHR$_{10}$ by hydrogenating a nitro compound represented by the formula (1e‴) using a catalyst or reducing using a reducing agent.

Examples of the catalyst used for hydrogenation include palladium carbon, palladium hydroxide, platinum dioxide and Raney nickel.

Examples of the reaction solvent include alcohols such as methanol and ethanol; ethers such as diethyl ether, THF and 1,4-dioxane; hydrocarbons such as benzene, toluene, xylene and cyclohexane; amides such as DMF; organic acids such as formic acid and acetic acid; esters such as ethyl acetate, and solvent mixtures thereof.

When using these reducing agents, the reduction can be carried out in an alcohol such as methanol or ethanol using hydrochloric acid and stannous chloride, or carried out in a solvent mixture of acetone or methyl ethyl ketone and water using acetic acid and iron.

The reaction can be carried out at a temperature within a range from 0° C. to about a boiling point of the solvent.

In the present invention, the objective product can be obtained by carrying out a conventional work-up after the completion of the reaction.

The compound in which the moiety B is (B-3) represented by the formula (1) among the phenylazole-based compounds of the present invention can be produced by the following production processes 12 to 15.

Production Process 12:

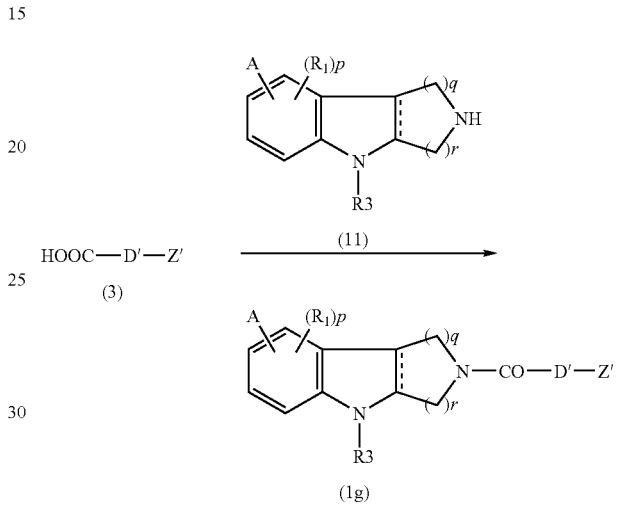

{in the formula (1g), A, R1, R3, p, q and r are the same as A, R1, R3, p, q and r in the formula (1), in the formula (3) and the formula (4), there is attained equivalence between D in the formula (1) and the formula (C=O)-D', and Z' represents Z when G3 is a nitro group or OR$_{11}$ in Z in the formula (1)}

That is, an amide derivative as the nitro compound represented by the formula (1g) can be obtained by halogenating a carboxylic acid derivative represented by the formula (3) using a halogenating agent such as thionyl chloride, phosphorus pentachloride or oxalic acid dichloride to obtain an acid chloride (4), and reacting the resulting acid chloride with an amine represented by the formula (11) in an inactive organic solvent in the presence of a base.

The reaction solvent is not specifically limited as far as it is a solvent which is inactive to the reaction and, for example, there can be used ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

Examples of the base used in the reaction include amines such as triethylamine, pyridine and DBU; and inorganic bases such as sodium hydrogen carbonate, sodium carbonate, potassium carbonate and sodium hydroxide.

The reaction is carried out at a temperature within a range from −15° C. to about a boiling point of the solvent, and preferably from 0 to 80° C.

Production Process 13:

Alternatively, the compound can also be produced according to the following reaction scheme.

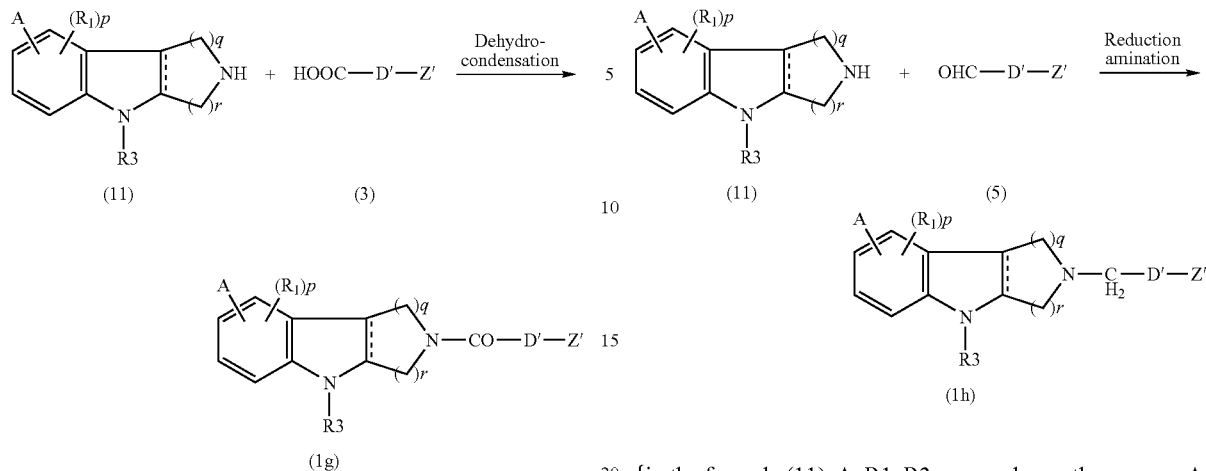

{in the formula (11), A, R1, R3, p, q and r are the same as A, R1, R3, p, q and r in the formula (1), in the formula (3), there is attained equivalence between D in the formula (1) and the formula (C=O)-D', and Z' represents Z when G3 is a nitro group or $OR_{11}$ in Z in the formula (1)}

That is, an amide derivative as the nitro compound represented by the formula (1g) is obtained by dehydrocondensing a carboxylic acid represented by the formula (3) with an amine represented by the formula (11) using a conventional process.

This dehydrocondensation reaction can be carried out in the presence of a suitable condensing agent. In this case, examples of the condensing agent include 1,3-dicyclohexylcarbodiimide, 1-(3-dimethylaminopropyl)-3-ethylcarbodiimide and 2-ethoxy-1-ethoxycarbonyl-1,2-dihydroquinoline.

In this reaction, the reaction can be allowed to proceed more quickly by the coexistence of N-hydroxysuccinic acid imide, 1-hydroxybenzotriazole and 3,4-dihydro-3-hydroxy-4-oxo-1,2,3-benzotriazine in the reaction system.

The reaction solvent is not specifically limited as far as it is a solvent which is inactive to the reaction, and examples thereof include ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

The reaction is carried out at a temperature within a range from −15° C. to about a boiling point of the solvent, and preferably from 0 to 80° C.

The compound represented by the general formula (2) can be produced by a known process described in the document (for example, Journal of Medicinal Chemistry, 1980, Vol. 23, P. 635-643, Synthesis, 1977, P. 645-646, and Journal of Medicinal Chemistry, 1977, Vol. 20, P. 600-602.

Production Process 14:

Alternatively, the compound can also be produced according to the following reaction scheme.

{in the formula (11), A, R1, R3, p, q and r are the same as A, R1, R3, p, q and r in the formula (1), in the formula (5), there is attained equivalence between D in the formula (1) and the formula $CH_2$-D', and Z' represents Z when G3 is a nitro group or $OR_{11}$ in Z in the formula (1)}

That is, an amine derivative as the nitro compound represented by the formula (1h) can be obtained by reductive amination of an aldehyde represented by the formula (5) and an amine represented by the formula (11) using a conventional process.

This reductive amination reaction can be carried out by adding a reducing agent in the presence of a suitable acid catalyst. In this case, examples of the acid catalyst include organic acids such as acetic acid and p-toluenesulfonic acid; and inorganic acids such as sulfuric acid and hydrochloric acid. Examples of the reducing agent include sodium borohydride and sodium triacetoxyborohydride.

The reaction solvent is not specifically limited as far as it is a solvent which is inactive to the reaction, and examples thereof include ethers such as diethyl ether, THF and 1,4-dioxane; aromatic hydrocarbons such as benzene, toluene and xylene; halogenated hydrocarbons such as dichloromethane, chloroform and 1,2-dichloroethane; acetonitrile, DMF, DMSO and pyridine.

The reaction is carried out at a temperature within a range from −15° C. to about a boiling point of the solvent, and preferably room temperature.

Production Process 15:

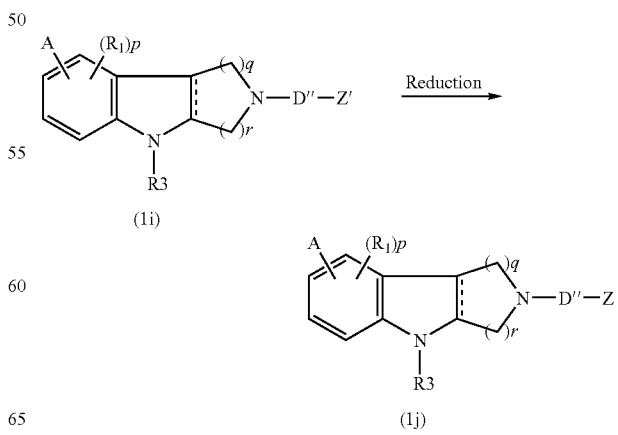

{in the formula, A, D", Z, R1, R3, p, q and r are the same as A, D, Z, R1, R3, p, q and r in the formula (1), and Z' represents Z when G3 is a nitro group in Z in the formula (1)}

That is, an aniline compound represented by the formula (1j) is obtained by hydrogenating a nitro compound represented by the formula (1i) such as formula (1g) or (1h) using a catalyst.

Examples of the catalyst include palladium carbon, platinum dioxide and Raney nickel.

As the reaction solvent, there can be used alcohols such as methanol and ethanol; ethers such as diethyl ether, THF and 1,4-dioxane; hydrocarbons such as benzene, toluene, xylene and cyclohexane; amides such as DMF; organic acids such as formic acid and acetic acid; esters such as ethyl acetate, and solvent mixtures thereof.

The reaction is carried out at a temperature within a range from 0° C. to about a boiling point of the solvent, and preferably from 20 to 80° C.

In the present invention, the objective product can be obtained by carrying out a conventional work-up after the completion of the reaction.

The structure of the compounds of the present invention compound was decided by IR, NMR and MS.

In the phenylazole compounds represented by the formula (1) of the present invention, some optical active substances and tautomers can exist. These optical active substances and tautomers are included in the scope of the present invention.

Pharmaceutically acceptable salts of the phenylazole compounds represented by the formula (1) of the present invention are not specifically limited as far as they are salts of the phenylazole compounds represented by the formula (1) and are pharmaceutically acceptable, and examples of salts include salts of inorganic acids such as hydrochloric acid, sulfuric acid, nitric acid and phosphoric acid; and salts of organic acids such as acetic acid, propionic acid, lactic acid, succinic acid, tartaric acid, citric acid, benzoic acid, salicylic acid, nicotinic acid and heptagluconic acid. These salts can be easily produced by a conventional synthetic chemical technique.

Since the phenylazole compounds of the present invention have an antioxidation action, the phenylazole compounds can inhibit the onset and progression of lesion of arteriosclerosis by preventing oxidative denaturation of low density lipoprotein (hereinafter abbreviated to LDL) and can be applied to a therapeutic agent for arteriosclerosis, and also useful as therapeutic agents for various diseases ascribable to oxidation, for example, senile dementing diseases, cardiac disease, cancer, diabetes mellitus, digestive organ diseases, burn, ophthalmic diseases and kidney diseases. In ischemic organopathies such as cerebral infarction and myocardial infarction, various active oxygens are generated on blood reperfusion of the ischemia site and tissue disorder is aggravated by cellular membrane disruption due to the lipid peroxidation reaction. However, the phenylazole compounds of the present invention can remove various active oxygens and lipid peroxidations by the antioxidation activity, and thus the phenylazole compounds can prevent tissue disorder of the ischemic lesioned part and can be applied as a therapeutic agent for ischemic organopathy. The phenylazole compounds of the present invention have an lipoxygenase inhibitory action and a 20-HETE synthase inhibitory action, and can inhibit conversion of arachidonic acid into HPETE by inhibiting an action of lipoxygenase and can inhibit the production of 20-HETE by inhibiting 20-HETE synthase. The compounds of the present invention also include compounds which exert less dopamine release inhibitory action and hardly cause side effects such as parkinsonism.

Furthermore, the phenylazole compounds of the present invention can be used for prophylaxis and treatment of diseases caused by retinal oxidative damage; connective tissue diseases such as diabetes mellitus, hypertension, arteriosclerosis, anemia, leukemia, generalized lupus erythematosus and scleroderma; vascular damage and pro-inflammatory and denaturation lesion of the retina caused by systematic diseases such as inborn error of metabolism, for example, Tay-Sacks and Vogt-Spielmeyer; disorders of retinal vessel, such as prematurity retinopathy, occlusion of retinal vein, occlusion of retinal artery and periphlebitis retinae; inflammation and denaturation of the retina caused by retinodialysis and external injury; degenerative diseases of the retina caused by aging, such as aging macular degeneration; and diseases of the retinal focus, such as congenital retinal degeneration diseases, and are particularly useful as an aging macular degeneration occurred by photooxidation disorder; and therapeutic agents for diabetic retinopathy.

(Antioxidants)

The antioxidants of the present invention are not specifically limited as far as they contain one or more phenylazole compounds having the above antioxidation action of the present invention or pharmaceutically acceptable salts thereof as the active ingredient, and can be administered as drugs for the above diseases in any form. For example, the antioxidants can be orally, pernasally, parenterally, locally, percutaneously or transrectally administered in the dosage form of solid, semi-solid, lyophilized powder or liquid, for example, tablets, suppositories, pills, ointments, hard capsules, powders, solutions, injections, suspensions, aerosols, and sustained-release preparations, and can be in suitable dosage which can be administered simply in an accurate dose.

The antioxidants of the present invention can be formed into a composition which contains the active ingredient, a conventional carrier or excipient for drug, other drugs and an adjuvant as far as these components do not react with other components. Such a composition contains 1 to 99% by weight of the active ingredient and 99 to 1% by weight of a suitable carrier or excipient for drug, and preferably contains 5 to 75% by weight of the active ingredient and balance of a suitable carrier or excipient for drug, according to the administration mode.

To the antioxidants of the present invention, a small amount of adjuvants such as wetting agents, emulsifiers, pH buffering agents and antioxidizing agent, for example, citric acid, sorbitan monolaurate, triethanolamine oleate and butylated hydroxytoluene can be optionally added as far as these adjuvants do not react with other components, regardless of the dosage form.

These pharmaceutical preparations can be produced by a conventional process according to the description taught in Remington's Pharmaceutical Sciences, 18th edition, Mack Publishing Company, Easton, Pa., published in 1990.

In the antioxidants of the present invention, a therapeutically effective amount of the compounds represented by the formula (1) or pharmaceutically acceptable salts thereof varies depending on individuals and pathological conditions of diseases to be treated. Usually, a therapeutically dose per day of one or more compounds represented by the formula (1) or pharmaceutically acceptable salts thereof is within a range from 0.14 to 14.3 mg/day/body weight (kg), preferably from 0.7 mg to 10 mg/day/body weight (kg), more preferably from 1.4 mg to 7.2 mg/day/body weight (kg). In case of administering to the human having a body weight of 70 kg, the dose of the compounds of the formula (1) or pharmaceutically acceptable salts thereof is within a range from 10 mg to 1.0 g per day, preferably from 50 mg to 700 mg per day, and more preferably from 100 mg to 500 mg per day. This dose is merely a measure and can deviate from the above range according to the pathological conditions of the treatment.

Preferable administration path of the antioxidants of the present invention is oral administration and examples of the excipient to be applied to the antioxidants for oral administration include conventionally used any excipients, for example, mannitol, lactose, starch, gelatinized starch, magnesium stearate, saccharin sodium, talc, cellulose ether derivative, glucose, gelatin, sucrose, citrate and propyl gallate which are used for drugs. The antioxidants for oral administration can contain diluents such as lactose, sucrose and dicalcium phosphate, disintegrators such as croscarmellose sodium or derivative thereof, and binders such as magnesium stearate, lubricants such as starch, gum arabic, polyvinyl pyrrolidone, gelatin and cellulose ether derivative.

When the antioxidants of the present invention are applied to the injection, sterile aqueous or non-aqueous solutions, suspensions and emulsions are preferably contained. As the diluent of the aqueous solutions and suspensions, diluent, for example, distilled water or physiological saline for injection can be used. As the diluent of the water-insoluble solutions and suspensions, for example, propylene glycol, polyethylene glycol, vegetable oil such as olive oil, alcohols such as ethanol, and Polysolvate (trade name) can be used. The injections may further contain additives such as isotonizing agents, antiseptics, wetting agents, emulsifiers, dispersing agent, stabilizers (for example, lactose), solubilizers and solubilizing auxiliary agents. These additives can also be used by dissolving in sterile water or a sterile solvent for injection after producing a solid composition of a filter material and a sterilizer which pass through a bacteria holding filter.

When the antioxidants of the present invention are applied to the suppository, the suppository is obtained by using, as a carrier, a carrier which gradually dissolves in the body such as polyoxyethylene glycol or polyethylene glycol (hereinafter abbreviated to PEG), for example, PEG1000 (96%) or PEG4000 (4%) and dispersing 0.5 to 50% by weight of the compounds of the formula (1) or pharmaceutically acceptable salts thereof in the carrier.

When the antioxidants of the present invention are applied to the solution, the solution is preferably obtained by using, as a carrier, water, saline, aqueous dextrose solution, glycerol or ethanol, and dispersing 0.5 to 50% by weight of the compounds of the formula (1) or pharmaceutically acceptable salts thereof and any adjuvant for drug in the carrier to give a solution or suspension.

(Retinal Oxidative Damage Inhibitors)

The retinal oxidative damage inhibitors of the present invention are not specifically limited as far as they contain the antioxidants containing the phenylazole compounds having the antioxidation action or pharmaceutically acceptable salts thereof of the present invention as the active ingredient, and the administration mode, the dosage form and the dose may be the same as those in case of the antioxidants. The retinal oxidative damage inhibitors can contain the same components for preparation, carriers and adjuvant as those in case of the antioxidants and may further contain excipients, disintegrators, binders and one or more retinal oxidative damage inhibitors which do not react with the active ingredients, and also may contain components having other drug potency. The dosage form may be the same as those in case of the antioxidants, and may be the other dosage form such as eye drop or eye ointment.

When the retinal oxidative damage inhibitors of the present invention are applied to the eye drop, the phenylazole compounds of the present invention are added to a base solvent used usually to give an aqueous solution or suspension and then the pH is adjusted within a range from 4 to 10, and preferably from 5 to 9. The eye drop is preferably subjected to a sterilization treatment so as to obtain a sterile product, and the sterilization treatment can be carried out in any stage of the production process. The concentration of the phenylazole compounds of the present invention in the eye drop is within a range from 0.001 to 3% (W/V), and preferably from 0.01 to 1% (W/V). The dose varies depending on the degree of symptoms and constitution of patients and the eye drop may be applied 1 to 4 times per day in an amount of several drops. This dose is merely a measure and can deviate from the above range according to the pathological conditions of the treatment.

To the eye drop, various additives such as buffering agents, isotonizing agents, antiseptics, pH adjustors, thickeners, chelating agents and, solubilizing agents may be appropriately added as far as these components do not react with phenylazole compounds of the present invention. Examples of the buffering agent include citrate buffering agent, tartaric acid buffering agent, acetate buffering agent and amino acid. Examples of the isotonizing agent include saccharides such as sorbitol, glucose and mannitol, polyhydric alcohols such as glycerin, polyethylene glycol and propylene glycol, and salts such as sodium chloride. Examples of the antiseptic include paraoxybenzoate esters such as methyl paraoxybenzoate and ethyl paraoxybenzoate, benzyl alcohol, phenethyl alcohol, sorbic acid or salts thereof. Examples of the pH adjustor include phosphoric acid and sodium hydroxide. Examples of the thickener include hydroxyethyl cellulose, hydroxypropyl cellulose, methyl cellulose, hydroxypropylmethyl cellulose, carboxymethyl cellulose and salts thereof. Examples of the chelating agent include sodium edetate, sodium citrate and condensed sodium phosphate, and examples of the solubilizing agent include ethanol and polyoxyethylene hardened castor oil.

When the retinal oxidative damage inhibitors of the present invention are applied to the eye ointment, the eye ointment is obtained by mixing the phenylazole compounds of the present invention with an eye ointment base such as purified lanolin, white petrolatum, macrogol, plastibase or liquid paraffin, and is preferably subjected to a sterilization treatment so as to obtain a sterile product. The concentration of the phenylazole compounds of the present invention in the eye ointment is within a range from 0.001 to 3% (W/V), and preferably from 0.01 to 1% (W/V). The dose varies depending on the degree of symptoms and constitution of patients and the eye ointment may be applied 1 to 4 times per day. This dose is merely a measure and can deviate from the above range according to the pathological conditions of the treatment.

The retinal oxidative damage inhibitors of the present invention have an excellent antioxidation action and are therefore effective to prophylaxis and treatment for degenerative disease of the retina caused by aging, such as aging macular degeneration and diabetic retinopathy.

Lipoxygenase inhibitors, 20-hydroeicosatetraenoic acid (20-HETE) synthase inhibitors and therapeutic agents for kidney diseases, cerebrovascular or circulatory diseases, or cerebral infarction of the present invention are not specifically limited as far as they contain the antioxidants containing one or more phenylazole compounds having the antioxidation action or pharmaceutically acceptable salts thereof of the present invention as the active ingredient, and the administration mode, the dosage form and the dose may be the same as those in case of the antioxidants. They can contain the same components for preparation, carriers and adjuvants as those in case of the antioxidants and may further contain excipients, disintegrators, binders and one or more retinal oxidative damage inhibitors which do not react with the active ingredients, and also may contain components having other drug potency. The dosage form may be the same as those in case of the antioxidants.

The phenylazole compounds of the present invention will now be described in detail by way of examples, but the technical scope of the present invention is not limited to these examples.

EXAMPLE 1

[Step 1]

Production of
1-acetyl-4-(4-imidazol-1-ylphenyl)-piperazine

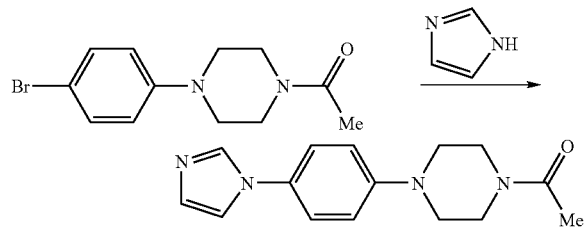

To a reaction solution prepared by dissolving 20 g of 1-acetyl-4-(4-bromophenyl)-piperazine and 7.9 g of imidazole in 120 ml of xylene, 16.9 g of 1,10-phenanthroline, 1.4 g of 1,5-diphenyl-1,4-pentadien-3-one, 28.9 g of cesium carbonate and 1.8 g of a copper (I) trifluoromethanesulfonate benzene complex, as a catalyst, were added at room temperature, followed by heating at reflux in an argon gas flow at 125° C. for 24 hours. After the completion of the reaction, the reaction solution was mixed with 300 ml of an aqueous ammonium solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:ethyl acetate=3:1→chloroform:methanol=20:1) to obtain 15.2 g of the objective 1-acetyl-4-(4-imidazol-1-ylphenyl)-piperazine (melting point: 181-182° C.).

Production of 1-(4-imidazol-1-ylphenyl)-piperazine

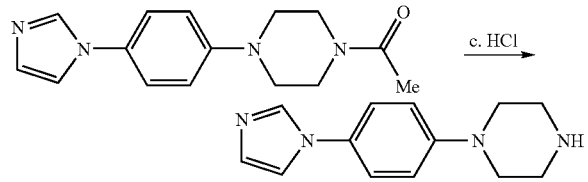

To 15.2 g of 1-acetyl-4-(4-imidazol-1-ylphenyl)-piperazine, 100 ml of concentrated hydrochloric acid was added, followed by heating at reflux for 3 hours. After the completion of the reaction, the reaction solution was cooled and then neutralized with an aqueous 1N sodium hydroxide solution, thereby to precipitate a crystal. The resulting crystal was filtrated, washed with a small amount of water and then dried to obtain 12 g of the objective 1-(4-imidazol-1-ylphenyl)-piperazine (melting point: 177-180° C.).

Production of 4-(±)-(5-nitro-2,4,6,7-tetramethyldihydrobenzofuran-2-ylmethyl)-1-(4-imidazol-1-ylphenyl)piperazine

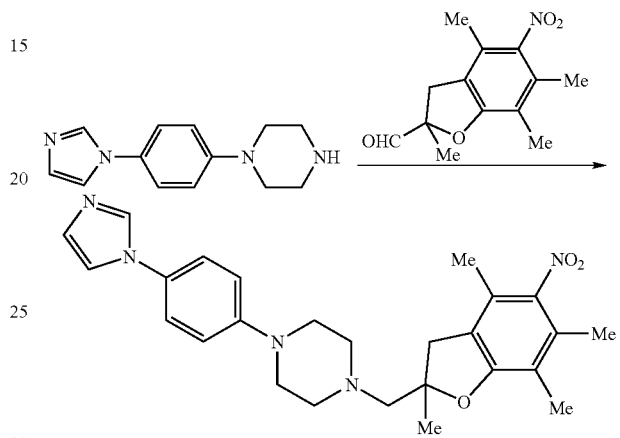

0.7 g of 1-(4-imidazol-1-ylphenyl)-piperazine and 0.7 g of 2,4,6,7-tetramethyl-5-nitrodihydrobenzofuran-2-aldehyde were dissolved in 20 ml of methylene chloride and 1 ml of acetic acid as a catalyst was added, followed by stirring at room temperature for 30 minutes. To the resulting reaction solution, 1.2 g of sodium triacetoxyborohydride was added, followed by stirring at room temperature for 30 minutes. After the completion of the reaction, the reaction solution was poured into water, neutralized with an aqueous saturated sodium hydrogen carbonate solution and then extracted with chloroform. The organic layer was washed with saturated saline and then dried over anhydrous magnesium sulfate. After removing magnesium sulfate by filtration and concentrating under reduced pressure, 1.3 g of the objective product was obtained.

EXAMPLE 2

[Step 2]

Production of 4-(±)-(5-amino-2,4,6,7-tetramethyldihydrobenzofuran-2-ylmethyl)-1-(4-imidazol-1-ylphenyl)piperazine

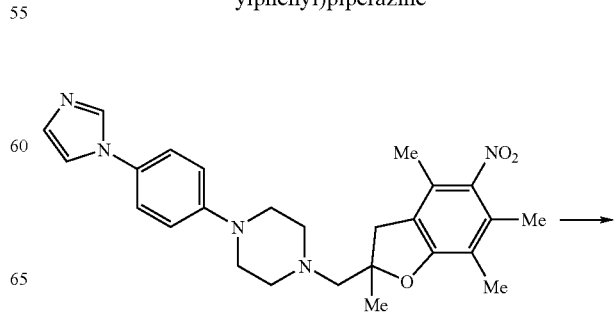

-continued

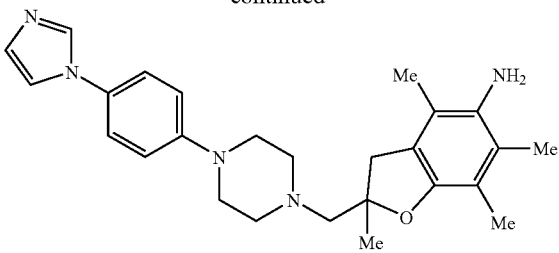

To 1.3 g of 4-(±)-(5-nitro-2,4,6,7-tetramethyldihydrobenzofuran-2-ylmethyl)-1-(4-imidazol-1-ylphenyl)piperazine, 30 ml of ethanol was added and 4.4 g of stannous chloride-dihydrate and 15 ml of concentrated hydrochloric acid were added, followed by heating at reflux for 6 hours. The reaction solution was poured into water, neutralized with a 1N sodium hydroxide solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:methanol=30:1) to obtain 0.5 g of the objective product (melting point: 165-167° C.).

EXAMPLE 3

[Step 1]

Production of (±)-(5-nitro-2,4,6,7-tetramethyldihydrobenzofuran-2-yl)-[4-(4-imidazol-1-ylphenyl)-piperazin-1-yl]carboxamide

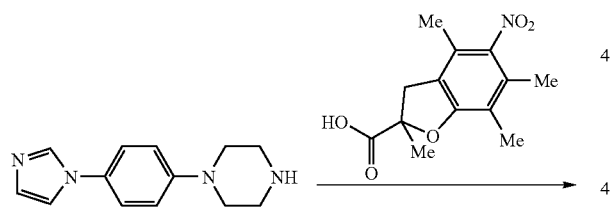

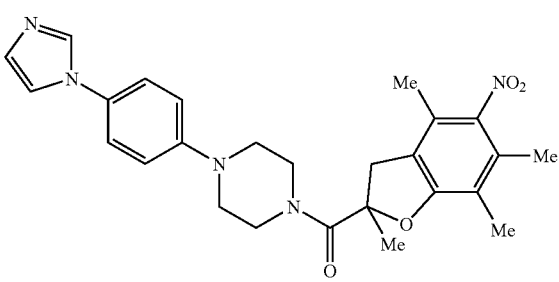

To 0.43 g of 1-(4-imidazol-1-ylphenyl)-piperazine and 0.5 g of 2,4,6,7-tetramethyl-5-nitrodihydrobenzofuran-2-carboxylic acid, 0.44 g of 1-(3-dimethylaminopropyl)-3-ethyl-carbodiimide hydrochloride, 0.31 g of 1-hydroxybenzotriazole hydrochloride and 0.23 g of triethylamine were added, followed by stirring at room temperature for 24 hours. The reaction solution was poured into water and the precipitated crystal was removed by filtration and washed with water and ether, and then the resulting crystal was dried to obtain 0.88 g of the objective compound.

EXAMPLE 4

[Step 2]

Production of (±)-(5-amino-2,4,6,7-tetramethyldihydrobenzofuran-2-yl)-[4-(4-imidazol-1-ylphenyl)-piperazin-1-yl]carboxamide

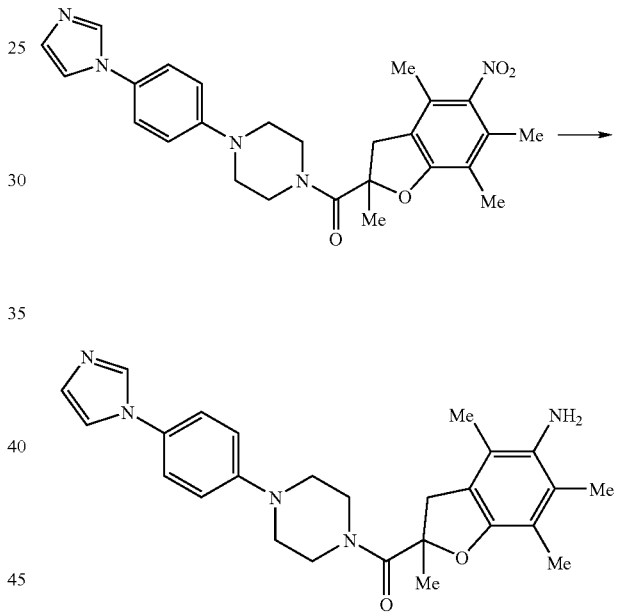

In an autoclave, 0.88 g of (±)-(5-nitro-2,4,6,7-tetramethyldihydrobenzofuran-2-yl)-[4-(4-imidazol-1-ylphenyl)-piperazin-1-yl]carboxamide and 0.5 g of 10% palladium carbon, 10 ml of ethanol and 5 ml of acetic acid were added, followed by stirring overnight under a hydrogen pressure of 10 kg/cm$^2$. The reaction solution was poured into water, neutralized with a 1N sodium hydroxide solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:methanol=10:1) to obtain 0.56 g of the objective product (melting point: 189-191° C.).

A 3-imidazole compound could be synthesized by the same process.

EXAMPLE 5

[Step 1]

Production of 1-[4-(4-acetyl-piperazin-1-yl)-phenyl]-3-dimethylaminopropenone

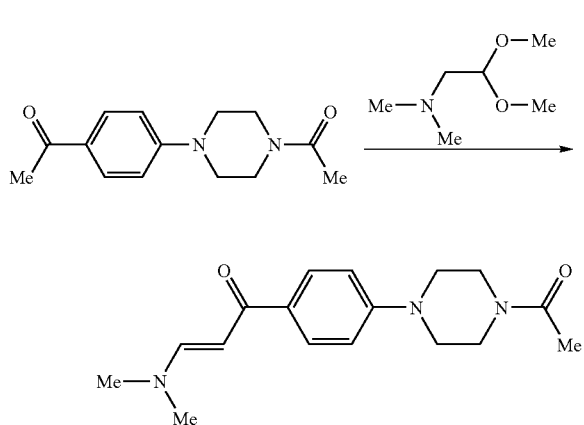

5.7 g of 1-acetyl-4-(4-acetylphenyl)-piperazine and 24 ml of dimethylaminoacetaldehydehyde dimethylacetal were dissolved in 25 ml of xylene, followed by heating at reflux for 18 hours while removing methanol. After the completion of the reaction, the reaction solution was cooled, thereby to precipitate a crystal, which was washed with ether-hexane (=10:1) to obtain 6.3 g of the objective 1-[4-(4-acetyl-piperazin-1-yl)-phenyl]-3-dimethylaminopropenone.

Production of 1-acetyl-4-(4-1H-pyrazol-5-ylphenyl)-piperazine

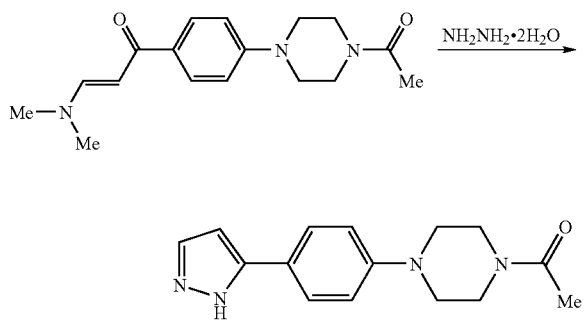

6.3 g of 1-[4-(4-acetyl-piperazin-1-yl)-phenyl]-3-dimethylaminopropenone and 1.6 g of hydrazine hydrate were dissolved in 50 ml of ethanol and 0.3 g of p-toluenesulfonic acid as a catalyst was added, followed by heating at reflux for one hour. After the completion of the reaction, the reaction solution was cooled, thereby to precipitate a crystal, which was washed with ether to obtain 5.1 g of the objective 1-acetyl-4-(4-1H-pyrazol-5-ylphenyl)-piperazine (melting point: 257-259° C.).

Production of 1-(4-1H-pyrazol-5-ylphenyl)-piperazine

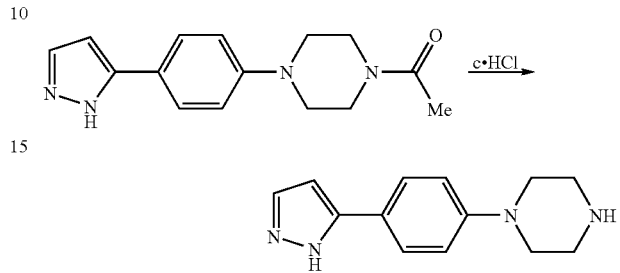

To 5.1 g of 1-acetyl-4-(4-1H-pyrazol-5-ylphenyl)-piperazine, 60 ml of concentrated hydrochloric acid were added, followed by heating at reflux for 3 hours. After the completion of the reaction, the reaction solution was cooled and then neutralized with an aqueous 1N sodium hydroxide solution, thereby to precipitate a crystal. The resulting crystal was filtered, washed with a small amount of water and then dried to obtain 4.3 g of the objective 1-(4-1H-pyrazol-5-ylphenyl)-piperazine (melting point: 290° C. or higher).

Production of (±)-(5-nitro-2,4,6,7-tetramethyldihydrobenzofuran-2-yl)-[4-(4-1H-pyrazol-5-ylphenyl)-piperazin-1-yl]carboxamide

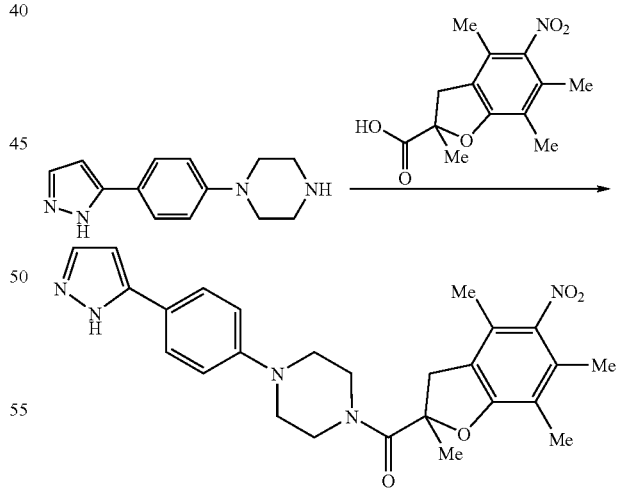

To 0.38 g of 1-(4-1H-pyrazol-5-ylphenyl)-piperazine and 0.4 g of 2,4,6,7-tetramethyl-5-nitrodihydrobenzofuran-2-carboxylic acid, 0.35 g of 1-(3-dimethylaminopropyl)-3-ethylcarbodiimide hydrochloride, 0.25 g of 1-hydroxybenzotriazole hydrochloride and 0.19 g of triethylamine were added, followed by stirring at room temperature for 24 hours. The reaction solution was poured into water and the precipitated crystal was removed by filtration and washed with water, and then the resulting crystal was dried to obtain 0.65 g of the objective compound.

EXAMPLE 6

[Step 2]

Production of (±)-(5-amino-2,4,6,7-tetramethyldihydrobenzofuran-2-yl)-[4-(4-1H-pyrazol-5-ylphenyl)-piperazin-1-yl]carboxamide

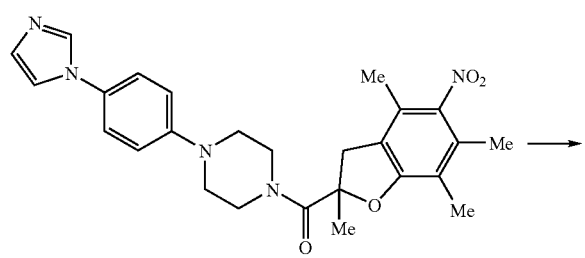

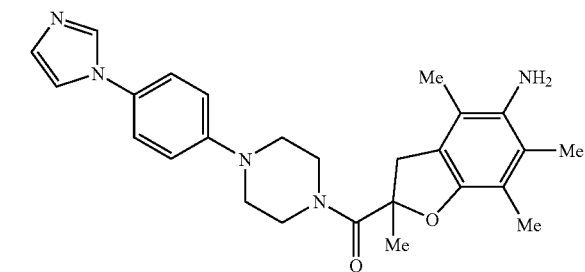

In an autoclave, to 0.65 g of (±)-(5-nitro-2,4,6,7-tetramethyldihydrobenzofuran-2-yl)-[4-(4-1H-pyrazole-phenyl)-piperazin-1-yl]carboxamide and 0.2 g of 10% palladium carbon, 5 ml of ethanol and 5 ml of acetic acid were added, followed by stirring under a hydrogen pressure of 10 kg/cm$^2$ for 2 days. The reaction solution was poured into water, neutralized with a 1N sodium hydroxide solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:methanol=10:1) to obtain 0.25 g of the objective product (melting point: 128-130° C.).

3-1H-pyrazole compound could be synthesized by the same process.

EXAMPLE 7

[Step 1]

Production of 1-acetyl-4-(4-imidazol-1-ylphenyl)-4-hydroxypiperidine

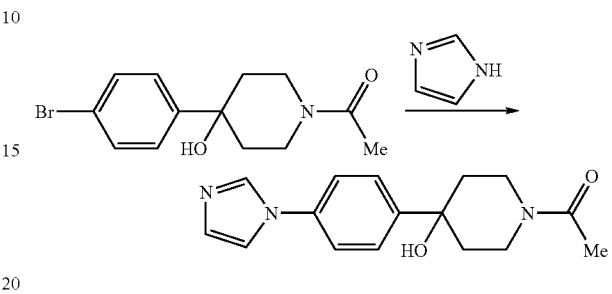

To a reaction solution prepared by suspending 3 g of 1-acetyl-4-(4-bromophenyl)-4-hydroxypiperidine and 1.1 g of imidazole in 18 ml of xylene, 2.4 g of 1,10-phenanthroline, 0.2 g of 1,5-diphenyl-1,4-pentadien-3-one, 4.3 g of cesium carbonate and 0.3 g of a copper (I) trifluoromethanesulfonate benzene complex, as a catalyst, were added at room temperature, followed by heating at reflux in an argon gas flow at 125° C. for 24 hours. After the completion of the reaction, the reaction solution was mixed with 50 ml of an aqueous ammonium chloride solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:ethyl acetate=3:1→chloroform:methanol=20:1) to obtain 2.5 g of the objective 1-acetyl-4-(4-imidazol-1-yl-phenyl)-4-hydroxypiperidine.

Production of 4-(4-imidazol-1-ylphenyl)-1,2,3,6-tetrahydropyridine

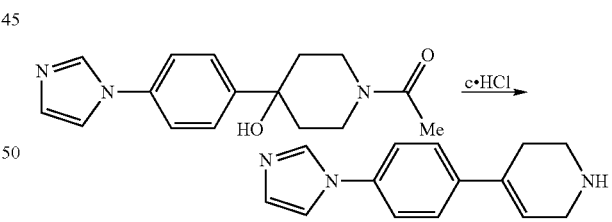

To 2.5 g of 1-acetyl-4-(4-imidazol-1-ylphenyl)-4-hydroxypiperidine, 30 ml of concentrated hydrochloric acid was added, followed by heating at reflux for 4 hours. After the completion of the reaction, the reaction solution was cooled, neutralized with an aqueous 1N sodium hydroxide solution and then extracted with chloroform. The organic layer was washed with saturated saline and then dried over dried over anhydrous magnesium sulfate. After removing magnesium sulfate by filtration and concentrating under reduced pressure, the resulting crystal was washed with hexane and then dried to obtain 1.5 g of the objective 4-(4-imidazol-1-ylphenyl)-1,2,3,6-tetrahydropyridine (mp: 150-153° C.).

EXAMPLE 8

[Step 2]

Production of 2,4,6,7-tetramethyl-5-nitrodihydrobenzofuran-2-trifluoromethanesulfonate

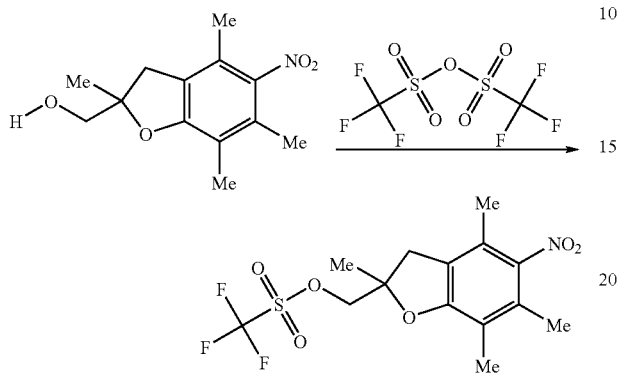

6.7 g of trifluoromethanesulfonic acid anhydride was dissolved in 50 ml of dichloromethane, followed by cooling to 0° C. In the solution, a solution prepared by dissolving 5.0 g of 2-hydroxymethyl-2,4,6,7-tetramethyldihydrobenzofuran in 50 ml of dichloromethane and 2.4 g of triethylamine were added dropwise over 30 minutes. After the dropwise addition and stirring at 0° C. for one hour, the temperature was raised to room temperature, followed by stirring for 1.5 hours. After the reaction, the reaction solution was washed with water and dried over anhydrous magnesium sulfate, and then the solvent was distilled off under reduced pressure. The residue was subjected to silica gel column chromatography (chloroform:methanol=100:1) to obtain 7.3 g of the objective product.

EXAMPLE 9

[Step 2]

Production of 4-(±)-(5-nitro-2,4,6,7-tetramethyldihydrobenzofuran-2-ylmethyl)-1-(4-imidazol-1-ylphenyl)-1,2,3,6-tetrahydropyridine

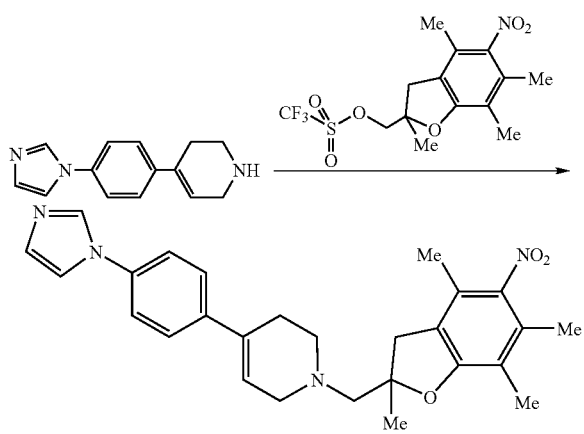

0.7 g of 4-(4-imidazol-1-ylphenyl)-1,2,3,6-tetrahydropyridine and 1.2 g of 2,4,6,7-tetramethyl-5-nitrodihydrobenzofuran-2-trifluoromethanesulfonate were dissolved in 30 ml of acetonitrile and 0.35 g of sodium carbonate was added, followed by heating at reflux for 24 hours. After the completion of the reaction, the reaction solution was poured into water and then extracted with chloroform. The organic layer was washed with saturated saline and then dried over anhydrous magnesium sulfate. After removing magnesium sulfate by filtration and concentrating under reduced pressure, 1.2 g of the objective product was obtained.

EXAMPLE 10

[Step 3]

Production of 4-(±)-(5-amino-2,4,6,7-tetramethyldihydrobenzofuran-2-ylmethyl)-1-(4-imidazol-1-ylphenyl)-1,2,3,6-tetrahydropyridine

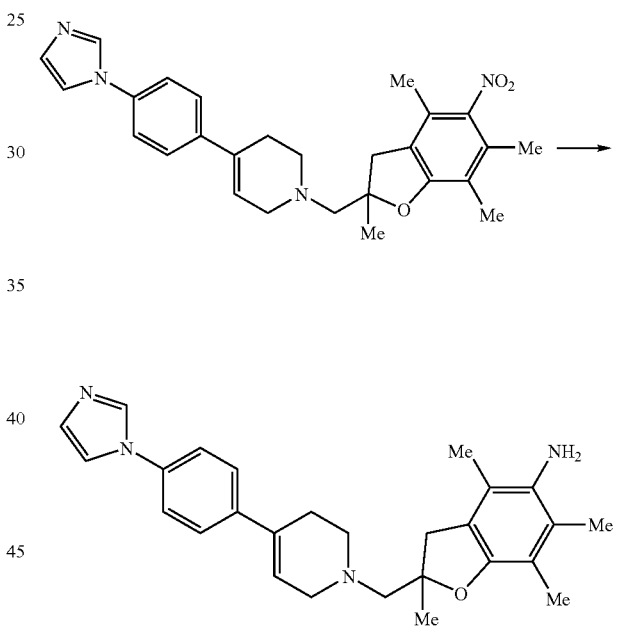

To 1.2 g of 4-(±)-(5-nitro-2,4,6,7-tetramethyldihydrobenzofuran-2-ylmethyl)-1-(4-imidazol-1-ylphenyl)-1,2,3,6-tetrahydropyridine, 30 ml of ethanol was added and 3.6 g of stannous chloride-dihydrate and 15 ml of concentrated hydrochloric acid were added, followed by heating at reflux for 8 hours. The reaction solution was poured into water, neutralized with a 1N sodium hydroxide solution and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (chloroform:methanol=20:1) to obtain 0.93 g of the objective product (mp: 161-163° C.).

EXAMPLE 11

Production of 4-(±)-(5-amino-2,4,6,7-tetramethyldihydrobenzofuran-2-ylmethyl)-1-(4-imidazol-1-ylphenyl)piperidine

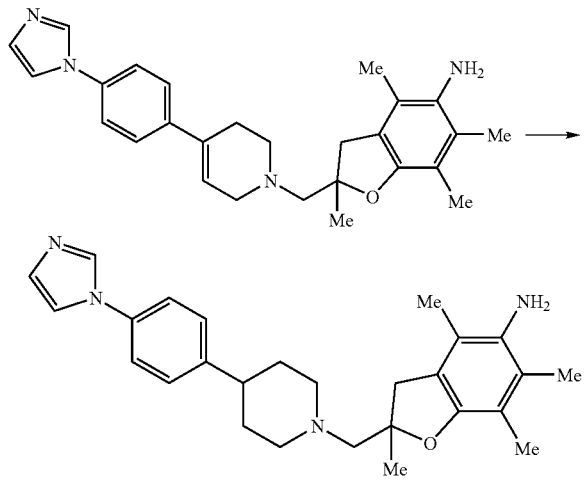

In an autoclave, to 0.45 g of 4-(±)-(5-amino-2,4,6,7-tetramethyldihydrobenzofuran-2-ylmethyl)-1-(4-imidazol-1-ylphenyl)-1,2,3,6-tetrahydropyridine and 0.1 g of 10% palladium carbon, 5 ml of ethanol and 5 ml of acetic acid were added, followed by stirring at 50° C. under a hydrogen pressure of 10 kg/cm² for 7 hours. The reaction solution was poured into water, neutralized with 1N sodium hydroxide solution and then extracted with chloroform. The organic layer was washed with saturated saline and then dried over anhydrous magnesium sulfate. After removing magnesium sulfate by filtration and concentrating under reduced pressure, the resulting crystal was washed with hexane and then dried to obtain 0.39 g of the objective product (mp: 170-172° C.).

A 3-imidazole compound can be synthesized by the same process. Also an amide type compound can be synthesized by the same process.

EXAMPLE 12

Step 1: Production of 4-(±)-(5-nitro-2,4,6,7-tetramethyldihydrobenzofuran-2-ylmethyl)aminophenyl-1-imidazole

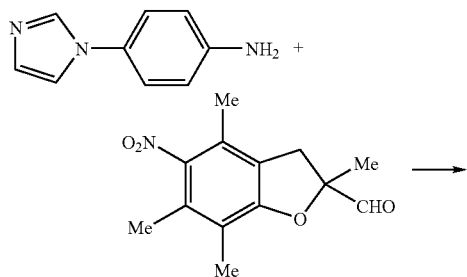

-continued

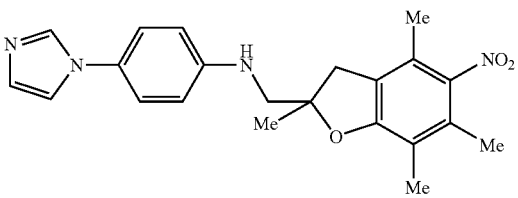

1.7 g of 1-(4-aminophenyl)imidazole and 1.09 g of 2,4,6,7-tetramethyl-5-nitrodihydrobenzofuran-2-aldehyde were dissolved in 53 ml of methylene chloride and 0.8 ml of acetic acid was added, followed by stirring at room temperature for 10 minutes. To the resulting reaction solution, 2.91 g of sodium triacetoxyborohydride was added, followed by stirring overnight at room temperature. After the completion of the reaction, the reaction solution was poured into water, neutralized with an aqueous sodium hydroxide solution and then extracted with chloroform. The organic layer was washed with saturated saline and dried over anhydrous magnesium sulfate, and then the solvent was concentrated under reduced pressure. The residue was purified by silica gel column chromatography (chloroform:methanol=100:3) to obtain 1.2 g of the objective product.

Step 2: Production of 4-(±)-(5-amino-2,4,6,7-tetramethyldihydrobenzofuran-2-ylmethyl)aminophenyl-1-imidazole

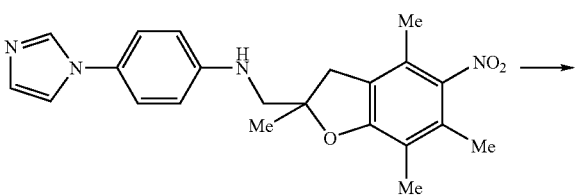

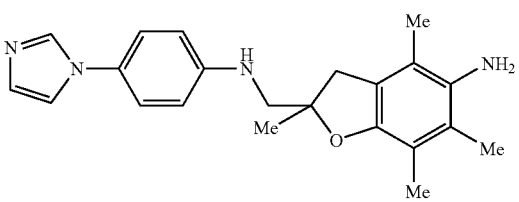

To 0.93 g of 4-(±)-(5-nitro-2,4,6,7-tetramethyldihydrobenzofuran-2-ylmethyl)aminophenylimidazole and 0.5 g of 20% palladium hydroxide on carbon, 10 ml of acetic acid was added, followed by stirring overnight at 50° C. under a hydrogen pressure of 10 Kg/cm². The reaction solution was filtered through celite and the filtrate was concentrated under reduced pressure, and then the residue was purified by silica gel column chromatography (chloroform:methanol=20:1) to obtain 0.57 g of the objective product (refractive index nD20.4 1.5693)

EXAMPLE 13

Step 1: Production of 5-(4-(±)-(5-nitro-2,4,6,7-tetramethyldihydrobenzofuran-2-ylmethyl)aminophenyl)pyrazole

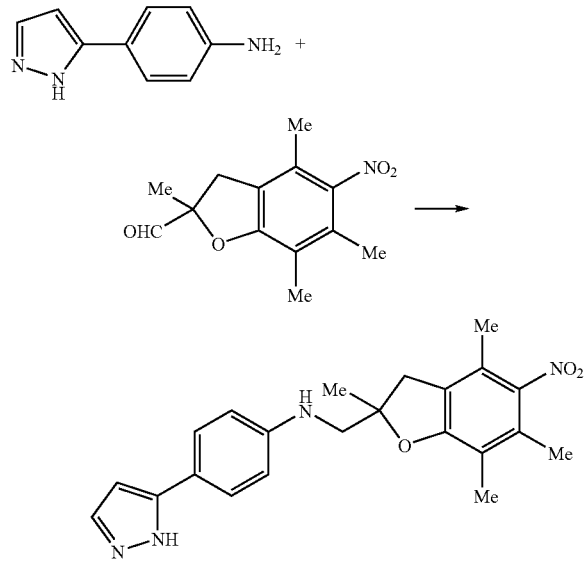

0.77 g of 5-(4-aminophenyl)pyrazole and 1.00 g of 2,4,6,7-tetramethyl-5-nitrodihydrobenzofuran-2-aldehyde were dissolved in 33 ml of methylene chloride and 0.5 ml of acetic acid was added, followed by stirring at room temperature for 30 minutes. To the resulting reaction solution, 1.70 g of sodium triacetoxyborohydride was added, followed by stirring at room temperature for 20 hours. After the completion of the reaction, the reaction solution was poured into water, neutralized with an aqueous sodium hydroxide solution and then extracted with chloroform. The organic layer was washed with hydrochloric acid water, neutralized with an aqueous sodium hydroxide solution, and then the organic layer was washed with saturated saline and dried over anhydrous magnesium sulfate. The solvent was concentrated under reduced pressure to obtain 1.5 g of the objective product.

Step 2: Production of 3(5)-(4-(±)-(5-nitro-2,4,6,7-tetramethyldihydrobenzofuran-2-ylmethyl)aminophenyl)-1-(tetrahydropyran-2-yl)pyrazole

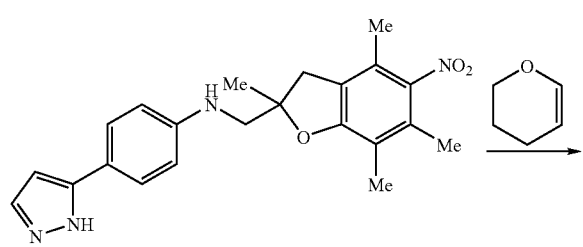

-continued

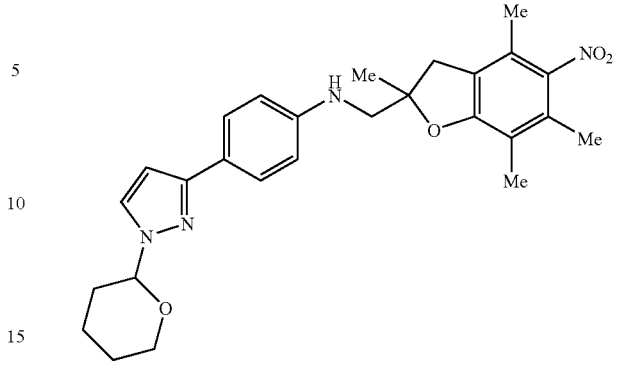

0.50 g of 5-(4-(±)-(5-nitro-2,4,6,7-tetramethyldihydrobenzofuran-2-ylmethyl)aminophenyl)pyrazole and 0.01 g of p-toluenesulfonic acid hydrate were dissolved in 2 ml of ethyl acetate and then heated to 50° C. In the solution, a solution prepared by dissolving 0.13 g of 3,4-dihydro-2H pyran in 2 ml of ethyl acetate was added dropwise over 30 minutes, followed by stirring at 55° C. for 10 hours. The reaction solution was cooled, washed with 2 ml of 3N ammonia water and then washed until the pH of the organic layer reaches 7. The organic layer was dried over anhydrous magnesium sulfate and the solvent was distilled off, and then residue was purified by silica gel column chromatography (chloroform:methanol=50:1) to obtain 0.60 g of the objective product.

Step 3: Production of 3(5)-(4-(±)-(5-nitro-2,4,6,7-tetramethyldihydrobenzofuran-2-ylmethyl)methylaminophenyl)-1-(tetrahydropyran-2-yl)pyrazole

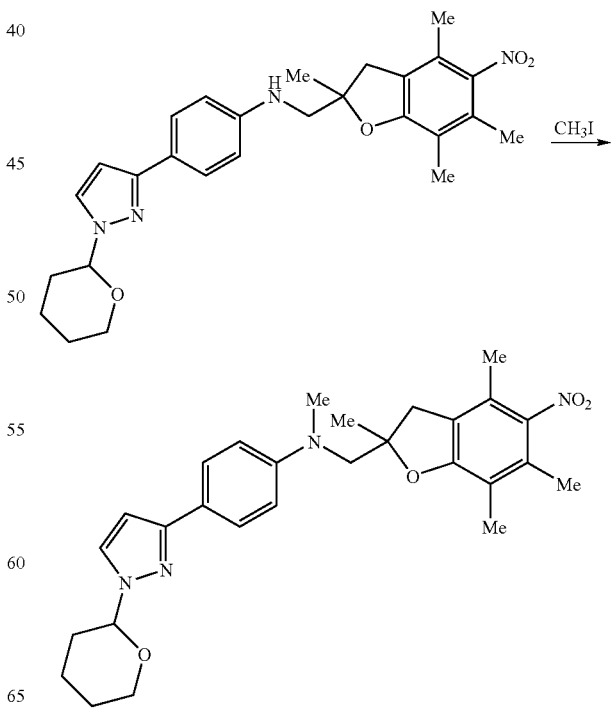

0.23 g of 3(5)-(4-(±)-(5-nitro-2,4,6,7-tetramethyldihydrobenzofuran-2-ylmethyl)aminophenyl)-1-(tetrahydropyran-2-yl)pyrazole, 1 m of methyl iodide and 0.08 g of potassium carbonate were dissolved in 5 ml of acetonitrile, followed by heating at reflux for 3 hours. After the concentration, addition of chloroform and filtration, the filtrate was concentrated, the residue was purified by silica gel column chromatography (hexane:ethyl acetate=3:2) to obtain 0.14 g of the objective product.

Step 4: Production of 5-(4-(±)-(5-nitro-2,4,6,7-tetramethyldihydrobenzofuran-2-ylmethyl)methylaminophenyl)pyrazole

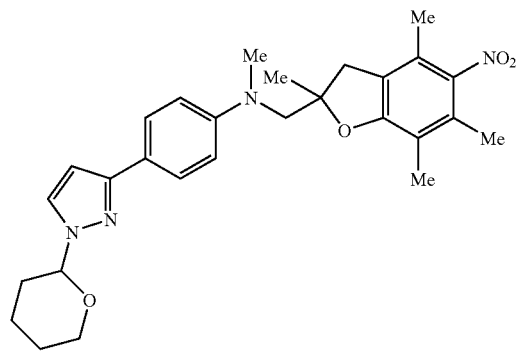

0.32 g of 3(5)-(4-(±)-(5-nitro-2,4,6,7-tetramethyldihydrobenzofuran-2-ylmethyl)methylaminophenyl)-1-(tetrahydropyran-2-yl)pyrazole was dissolved in 30 ml of dry methylene chloride, followed by cooling to 5° C. A hydrogen chloride gas was bubbled into the solution for 5 minutes, followed by stirring at room temperature for 6 hours and further standing for 11 hours. The reaction solution was neutralized with an aqueous sodium hydroxide solution, extracted with chloroform, washed with saturated saline and dried over anhydrous magnesium sulfate, and then the solvent was distilled off. The residue was purified by silica gel column chromatography (chloroform:methanol=50:1) to obtain 0.26 g of the objective product.

Step 5: Production of 5-(4-(±)-(5-amino-2,4,6,7-tetramethyldihydrobenzofuran-2-ylmethyl)methylaminophenyl)pyrazole

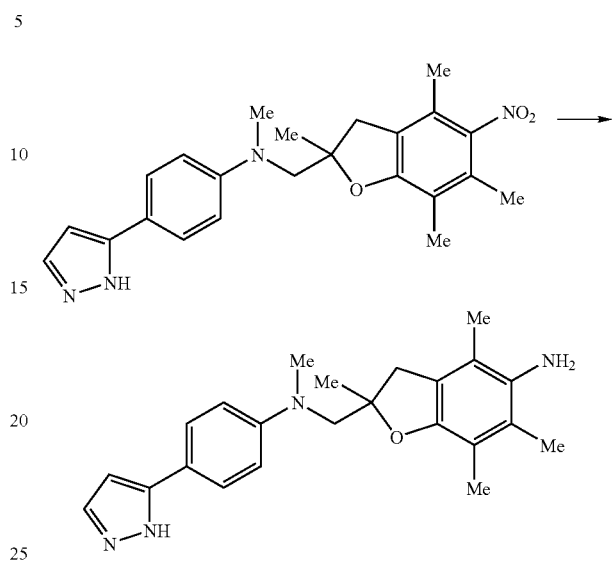

To 0.26 g of 5-(4-(±)-(5-nitro-2,4,6,7-tetramethyldihydrobenzofuran-2-ylmethyl)methylaminophenyl) pyrazole, 10 ml of ethanol was added and 0.43 g of stannous chloride dihydrate and 3 ml of concentrated hydrochloric acid were added, followed by heating at reflux for 2 hours. The reaction solution was poured into water, neutralized with a sodium hydroxide solution and then extracted with chloroform. The organic layer was washed with saturated saline, dried over anhydrous magnesium sulfate and then distilled off under reduced pressure. The residue was purified by silica gel column chromatography (chloroform:methanol=20:1) to obtain 0.22 g of the objective product (melting point: 113-117° C.)

EXAMPLE 14

Step 1: Production of 2,4,6,7-tetramethyl-5-nitrodihydrobenzofuran-2-trifluoromethanesulfonate

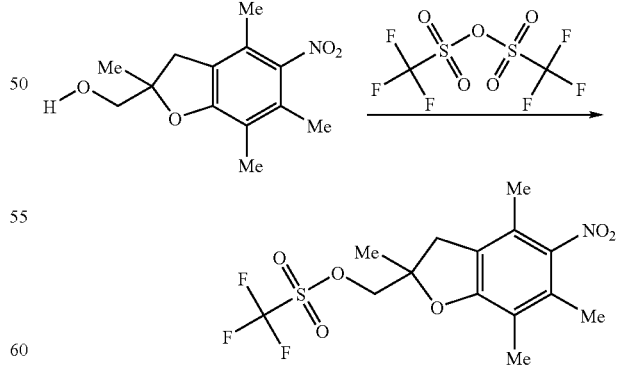

6.7 g of trifluoromethanesulfonic acid anhydride was dissolved in 50 ml of dichloromethane, followed by cooling to 0° C. In the solution, a solution prepared by dissolving 5.0 g of 2-hydroxymethyl-2,4,6,7-tetramethyldihydrobenzofuran and 2.4 g of triethylamine in 50 ml of dichloromethane was added dropwise over 30 minutes. After the dropwise addition and stirring at 0° C. for one hour, the temperature was raised to room temperature, followed by stirring for 1.5 hours. After the reaction, the reaction solution was washed with water and dried over anhydrous magnesium sulfate, and then the solvent was distilled off under reduced pressure. The residue was purified by silica gel column chromatography (chloroform:methanol=100:1) to obtain 7.3 g of the objective product.

Step 2: Production of 4-(±)-(5-nitro-2,4,6,7-tetramethyldihydrobenzofuran-2-ylmethoxy)-phenyl-1-imidazole

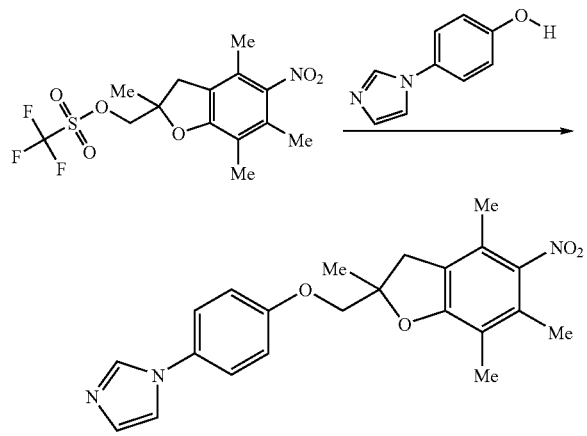

0.25 g of 4-imidazol-1-yl-phenol was dissolved in 5 ml of dimethyl formamide and 0.06 g of 60% sodium hydride was added under stirring. After stirring at room temperature for one hour, a solution prepared by dissolving 0.5 g of 2,4,6,7-tetramethyl-5-nitrodihydrobenzofuran-2-trifluoromethanesulfonate in 5 ml of DMF was added, followed by stirring at room temperature for one hour. After the reaction, the reaction solution was washed with water and dried over anhydrous magnesium sulfate, and then the solvent was distilled off under reduced pressure. The residue was allowed to stand for 4 hours and 10 ml of water was added, and then the precipitated filtered and dried with heating to obtain 0.3 g of the objective product.

Step 3: Production of 4-(±)-(5-amino-2,4,6,7-tetramethyldihydrobenzofuran-2-ylmethoxy)-phenyl-1-imidazole

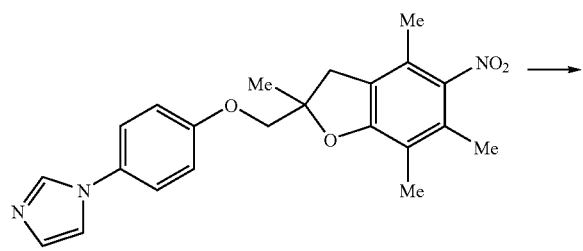

-continued

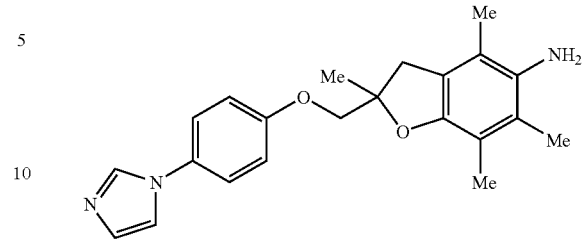

To 0.3 g of 4-(±)-(5-nitro-2,4,6,7-tetramethyldihydrobenzofuran-2-ylmethoxy)-phenyl-1-imidazole, 10 ml of ethanol was added and 0.5 g of stannous chloride dihydrate and 3 ml of concentrated hydrochloric acid were added, followed by heating at reflux for 2 hours. The reaction solution was poured into water, neutralized with a 1N sodium hydroxide solution and then extracted with chloroform. The organic layer was washed with saturated saline, dried over anhydrous magnesium sulfate and then distilled off under reduced pressure. The residue was purified by silica gel column chromatography (chloroform:methanol=50:1) to obtain 0.2 g of the objective product (melting point: 129-131° C.)

EXAMPLE 15

4-(±)-(5-amino-2,4,6,7-tetramethyldihydrobenzofuran-2-ylmethylamino)-phenyl-5-1H-pyrazole (compound B-2-5-1) was separated using a column for separation of an optical isomer CHIRALCEL OD (DAICEL CHEMICAL INDUSTRIES, LTD.) to obtain a fraction 1 effused first and a fraction 2 effused later. Each fraction was recrystallized from ethanol-water. A hydrochloride was prepared by a conventional process.

Fraction 1 retention time: 13.7 min
　(−)-(compound B-2-5-1) mp [107-110]
　$[\alpha]_D$−16.9° (C 1.01, EtOH)
　HPLC>99.9% ee
　2HCl salt melting point: 183-187° C.

Fraction 2 retention time: 27 min
　(+)-(compound B-2-5-1) mp [105-108]
　$[\alpha]_D$+16.9° (C 1.00, EtOH)
　HPLC 99.8% ee
　2HCl salt melting point: 184-188° C.

HPLC conditions column CHIRALCEL OD (4.6×250 mm)
　Mobile phase n-hexane:i-propanol:diethylamine=600:400:1
　Flow rate: 1.0 ml/min
　UV: 254 nm
　Column temperature: 40° C.

EXAMPLE 16

Step 1: Production of (±)-2-(5-nitro-2,4,6,7-tetramethyldihydrobenzofuran-2-ylmethyl)-2,3,4,9-tetrahydro-1-H-beta-carboline

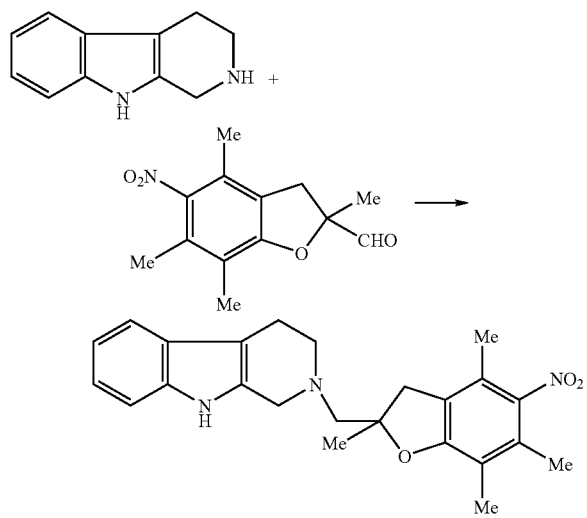

2.0 g of 2,4,6,7-tetramethyl-5-nitrodihydrobenzofuran-2-aldehyde, 1.52 g of 2,3,4,9-tetrahydro-1H-beta-carboline, 50 ml of methylene chloride, 0.8 ml of acetic acid and 2.04 g of sodium triacetoxyborohydride were added, followed by stirring overnight at room temperature. The mixture was poured into ice-water and an aqueous sodium hydroxide solution was added. The reaction solution was extracted with chloroform, washed with saturated saline and dried over anhydrous magnesium sulfate and, after the solvent was distilled off under reduced pressure, the residue was purified by silica gel column chromatography (chloroform:ethyl acetate=50:1) to obtain 1.49 g of the objective product.

Step 2: Production of (±)-2-(5-amino-2,4,6,7-tetramethyl-2,3-dihydrobenzofuran-2-ylmethyl)-2,3,4,9-tetrahydro-1H-beta-carboline

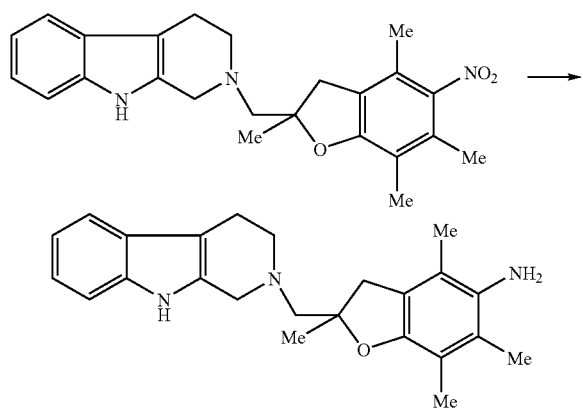

1.49 g of (±)-2-(5-nitro-2,4,6,7-tetramethyl-2,3-dihydrobenzofuran-2-ylmethyl)-2,3,4,9-tetrahydro-1H-beta-carboline, 2.49 g of stannous chloride, 11 ml of hydrochloric acid and 25 ml of ethanol were added and, after heating at reflux for 6.5 hours, the mixture was poured into ice-water and an aqueous sodium hydroxide solution was added. The reaction solution was extracted with chloroform, washed with saturated saline and dried over anhydrous magnesium sulfate and, after the solvent was distilled off under reduced pressure, the residue was purified by silica gel column chromatography (chloroform:methanol=100:3) to obtain 1.07 g of the objective product (melting point: 150-153° C.)

EXAMPLE 17

Step 1: Production of (±)-(1,3,4,9-tetrahydro-beta-carboline-2-yl)-(5-nitro-2,4,6,7-tetramethyldihydrobenzofuran-2-yl)methanone

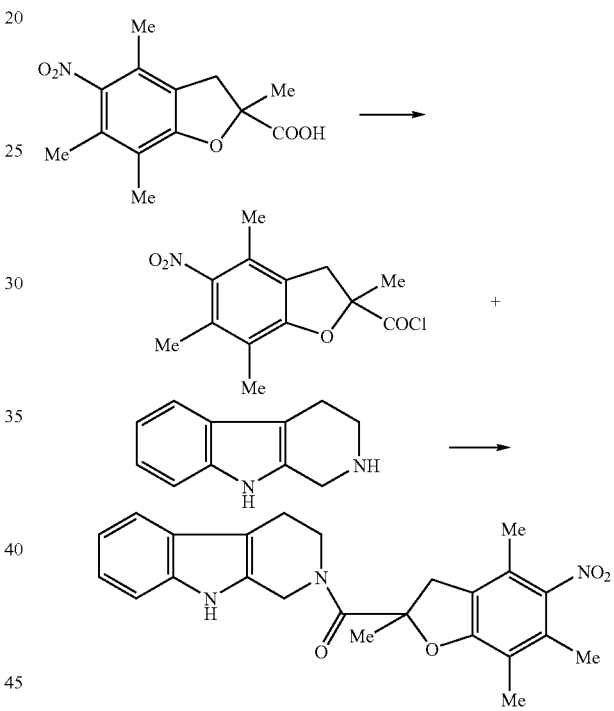

0.5 g of 2,4,6,7-tetramethyl-5-nitrodihydrobenzofuran-2-carboxylic acid, 20 ml of methylene chloride and 0.27 g of thionyl chloride were added, followed by heating at reflux for 2 hours. After returning the temperature to room temperature, the solvent was distilled off to obtain 2,4,6,7-tetramethyl-5-nitro-2,3-dihydrobenzofuran-2-carbonyl chloride. To 0.33 g of 2,3,4,9-tetrahydro-1H-beta-carboline, 0.23 g of triethylamine and 15 ml of DMF, a solution prepared by dissolving 2,4,6,7-tetramethyl-5-nitro-2,3-dihydrobenzofuran-2-carbonyl chloride in DMF was added, followed by stirring overnight at room temperature. The mixture was poured into ice-water and a crystal was collected by filtration. The crystal was dissolved in chloroform, washed with saturated saline and dried over anhydrous magnesium sulfate and, after the solvent was distilled off under reduced pressure, the residue was purified by silica gel column chromatography (chloroform:methanol=100:1) to obtain 0.54 g of the objective product.

Step 2: Production of (±)-(5-amino-2,4,6,7-tetramethyl-2,3-dihydrobenzofuran-2-yl)-(1,3,4,9-tetrahydro-beta-carboline-2-yl)-methanone

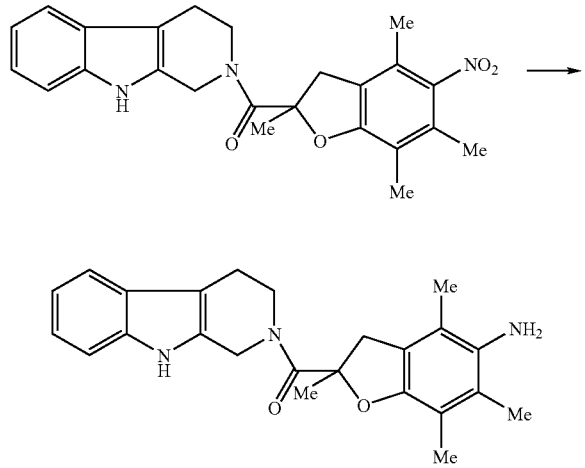

0.54 g of (±)-(1,3,4,9-tetrahydro-beta-carboline-2-yl)-(5-nitro-2,4,6,7-tetramethyldihydrobenzofuran-2-yl)methanone, 1.86 g of zinc, 0.19 g of calcium chloride dehydrate and 30 ml of ethanol were added, followed by heating at reflux overnight. The insoluble matter was filtered through celite and the solvent was distilled off. The reaction solution was mixed with water, extracted with chloroform, washed with saturated saline and dried over anhydrous magnesium sulfate and, after the solvent was distilled off under reduced pressure, the residue was purified by silica gel column chromatography (chloroform:ethyl acetate=50:1) to obtain 0.19 g of the objective product (melting point: 129-133° C.)

REFERENCE EXAMPLE 1

Production of 2,3,5-trimethylphenyl-2-methyl-2-propenylether

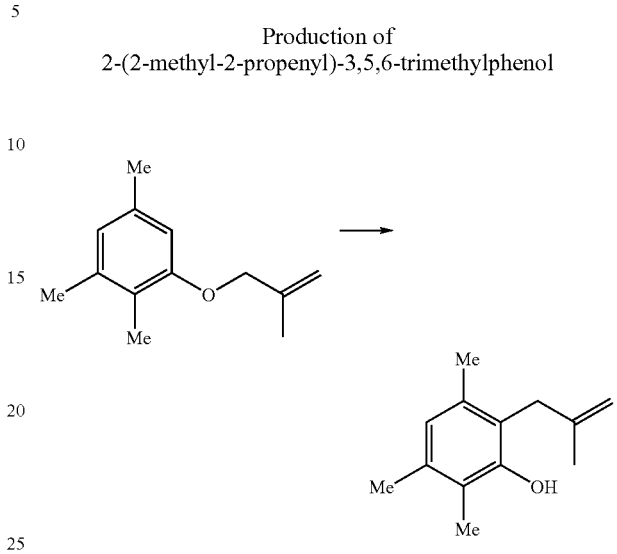

91.1 g of 2,3,5-trimethylphenol, 65.3 g of 3-chloro-2-methylpropene and 99 g of potassium carbonate were added to 700 ml of DMF, followed by stirring at 80° C. for 3 hours. After cooling, the reaction solution was poured into ice-water and then extracted with ethyl acetate. The solution was washed in turn with water and saturated saline and dried over anhydrous magnesium sulfate, and then the solvent was distilled off under reduced pressure and the residue was purified by silica gel column chromatography (benzene:hexane=1:1) to obtain 102 g of the objective product.

REFERENCE EXAMPLE 2

Production of 2-(2-methyl-2-propenyl)-3,5,6-trimethylphenol 26.6 g of 2,3,5-trimethylphenyl-2-methyl-2-propenylether was dissolved in 131 ml of diethylaniline, followed by stirring under an argon atmosphere at 200° C. for 2 hours. After cooling, the solution was poured into 6N-hydrochloric acid and then extracted with ether. The solution was washed in turn with dilute hydrochloric acid, water and saturated saline and dried over anhydrous magnesium sulfate and, after the solvent was distilled of under reduced pressure, the residue was purified by silica gel column chromatography (benzene:hexane=1:1) to obtain 21.4 g of the objective product.

REFERENCE EXAMPLE 3

Production of 2-hydroxymethyl-2,4,6,7-tetramethyldihydrobenzofuran

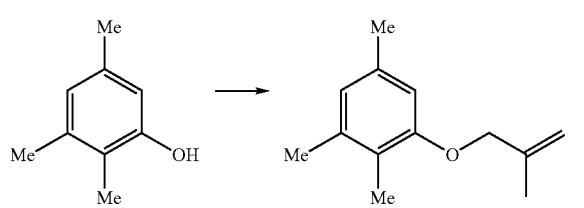

31.86 g of 2-(2-methyl-2-propenyl)-3,5,6-trimethylphenol was dissolved in 600 ml of methylene chloride and 47.5 g of methchloroperbenzoic acid was gradually charged while maintaining at 0° C. After stirring at 0° C. for 2 hours, the solution was poured into an aqueous sodium hydrogen carbonate. The organic layer was extracted with chloroform, washed with an aqueous saturated sodium hydrogen carbonate solution and dried over anhydrous magnesium sulfate and, after the solvent was distilled off, the residue was purified by silica gel column chromatography (chloroform) to obtain 17 g of the objective product.

REFERENCE EXAMPLE 4

Production of 2-hydroxymethyl-2,4,6,7-tetramethyl-5-nitrodihydrobenzofuran

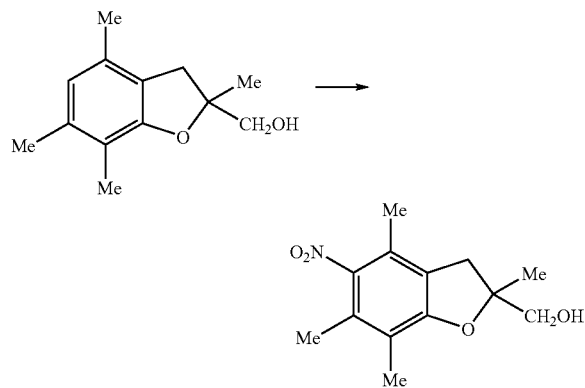

2.3 g of 2-hydroxymethyl-2,4,6,7-tetramethyldihydrobenzofuran was dissolved in 30 ml of anhydrous acetic acid and 1.9 ml of nitric acid was added dropwise while stirring at 0° C. After stirring at 0° C. for one hour, the solution was poured into ice-water, followed by stirring at room temperature for one hour. The reaction solution was extracted with ether, washed with saturated saline and dried over anhydrous magnesium sulfate and, after the solvent was distilled off under reduced pressure, the residue was purified by silica gel column chromatography (chloroform) to obtain 1.34 g of the objective product.

REFERENCE EXAMPLE 5

Production of 2,4,6,7-tetramethyl-5-nitrodihydrobenzofuran-2-aldehyde

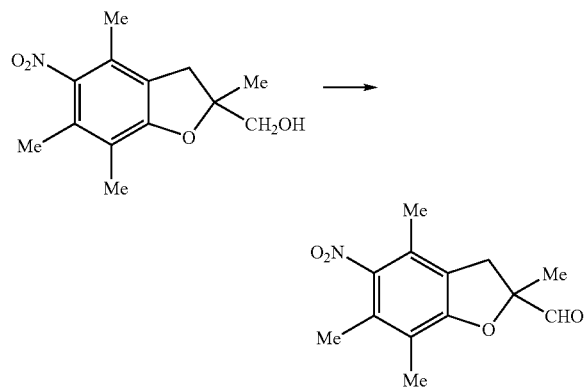

Under an argon atmosphere, 0.57 ml of oxalic acid dichloride was dissolved in 12 ml of methylene chloride, followed by cooling to −78° C. To this solution, a solution prepared by dissolving 1.1 ml of DMSO in 2 ml of methylene chloride was added dropwise at −65 C or lower, followed by stirring for 10 minutes. Furthermore, a solution prepared by dissolving 1.34 g of 2-hydroxymethyl-2,4,6,7-tetramethyl-5-nitrodihydrobenzofuran in 4 ml of methylene chloride was added dropwise, followed by stirring at −78° C. for 3 hours. After the completion of the reaction, 4.2 ml of triethylamine was added dropwise and the reaction solution was heated to room temperature and then 1N-hydrochloric acid was added. The organic layer was extracted with chloroform, washed with saturated saline and dried over anhydrous magnesium sulfate, and then solvent was distilled off under reduced pressure and the residue was purified by silica gel column chromatography (chloroform) to obtain 0.86 g of the objective product.

REFERENCE EXAMPLE 6

Production of 2,4,6,7-tetramethyl-5-nitrodihydrobenzofuran-2-carboxylic acid

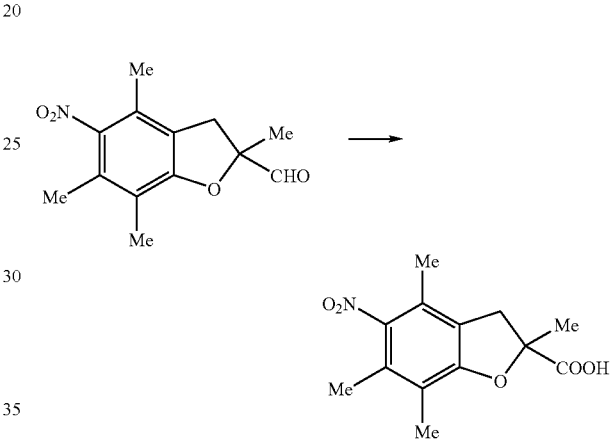

2.39 g of 2,4,6,7-tetramethyl-5-nitrodihydrobenzofuran-2-aldehyde and 31 g of 2-methyl-2-butene were dissolved in 190 ml of t-butanol and a solution prepared by dissolving 7.77 g of sodium chlorite and 10.1 g of sodium dihydrogen phosphate dehydrate in 78 ml of water was added dropwise under ice cooling, followed by stirring at room temperature for 2 hours. After 2-methyl-2-butene and t-butanol were distilled off under reduced pressure, water was added and the reaction solution was extracted with ether. The solution was washed with saturated saline and dried over anhydrous magnesium sulfate, and then the solvent was distilled off under reduced pressure and the residue was crystallized from ether-hexane to obtain 1.20 g of the objective product.

REFERENCE EXAMPLE 7

Production of 6-nitro-2-methoxymethyl-2,5,7,8-tetramethylchroman-4-one

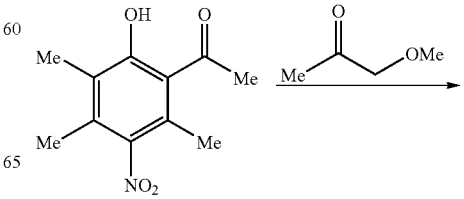

-continued

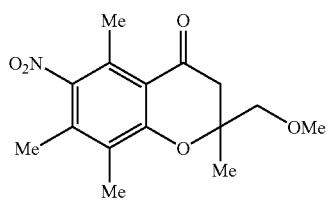

To the reaction solution prepared by dissolving 66.5 g of 5-nitro-2-hydroxy-3,4,6-trimethylacetophenone and 78.8 g of methoxyacetone in 500 ml of toluene, 6.4 g of pyrrolidine was added at room temperature, followed by stirring at room temperature for 24 hours and further heating at reflux for 3 hours. The reaction solution was distilled off under reduced pressure and the residue was subjected to silica gel column chromatography (hexane:ethyl acetate=7:1→3:1) to obtain 29.2 g of the objective product.

REFERENCE EXAMPLE 8

Production of 6-nitro-4-hydroxy-2-methoxymethyl-2,5,7,8-tetramethylchroman

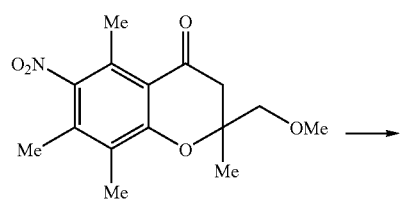

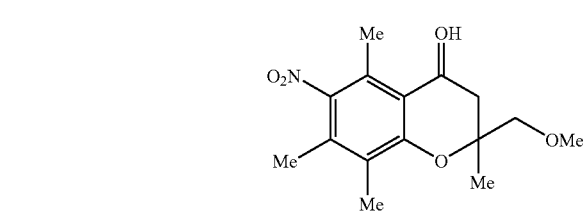

To 10 g of 6-nitro-2-methoxymethyl-2,5,7,8-tetramethyl-chroman-4-one, 100 ml of methanol was added and 1.3 g of sodium borohydride was added at 0° C., followed by stirring at 0° C. for one hour. The reaction solution was poured into water and then extracted with ethyl acetate. The organic layer was washed with saturated saline and then dried over anhydrous magnesium sulfate. After removing magnesium sulfate by filtration and concentrating under reduced pressure, 10.1 g of the objective compound was obtained.

REFERENCE EXAMPLE 9

Production of 6-nitro-2-methoxymethyl-2,5,7,8-tetramethyl (2H) chromene

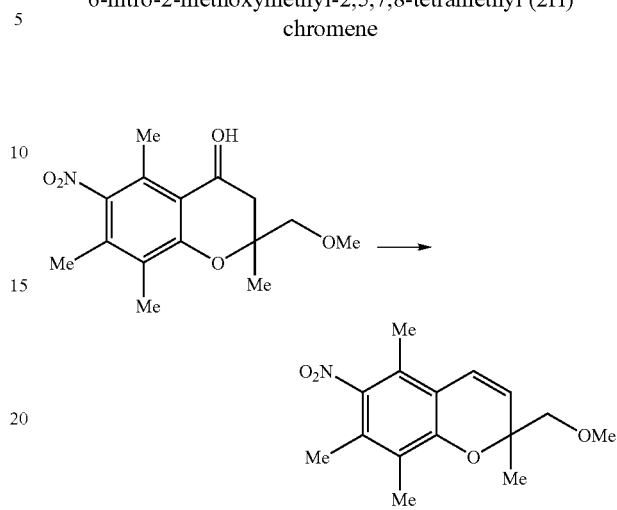

To 10.1 g of 6-nitro-4-hydroxy-2-methoxymethyl-2,5,7,8-tetramethylchroman, 200 ml of benzene was added and 1.0 g of p-toluenesulfonic acid was added, followed by heating at reflux for 2 hours using a Dean-Stark apparatus. The reaction solution was poured into water and then extracted with ethyl acetate. The organic layer was washed with an aqueous saturated sodium hydrogen carbonate solution, washed with saturated saline and then dried over anhydrous magnesium sulfate. After removing magnesium sulfate by filtration and concentrating under reduced pressure, 9.4 g of the objective oily compound was obtained.

REFERENCE EXAMPLE 10

Production of 6-nitro-2-methoxymethyl-2,5,7,8-tetramethylchroman

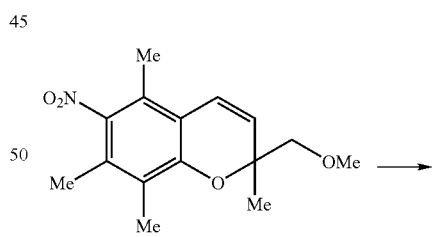

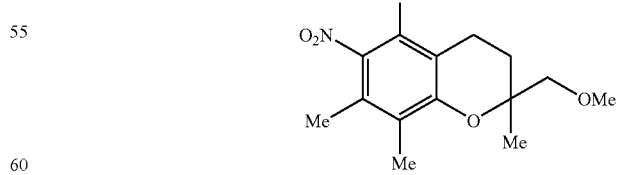

9.4 g of 6-nitro-2-methoxymethyl-2,5,7,8-tetramethyl (2H) chromene was dissolved in 100 ml of ethanol and 1.0 g of a 10% palladium carbon catalyst was added and, after sealing hydrogen, the catalytic hydrogenation reaction was carried out at room temperature under normal pressure for 24 hours. After the completion of the reaction, the reaction solution was filtered and then concentrated under reduced pressure to obtain 9.5 g of the objective oily compound.

REFERENCE EXAMPLE 11

Production of 6-nitro-2-hydroxymethyl-2,5,7,8-tetramethylchroman

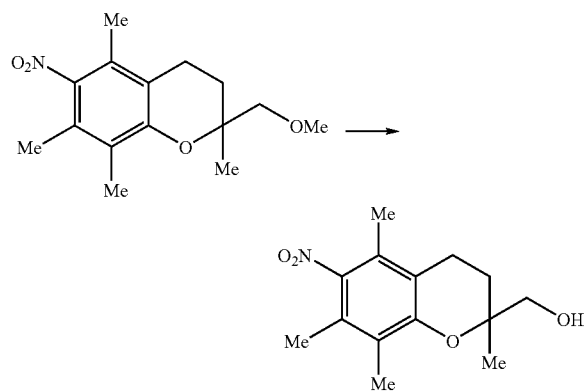

9.5 g of 6-nitro-2-methoxymethyl-2,5,7,8-tetramethylchroman was dissolved in 80 ml of methylene chloride and 31.4 ml of a 1M boron tribromide methylene chloride solution was added under a nitrogen gas flow at 0° C., followed by stirring at 0° C. for 3 hours. After the completion of the reaction, the reaction solution was poured into water and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (hexane:ethyl acetate=2:1) to obtain 4.5 g of the objective product.

REFERENCE EXAMPLE 12

Production of 6-nitro-2-formyl-2,5,7,8-tetramethylchroman

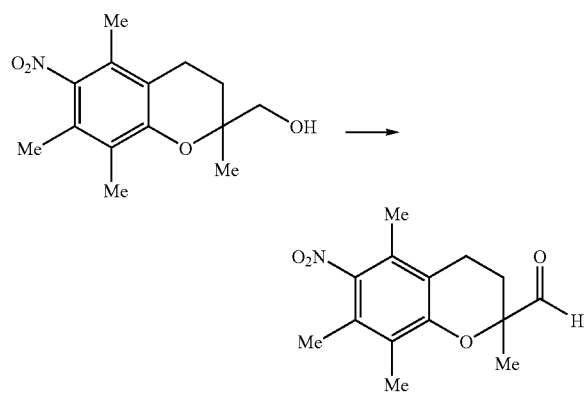

Under a nitrogen flow at −60° C., 1.6 ml of oxalic acid dichloride was dissolved in 40 ml of methylene chloride and 3.1 ml of DMSO was added dropwise at −60° C., followed by stirring for 5 minutes. A solution prepared by dissolving 3.9 g of 6-nitro-2-hydroxymethyl-2,5,7,8-tetramethylchroman in 10 ml of methylene chloride was added dropwise under a nitrogen gas flow at −60° C., followed by stirring at −60° C. for 30 minutes. 12 ml of triethylamine was added at −60° C. and the temperature was gradually raised to room temperature, thereby to complete the reaction. After the completion of the reaction, the reaction solution was poured into water and then extracted with chloroform. The organic layer was washed with saturated saline and then dried over anhydrous magnesium sulfate. After removing magnesium sulfate by filtration and concentrating under reduced pressure, the residue was subjected to silica gel column chromatography (hexane:ethyl acetate=2:1) to obtain 3.4 g of the objective product as a crystal.

REFERENCE EXAMPLE 13

Production of 6-nitro-2,5,7,8-tetramethylchroman-2-carboxylic acid

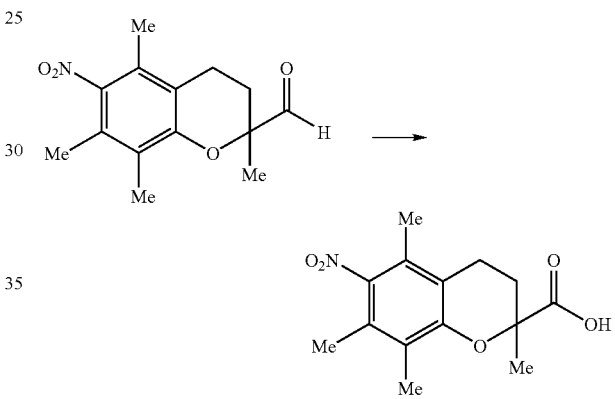

2.3 g of 6-nitro-2-formyl-2,5,7,8-tetramethylchroman was dissolved in 150 ml of t-butanol and 23 g of 2-methyl-2-butene was added at room temperature. An aqueous solution prepared by dissolving 5.8 g of sodium chlorite and 7.6 g of sodium dihydrogen phosphate dehydrate in 60 ml of water was added dropwise at room temperature, followed by stirring at room temperature for 2 hours. After the completion of the reaction, the reaction solution was poured into water and then extracted with ether. The organic layer was partitioned with an aqueous 5% sodium hydrogen carbonate solution and the ether layer was discarded. The pH of the aqueous layer was adjusted to 4 with 10% hydrochloric acid, followed by extraction with ethyl acetate. The organic layer was washed with saturated saline and then dried over anhydrous magnesium sulfate. After removing magnesium sulfate by filtration and concentrating under reduced pressure, the resulting crystal was washed with hexane to obtain 1.6 g of the objective product.

Specific examples of the compounds of the present invention are shown in Tables 1 to 29. With respect to the compounds in which "& NMR" is described in the column of physical constant in the tables, NMR data were described in the last of the tables. "decomp." in the tables indicates decomposition. Abbreviations and symbols in the tables are as follows:

Me: methyl, Et: ethyl, Bu: butyl, Ph: phenyl, a1: 1-imidazolyl, and a2: 1H-pyrazol-5-yl. The numeral attached to a1 and a2 in the column A indicates the position of a phenyl group to be attached.

h1:
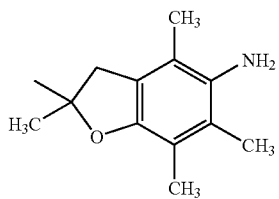

h2:
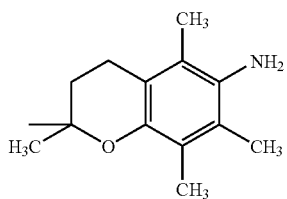

h3:
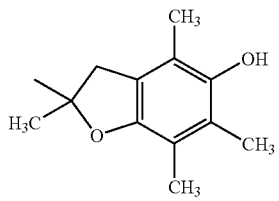

h4:
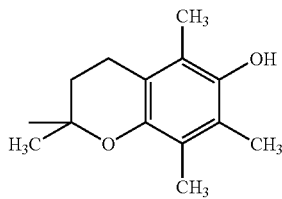

h5:
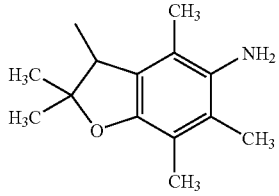

h6:
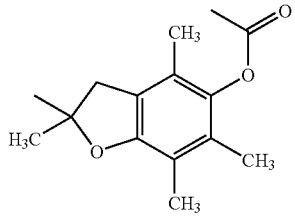

h7:
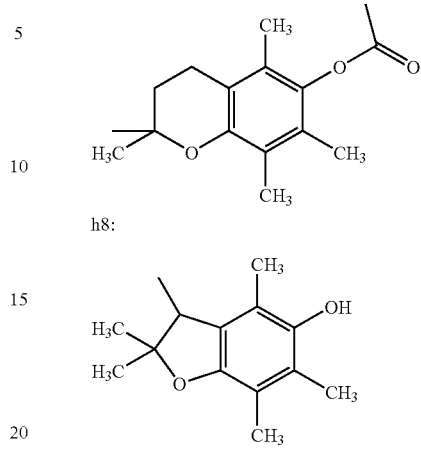

-continued h8:
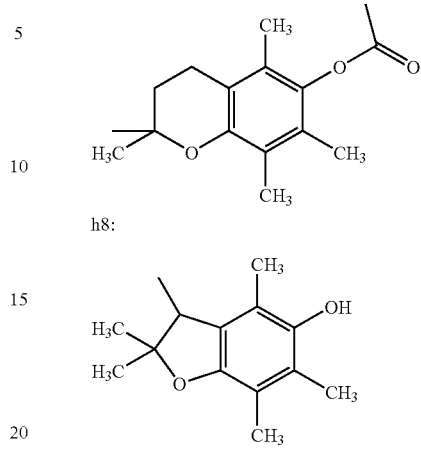

TABLE 1

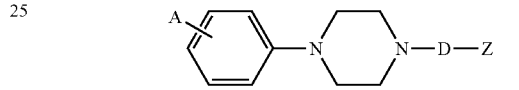

| Compound No. | A | D | Z | Physical Constant [ ] m.p. ° C. |
|---|---|---|---|---|
| B-1-1 | 4-a1 | CO | h1 | [189-191] |
| B-1-2 | 4-a1 | $CH_2$ | h1 | (165-167) |
| B-1-3 | 4-a1 | CO | h2 | [110-115] |
| B-1-4 | 4-a1 | $CH_2$ | h2 | [65-67] |
| B-1-5 | 4-a1 | CO | h3 | [249-251] |
| B-1-6 | 4-a1 | $CH_2$ | h3 | [219-221] |
| B-1-7 | 4-a1 | CO | h4 | [218-220] |
| B-1-8 | 4-a1 | $CH_2$ | h4 | [94-98] |
| B-1-9 | 4-a1 | CO | h5 | [288-290] |
| B-1-10 | 4-a1 | $CH_2$ | h5 | [68-70] |
| B-1-11 | 4-a1 | CO | h6 | & NMR |
| B-1-12 | 4-a1 | $CH_2$ | h6 | $n_D^{20.7}$1.5527 |
| B-1-13 | 4-a1 | CO | h7 | & NMR |
| B-1-14 | 4-a1 | $CH_2$ | h7 | [176-178] |
| B-1-15 | 4-a1 | CO | h8 | [243-246] |
| B-1-16 | 4-a1 | $CH_2$ | h8 | [201-203] |
| B-1-17 | 3-a1 | CO | h1 | [90-93] |
| B-1-18 | 3-a1 | $CH_2$ | h1 | [58-60] |
| B-1-19 | 3-a1 | CO | h2 | [90-93] |
| B-1-20 | 3-a1 | $CH_2$ | h2 | [146-149] |
| B-1-21 | 3-a1 | CO | h3 | |
| B-1-22 | 3-a1 | $CH_2$ | h3 | [148-151] |
| B-1-23 | 3-a1 | CO | h4 | |
| B-1-24 | 3-a1 | $CH_2$ | h4 | |
| B-1-25 | 3-a1 | CO | h5 | |
| B-1-26 | 3-a1 | $CH_2$ | h5 | [197-198] |
| B-1-27 | 3-a1 | CO | h6 | |
| B-1-28 | 3-a1 | $CH_2$ | h6 | & NMR |
| B-1-29 | 3-a1 | CO | h7 | |
| B-1-30 | 3-a1 | $CH_2$ | h7 | |
| B-1-31 | 3-a1 | CO | h8 | |
| B-1-32 | 3-a1 | $CH_2$ | h8 | |
| B-1-33 | 4-a2 | CO | h1 | [128-130] |
| B-1-34 | 4-a2 | $CH_2$ | h1 | [205-207] |
| B-1-35 | 4-a2 | CO | h2 | [115-120] |
| B-1-36 | 4-a2 | $CH_2$ | h2 | [110-115] |
| B-1-37 | 4-a2 | CO | h3 | & NMR |
| B-1-38 | 4-a2 | $CH_2$ | h3 | |
| B-1-39 | 4-a2 | CO | h4 | & NMR |
| B-1-40 | 4-a2 | $CH_2$ | h4 | |
| B-1-41 | 4-a2 | CO | h5 | |
| B-1-42 | 4-a2 | $CH_2$ | h5 | |
| B-1-43 | 4-a2 | CO | h6 | |
| B-1-44 | 4-a2 | $CH_2$ | h6 | |

TABLE 1-continued

A—(phenyl)—N(piperazine)N—D—Z

| Compound No. | A | D | Z | Physical Constant [ ] m.p. ° C. |
|---|---|---|---|---|
| B-1-45 | 4-a2 | CO | h7 | |
| B-1-46 | 4-a2 | CH$_2$ | h7 | |
| B-1-47 | 4-a2 | CO | h8 | |
| B-1-48 | 4-a2 | CH$_2$ | h8 | |
| B-1-49 | 3-a2 | CO | h1 | [120-122] |
| B-1-50 | 3-a2 | CH$_2$ | h1 | [94-97] |
| B-1-51 | 3-a2 | CO | h2 | |
| B-1-52 | 3-a2 | CH$_2$ | h2 | |
| B-1-53 | 3-a2 | CO | h3 | [120-122] |
| B-1-54 | 3-a2 | CH$_2$ | h3 | |
| B-1-55 | 3-a2 | CO | h4 | |
| B-1-56 | 3-a2 | CH$_2$ | h4 | |
| B-1-57 | 3-a2 | CO | h5 | |
| B-1-58 | 3-a2 | CH$_2$ | h5 | |
| B-1-59 | 3-a2 | CO | h6 | |
| B-1-60 | 3-a2 | CH$_2$ | h6 | |
| B-1-61 | 3-a2 | CO | h7 | |
| B-1-62 | 3-a2 | CH$_2$ | h7 | |
| B-1-63 | 3-a2 | CO | h8 | |
| B-1-64 | 3-a2 | CH$_2$ | h8 | |

TABLE 2

A—(phenyl)—(piperidine)N—D—Z

| Compound No. | A | D | Z | Physical Constant [ ] m.p. ° C. |
|---|---|---|---|---|
| B-1-65 | 4-a1 | CO | h1 | |
| B-1-66 | 4-a1 | CH$_2$ | h1 | [170-172] |
| B-1-67 | 4-a1 | CO | h2 | |
| B-1-68 | 4-a1 | CH$_2$ | h2 | [191-193] |
| B-1-69 | 4-a1 | CO | h3 | |
| B-1-70 | 4-a1 | CH$_2$ | h3 | |
| B-1-71 | 4-a1 | CO | h4 | |
| B-1-72 | 4-a1 | CH$_2$ | h4 | |
| B-1-73 | 4-a1 | CO | h5 | |
| B-1-74 | 4-a1 | CH$_2$ | h5 | |
| B-1-75 | 4-a1 | CO | h6 | |
| B-1-76 | 4-a1 | CH$_2$ | h6 | |
| B-1-77 | 4-a1 | CO | h7 | |
| B-1-78 | 4-a1 | CH$_2$ | h7 | |
| B-1-79 | 4-a1 | CO | h8 | |
| B-1-80 | 4-a1 | CH$_2$ | h8 | |
| B-1-81 | 3-a1 | CO | h1 | |
| B-1-82 | 3-a1 | CH$_2$ | h1 | |
| B-1-83 | 3-a1 | CO | h2 | |
| B-1-84 | 3-a1 | CH$_2$ | h2 | |
| B-1-85 | 3-a1 | CO | h3 | |
| B-1-86 | 3-a1 | CH$_2$ | h3 | |
| B-1-87 | 3-a1 | CO | h4 | |
| B-1-88 | 3-a1 | CH$_2$ | h4 | |
| B-1-89 | 3-a1 | CO | h5 | |
| B-1-90 | 3-a1 | CH$_2$ | h5 | |
| B-1-91 | 3-a1 | CO | h6 | |
| B-1-92 | 3-a1 | CH$_2$ | h6 | |
| B-1-93 | 3-a1 | CO | h7 | |
| B-1-94 | 3-a1 | CH$_2$ | h7 | |
| B-1-95 | 3-a1 | CO | h8 | |
| B-1-96 | 3-a1 | CH$_2$ | h8 | |
| B-1-97 | 4-a2 | CO | h1 | |
| B-1-98 | 4-a2 | CH$_2$ | h1 | |
| B-1-99 | 4-a2 | CO | h2 | |
| B-1-100 | 4-a2 | CH$_2$ | h2 | |
| B-1-101 | 4-a2 | CO | h3 | |
| B-1-102 | 4-a2 | CH$_2$ | h3 | |

TABLE 2-continued

| Compound No. | A | D | Z | Physical Constant [ ] m.p. ° C. |
|---|---|---|---|---|
| B-1-103 | 4-a2 | CO | h4 | |
| B-1-104 | 4-a2 | CH$_2$ | h4 | |
| B-1-105 | 4-a2 | CO | h5 | |
| B-1-106 | 4-a2 | CH$_2$ | h5 | |
| B-1-107 | 4-a2 | CO | h6 | |
| B-1-108 | 4-a2 | CH$_2$ | h6 | |
| B-1-109 | 4-a2 | CO | h7 | |
| B-1-110 | 4-a2 | CH$_2$ | h7 | |
| B-1-111 | 4-a2 | CO | h8 | |
| B-1-112 | 4-a2 | CH$_2$ | h8 | |
| B-1-113 | 3-a2 | CO | h1 | |
| B-1-114 | 3-a2 | CH$_2$ | h1 | |
| B-1-115 | 3-a2 | CO | h2 | |
| B-1-116 | 3-a2 | CH$_2$ | h2 | |
| B-1-117 | 3-a2 | CO | h3 | |
| B-1-118 | 3-a2 | CH$_2$ | h3 | |
| B-1-119 | 3-a2 | CO | h4 | |
| B-1-120 | 3-a2 | CH$_2$ | h4 | |
| B-1-121 | 3-a2 | CO | h5 | |
| B-1-122 | 3-a2 | CH$_2$ | h5 | |
| B-1-123 | 3-a2 | CO | h6 | |
| B-1-124 | 3-a2 | CH$_2$ | h6 | |
| B-1-125 | 3-a2 | CO | h7 | |
| B-1-126 | 3-a2 | CH$_2$ | h7 | |
| B-1-127 | 3-a2 | CO | h8 | |
| B-1-128 | 3-a2 | CH$_2$ | h8 | |

TABLE 3

A—(phenyl)—N(diazepane)N—D—Z

| Compound No. | A | D | Z | Physical Constant [ ] m.p. ° C. |
|---|---|---|---|---|
| B-1-129 | 4-a1 | CO | h1 | [85-90] |
| B-1-130 | 4-a1 | CH$_2$ | h1 | [60-65] |
| B-1-131 | 4-a1 | CO | h2 | [206-210] |
| B-1-132 | 4-a1 | CH$_2$ | h2 | [57-60] |
| B-1-133 | 4-a1 | CO | h3 | |
| B-1-134 | 4-a1 | CH$_2$ | h3 | |
| B-1-135 | 4-a1 | CO | h4 | |
| B-1-136 | 4-a1 | CH$_2$ | h4 | |
| B-1-137 | 4-a1 | CO | h5 | |
| B-1-138 | 4-a1 | CH$_2$ | h5 | [178-180) |
| B-1-139 | 4-a1 | CO | h6 | |
| B-1-140 | 4-a1 | CH$_2$ | h6 | |
| B-1-141 | 4-a1 | CO | h7 | |
| B-1-142 | 4-a1 | CH$_2$ | h7 | |
| B-1-143 | 4-a1 | CO | h8 | |
| B-1-144 | 4-a1 | CH$_2$ | h8 | |
| B-1-145 | 3-a1 | CO | h1 | [95-100] |
| B-1-146 | 3-a1 | CH$_2$ | h1 | [70-75] |
| B-1-147 | 3-a1 | CO | h2 | [80-83] |
| B-1-148 | 3-a1 | CH$_2$ | h2 | & NMR |
| B-1-149 | 3-a1 | CO | h3 | |
| B-1-150 | 3-a1 | CH$_2$ | h3 | |
| B-1-151 | 3-a1 | CO | h4 | |
| B-1-152 | 3-a1 | CH$_2$ | h4 | |
| B-1-153 | 3-a1 | CO | h5 | |
| B-1-154 | 3-a1 | CH$_2$ | h5 | |
| B-1-155 | 3-a1 | CO | h6 | |
| B-1-156 | 3-a1 | CH$_2$ | h6 | |
| B-1-157 | 3-a1 | CO | h7 | |
| B-1-158 | 3-a1 | CH$_2$ | h7 | |
| B-1-159 | 3-a1 | CO | h8 | |

TABLE 3-continued

| Compound No. | A | D | Z | Physical Constant [ ] m.p. ° C. |
|---|---|---|---|---|
| B-1-160 | 3-a1 | CH$_2$ | h8 | |
| B-1-161 | 4-a2 | CO | h1 | |
| B-1-162 | 4-a2 | CH$_2$ | h1 | [78-80] |
| B-1-163 | 4-a2 | CO | h2 | |
| B-1-164 | 4-a2 | CH$_2$ | h2 | |
| B-1-165 | 4-a2 | CO | h3 | |
| B-1-166 | 4-a2 | CH$_2$ | h3 | |
| B-1-167 | 4-a2 | CO | h4 | |
| B-1-168 | 4-a2 | CH$_2$ | h4 | |
| B-1-169 | 4-a2 | CO | h5 | |
| B-1-170 | 4-a2 | CH$_2$ | h5 | |
| B-1-171 | 4-a2 | CO | h6 | |
| B-1-172 | 4-a2 | CH$_2$ | h6 | |
| B-1-173 | 4-a2 | CO | h7 | |
| B-1-174 | 4-a2 | CH$_2$ | h7 | |
| B-1-175 | 4-a2 | CO | h8 | |
| B-1-176 | 4-a2 | CH$_2$ | h8 | |
| B-1-177 | 3-a2 | CO | h1 | |
| B-1-178 | 3-a2 | CH$_2$ | h1 | |
| B-1-179 | 3-a2 | CO | h2 | |
| B-1-180 | 3-a2 | CH$_2$ | h2 | |
| B-1-181 | 3-a2 | CO | h3 | |
| B-1-182 | 3-a2 | CH$_2$ | h3 | |
| B-1-183 | 3-a2 | CO | h4 | |
| B-1-184 | 3-a2 | CH$_2$ | h4 | |
| B-1-185 | 3-a2 | CO | h5 | |
| B-1-186 | 3-a2 | CH$_2$ | h5 | |
| B-1-187 | 3-a2 | CO | h6 | |
| B-1-188 | 3-a2 | CH$_2$ | h6 | |
| B-1-189 | 3-a2 | CO | h7 | |
| B-1-190 | 3-a2 | CH$_2$ | h7 | |
| B-1-191 | 3-a2 | CO | h8 | |
| B-1-192 | 3-a2 | CH$_2$ | h8 | |

TABLE 4

| Compound No. | A | D | Z | Physical Constant [ ] m.p. ° C. |
|---|---|---|---|---|
| B-1-193 | 4-a1 | CO | h1 | |
| B-1-194 | 4-a1 | CH$_2$ | h1 | [161-163] |
| B-1-195 | 4-a1 | CO | h2 | |
| B-1-196 | 4-a1 | CH$_2$ | h2 | [149-151] |
| B-1-197 | 4-a1 | CO | h3 | |
| B-1-198 | 4-a1 | CH$_2$ | h3 | |
| B-1-199 | 4-a1 | CO | h4 | |
| B-1-200 | 4-a1 | CH$_2$ | h4 | |
| B-1-201 | 4-a1 | CO | h5 | |
| B-1-202 | 4-a1 | CH$_2$ | h5 | |
| B-1-203 | 4-a1 | CO | h6 | |
| B-1-204 | 4-a1 | CH$_2$ | h6 | |
| B-1-205 | 4-a1 | CO | h7 | |
| B-1-206 | 4-a1 | CH$_2$ | h7 | |
| B-1-207 | 4-a1 | CO | h8 | |
| B-1-208 | 4-a1 | CH$_2$ | h8 | |
| B-1-209 | 3-a1 | CO | h1 | |
| B-1-210 | 3-a1 | CH$_2$ | h1 | |
| B-1-211 | 3-a1 | CO | h2 | |
| B-1-212 | 3-a1 | CH$_2$ | h2 | |
| B-1-213 | 3-a1 | CO | h3 | |
| B-1-214 | 3-a1 | CH$_2$ | h3 | |
| B-1-215 | 3-a1 | CO | h4 | |
| B-1-216 | 3-a1 | CH$_2$ | h4 | |

TABLE 4-continued

| Compound No. | A | D | Z | Physical Constant [ ] m.p. ° C. |
|---|---|---|---|---|
| B-1-217 | 3-a1 | CO | h5 | |
| B-1-218 | 3-a1 | CH$_2$ | h5 | |
| B-1-219 | 3-a1 | CO | h6 | |
| B-1-220 | 3-a1 | CH$_2$ | h6 | |
| B-1-221 | 3-a1 | CO | h7 | |
| B-1-222 | 3-a1 | CH$_2$ | h7 | |
| B-1-223 | 3-a1 | CO | h8 | |
| B-1-224 | 3-a1 | CH$_2$ | h8 | |
| B-1-225 | 4-a2 | CO | h1 | |
| B-1-226 | 4-a2 | CH$_2$ | h1 | |
| B-1-227 | 4-a2 | CO | h2 | |
| B-1-228 | 4-a2 | CH$_2$ | h2 | |
| B-1-229 | 4-a2 | CO | h3 | |
| B-1-230 | 4-a2 | CH$_2$ | h3 | |
| B-1-231 | 4-a2 | CO | h4 | |
| B-1-232 | 4-a2 | CH$_2$ | h4 | |
| B-1-233 | 4-a2 | CO | h5 | |
| B-1-234 | 4-a2 | CH$_2$ | h5 | |
| B-1-235 | 4-a2 | CO | h6 | |
| B-1-236 | 4-a2 | CH$_2$ | h6 | |
| B-1-237 | 4-a2 | CO | h7 | |
| B-1-238 | 4-a2 | CH$_2$ | h7 | |
| B-1-239 | 4-a2 | CO | h8 | |
| B-1-240 | 4-a2 | CH$_2$ | h8 | |
| B-1-241 | 3-a2 | CO | h1 | |
| B-1-242 | 3-a2 | CH$_2$ | h1 | |
| B-1-243 | 3-a2 | CO | h2 | |
| B-1-244 | 3-a2 | CH$_2$ | h2 | |
| B-1-245 | 3-a2 | CO | h3 | |
| B-1-246 | 3-a2 | CH$_2$ | h3 | |
| B-1-247 | 3-a2 | CO | h4 | |
| B-1-248 | 3-a2 | CH$_2$ | h4 | |
| B-1-249 | 3-a2 | CO | h5 | |
| B-1-250 | 3-a2 | CH$_2$ | h5 | |
| B-1-251 | 3-a2 | CO | h6 | |
| B-1-252 | 3-a2 | CH$_2$ | h6 | |
| B-1-253 | 3-a2 | CO | h7 | |
| B-1-254 | 3-a2 | CH$_2$ | h7 | |
| B-1-255 | 3-a2 | CO | h8 | |
| B-1-256 | 3-a2 | CH$_2$ | h8 | |

TABLE 5

| Compound No. | A | D | Z | Physical Constant [ ] m.p. ° C. |
|---|---|---|---|---|
| B-1-257 | 4-a1 | CO | h1 | |
| B-1-258 | 4-a1 | CH$_2$ | h1 | |
| B-1-259 | 4-a1 | CO | h2 | |
| B-1-260 | 4-a1 | CH$_2$ | h2 | |
| B-1-261 | 4-a1 | CO | h3 | |
| B-1-262 | 4-a1 | CH$_2$ | h3 | [232] (decomp.) |
| B-1-263 | 4-a1 | CO | h4 | |
| B-1-264 | 4-a1 | CH$_2$ | h4 | |
| B-1-265 | 4-a1 | CO | h5 | |
| B-1-266 | 4-a1 | CH$_2$ | h5 | |
| B-1-267 | 4-a1 | CO | h6 | |
| B-1-268 | 4-a1 | CH$_2$ | h6 | |
| B-1-269 | 4-a1 | CO | h7 | |
| B-1-270 | 4-a1 | CH$_2$ | h7 | |
| B-1-271 | 4-a1 | CO | h8 | |

TABLE 5-continued

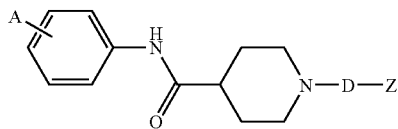

| Compound No. | A | D | Z | Physical Constant [ ] m.p. ° C. |
|---|---|---|---|---|
| B-1-272 | 4-a1 | CH$_2$ | h8 | |
| B-1-273 | 3-a1 | CO | h1 | |
| B-1-274 | 3-a1 | CH$_2$ | h1 | |
| B-1-275 | 3-a1 | CO | h2 | |
| B-1-276 | 3-a1 | CH$_2$ | h2 | |
| B-1-277 | 3-a1 | CO | h3 | |
| B-1-278 | 3-a1 | CH$_2$ | h3 | |
| B-1-279 | 3-a1 | CO | h4 | |
| B-1-280 | 3-a1 | CH$_2$ | h4 | |
| B-1-281 | 3-a1 | CO | h5 | |
| B-1-282 | 3-a1 | CH$_2$ | h5 | |
| B-1-283 | 3-a1 | CO | h6 | |
| B-1-284 | 3-a1 | CH$_2$ | h6 | |
| B-1-285 | 3-a1 | CO | h7 | |
| B-1-286 | 3-a1 | CH$_2$ | h7 | |
| B-1-287 | 3-a1 | CO | h8 | |
| B-1-288 | 3-a1 | CH$_2$ | h8 | |
| B-1-289 | 4-a2 | CO | h1 | |
| B-1-290 | 4-a2 | CH$_2$ | h1 | |
| B-1-291 | 4-a2 | CO | h2 | |
| B-1-292 | 4-a2 | CH$_2$ | h2 | |
| B-1-293 | 4-a2 | CO | h3 | |
| B-1-294 | 4-a2 | CH$_2$ | h3 | |
| B-1-295 | 4-a2 | CO | h4 | |
| B-1-296 | 4-a2 | CH$_2$ | h4 | |
| B-1-297 | 4-a2 | CO | h5 | |
| B-1-298 | 4-a2 | CH$_2$ | h5 | |
| B-1-299 | 4-a2 | CO | h6 | |
| B-1-300 | 4-a2 | CH$_2$ | h6 | |
| B-1-301 | 4-a2 | CO | h7 | |
| B-1-302 | 4-a2 | CH$_2$ | h7 | |
| B-1-303 | 4-a2 | CO | h8 | |
| B-1-304 | 4-a2 | CH$_2$ | h8 | |
| B-1-305 | 3-a2 | CO | h1 | |
| B-1-306 | 3-a2 | CH$_2$ | h1 | |
| B-1-307 | 3-a2 | CO | h2 | |
| B-1-308 | 3-a2 | CH$_2$ | h2 | |
| B-1-309 | 3-a2 | CO | h3 | |
| B-1-310 | 3-a2 | CH$_2$ | h3 | |
| B-1-311 | 3-a2 | CO | h4 | |
| B-1-312 | 3-a2 | CH$_2$ | h4 | |
| B-1-313 | 3-a2 | CO | h5 | |
| B-1-314 | 3-a2 | CH$_2$ | h5 | |
| B-1-315 | 3-a2 | CO | h6 | |
| B-1-316 | 3-a2 | CH$_2$ | h6 | |
| B-1-317 | 3-a2 | CO | h7 | |
| B-1-318 | 3-a2 | CH$_2$ | h7 | |
| B-1-319 | 3-a2 | CO | h8 | |
| B-1-320 | 3-a2 | CH$_2$ | h8 | |

TABLE 6

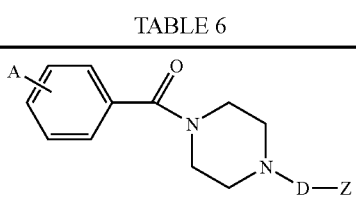

| Compound No. | A | D | Z | Physical Constant [ ] m.p. ° C. |
|---|---|---|---|---|
| B-1-321 | 4-a1 | CO | h1 | |
| B-1-322 | 4-a1 | CH$_2$ | h1 | |
| B-1-323 | 4-a1 | CO | h2 | |
| B-1-324 | 4-a1 | CH$_2$ | h2 | |
| B-1-325 | 4-a1 | CO | h3 | |
| B-1-326 | 4-a1 | CH$_2$ | h3 | & NMR |
| B-1-327 | 4-a1 | CO | h4 | |
| B-1-328 | 4-a1 | CH$_2$ | h4 | |
| B-1-329 | 4-a1 | CO | h5 | |
| B-1-330 | 4-a1 | CH$_2$ | h5 | |
| B-1-331 | 4-a1 | CO | h6 | |
| B-1-332 | 4-a1 | CH$_2$ | h6 | & NMR |
| B-1-333 | 4-a1 | CO | h7 | |
| B-1-334 | 4-a1 | CH$_2$ | h7 | |
| B-1-335 | 4-a1 | CO | h8 | |
| B-1-336 | 4-a1 | CH$_2$ | h8 | |
| B-1-337 | 3-a1 | CO | h1 | |
| B-1-338 | 3-a1 | CH$_2$ | h1 | |
| B-1-339 | 3-a1 | CO | h2 | |
| B-1-340 | 3-a1 | CH$_2$ | h2 | |
| B-1-341 | 3-a1 | CO | h3 | |
| B-1-342 | 3-a1 | CH$_2$ | h3 | |
| B-1-343 | 3-a1 | CO | h4 | |
| B-1-344 | 3-a1 | CH$_2$ | h4 | |
| B-1-345 | 3-a1 | CO | h5 | |
| B-1-346 | 3-a1 | CH$_2$ | h5 | |
| B-1-347 | 3-a1 | CO | h6 | |
| B-1-348 | 3-a1 | CH$_2$ | h6 | |
| B-1-349 | 3-a1 | CO | h7 | |
| B-1-350 | 3-a1 | CH$_2$ | h7 | |
| B-1-351 | 3-a1 | CO | h8 | |
| B-1-352 | 3-a1 | CH$_2$ | h8 | |
| B-1-353 | 4-a2 | CO | h1 | |
| B-1-354 | 4-a2 | CH$_2$ | h1 | |
| B-1-355 | 4-a2 | CO | h2 | |
| B-1-356 | 4-a2 | CH$_2$ | h2 | |
| B-1-357 | 4-a2 | CO | h3 | |
| B-1-358 | 4-a2 | CH$_2$ | h3 | |
| B-1-359 | 4-a2 | CO | h4 | |
| B-1-360 | 4-a2 | CH$_2$ | h4 | |
| B-1-361 | 4-a2 | CO | h5 | |
| B-1-362 | 4-a2 | CH$_2$ | h5 | |
| B-1-363 | 4-a2 | CO | h6 | |
| B-1-364 | 4-a2 | CH$_2$ | h6 | |
| B-1-365 | 4-a2 | CO | h7 | |
| B-1-366 | 4-a2 | CH$_2$ | h7 | |
| B-1-367 | 4-a2 | CO | h8 | |
| B-1-368 | 4-a2 | CH$_2$ | h8 | |
| B-1-369 | 3-a2 | CO | h1 | |
| B-1-370 | 3-a2 | CH$_2$ | h1 | |
| B-1-371 | 3-a2 | CO | h2 | |
| B-1-372 | 3-a2 | CH$_2$ | h2 | |
| B-1-373 | 3-a2 | CO | h3 | |
| B-1-374 | 3-a2 | CH$_2$ | h3 | |
| B-1-375 | 3-a2 | CO | h4 | |
| B-1-376 | 3-a2 | CH$_2$ | h4 | |
| B-1-377 | 3-a2 | CO | h5 | |
| B-1-378 | 3-a2 | CH$_2$ | h5 | |
| B-1-379 | 3-a2 | CO | h6 | |
| B-1-380 | 3-a2 | CH$_2$ | h6 | |
| B-1-381 | 3-a2 | CO | h7 | |
| B-1-382 | 3-a2 | CH$_2$ | h7 | |
| B-1-383 | 3-a2 | CO | h8 | |
| B-1-384 | 3-a2 | CH$_2$ | h8 | |

TABLE 7

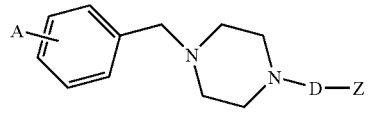

| Compound No. | A | D | Z | Physical Constant [ ] m.p. ° C. |
|---|---|---|---|---|
| B-1-385 | 4-a1 | CO | h1 | [245] (decomp.) |
| B-1-386 | 4-a1 | CH$_2$ | h1 | $n_D^{20.6}$1.5646 |
| B-1-387 | 4-a1 | CO | h2 | |
| B-1-388 | 4-a1 | CH$_2$ | h2 | |
| B-1-389 | 4-a1 | CO | h3 | |
| B-1-390 | 4-a1 | CH$_2$ | h3 | |
| B-1-391 | 4-a1 | CO | h4 | |
| B-1-392 | 4-a1 | CH$_2$ | h4 | |
| B-1-393 | 4-a1 | CO | h5 | |
| B-1-394 | 4-a1 | CH$_2$ | h5 | |
| B-1-395 | 4-a1 | CO | h6 | |
| B-1-396 | 4-a1 | CH$_2$ | h6 | $n_D^{21.2}$1.5329 |
| B-1-397 | 4-a1 | CO | h7 | |
| B-1-398 | 4-a1 | CH$_2$ | h7 | |
| B-1-399 | 4-a1 | CO | h8 | |
| B-1-400 | 4-a1 | CH$_2$ | h8 | |
| B-1-401 | 3-a1 | CO | h1 | |
| B-1-402 | 3-a1 | CH$_2$ | h1 | |
| B-1-403 | 3-a1 | CO | h2 | |
| B-1-404 | 3-a1 | CH$_2$ | h2 | |
| B-1-405 | 3-a1 | CO | h3 | |
| B-1-406 | 3-a1 | CH$_2$ | h3 | |
| B-1-407 | 3-a1 | CO | h4 | |
| B-1-408 | 3-a1 | CH$_2$ | h4 | |
| B-1-409 | 3-a1 | CO | h5 | |
| B-1-410 | 3-a1 | CH$_2$ | h5 | |
| B-1-411 | 3-a1 | CO | h6 | |
| B-1-412 | 3-a1 | CH$_2$ | h6 | |
| B-1-413 | 3-a1 | CO | h7 | |
| B-1-414 | 3-a1 | CH$_2$ | h7 | |
| B-1-415 | 3-a1 | CO | h8 | |
| B-1-416 | 3-a1 | CH$_2$ | h8 | |
| B-1-417 | 4-a2 | CO | h1 | |
| B-1-418 | 4-a2 | CH$_2$ | h1 | |
| B-1-419 | 4-a2 | CO | h2 | |
| B-1-420 | 4-a2 | CH$_2$ | h2 | |
| B-1-421 | 4-a2 | CO | h3 | |
| B-1-422 | 4-a2 | CH$_2$ | h3 | |
| B-1-423 | 4-a2 | CO | h4 | |
| B-1-424 | 4-a2 | CH$_2$ | h4 | |
| B-1-425 | 4-a2 | CO | h5 | |
| B-1-426 | 4-a2 | CH$_2$ | h5 | |
| B-1-427 | 4-a2 | CO | h6 | |
| B-1-428 | 4-a2 | CH$_2$ | h6 | |
| B-1-429 | 4-a2 | CO | h7 | |
| B-1-430 | 4-a2 | CH$_2$ | h7 | |
| B-1-431 | 4-a2 | CO | h8 | |
| B-1-432 | 4-a2 | CH$_2$ | h8 | |
| B-1-433 | 3-a2 | CO | h1 | |
| B-1-434 | 3-a2 | CH$_2$ | h1 | |
| B-1-435 | 3-a2 | CO | h2 | |
| B-1-436 | 3-a2 | CH$_2$ | h2 | |
| B-1-437 | 3-a2 | CO | h3 | |
| B-1-438 | 3-a2 | CH$_2$ | h3 | |
| B-1-439 | 3-a2 | CO | h4 | |
| B-1-440 | 3-a2 | CH$_2$ | h4 | |
| B-1-441 | 3-a2 | CO | h5 | |
| B-1-442 | 3-a2 | CH$_2$ | h5 | |
| B-1-443 | 3-a2 | CO | h6 | |
| B-1-444 | 3-a2 | CH$_2$ | h6 | |
| B-1-445 | 3-a2 | CO | h7 | |
| B-1-446 | 3-a2 | CH$_2$ | h7 | |
| B-1-447 | 3-a2 | CO | h8 | |
| B-1-448 | 3-a2 | CH$_2$ | h8 | |

TABLE 8

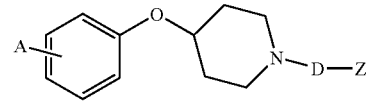

| Compound No. | A | D | Z | Physical Constant [ ] m.p. ° C. |
|---|---|---|---|---|
| B-1-449 | 4-a1 | CO | h1 | |
| B-1-450 | 4-a1 | CH$_2$ | h1 | $n_D^{20.7}$1.5376 |
| B-1-451 | 4-a1 | CO | h2 | |
| B-1-452 | 4-a1 | CH$_2$ | h2 | |
| B-1-453 | 4-a1 | CO | h3 | |
| B-1-454 | 4-a1 | CH$_2$ | h3 | |
| B-1-455 | 4-a1 | CO | h4 | |
| B-1-456 | 4-a1 | CH$_2$ | h4 | |
| B-1-457 | 4-a1 | CO | h5 | |
| B-1-458 | 4-a1 | CH$_2$ | h5 | |
| B-1-459 | 4-a1 | CO | h6 | |
| B-1-460 | 4-a1 | CH$_2$ | h6 | $n_D^{20.7}$1.5307 |
| B-1-461 | 4-a1 | CO | h7 | |
| B-1-462 | 4-a1 | CH$_2$ | h7 | |
| B-1-463 | 4-a1 | CO | h8 | |
| B-1-464 | 4-a1 | CH$_2$ | h8 | |
| B-1-465 | 3-a1 | CO | h1 | |
| B-1-466 | 3-a1 | CH$_2$ | h1 | |
| B-1-467 | 3-a1 | CO | h2 | |
| B-1-468 | 3-a1 | CH$_2$ | h2 | |
| B-1-469 | 3-a1 | CO | h3 | |
| B-1-470 | 3-a1 | CH$_2$ | h3 | |
| B-1-471 | 3-a1 | CO | h4 | |
| B-1-472 | 3-a1 | CH$_2$ | h4 | |
| B-1-473 | 3-a1 | CO | h5 | |
| B-1-474 | 3-a1 | CH$_2$ | h5 | |
| B-1-475 | 3-a1 | CO | h6 | |
| B-1-476 | 3-a1 | CH$_2$ | h6 | |
| B-1-477 | 3-a1 | CO | h7 | |
| B-1-478 | 3-a1 | CH$_2$ | h7 | |
| B-1-479 | 3-a1 | CO | h8 | |
| B-1-480 | 3-a1 | CH$_2$ | h8 | |
| B-1-481 | 4-a2 | CO | h1 | |
| B-1-482 | 4-a2 | CH$_2$ | h1 | |
| B-1-483 | 4-a2 | CO | h2 | |
| B-1-484 | 4-a2 | CH$_2$ | h2 | |
| B-1-485 | 4-a2 | CO | h3 | |
| B-1-486 | 4-a2 | CH$_2$ | h3 | |
| B-1-487 | 4-a2 | CO | h4 | |
| B-1-488 | 4-a2 | CH$_2$ | h4 | |
| B-1-489 | 4-a2 | CO | h5 | |
| B-1-490 | 4-a2 | CH$_2$ | h5 | |
| B-1-491 | 4-a2 | CO | h6 | |
| B-1-492 | 4-a2 | CH$_2$ | h6 | |
| B-1-493 | 4-a2 | CO | h7 | |
| B-1-494 | 4-a2 | CH$_2$ | h7 | |
| B-1-495 | 4-a2 | CO | h8 | |
| B-1-496 | 4-a2 | CH$_2$ | h8 | |
| B-1-497 | 3-a2 | CO | h1 | |
| B-1-498 | 3-a2 | CH$_2$ | h1 | |
| B-1-499 | 3-a2 | CO | h2 | |
| B-1-500 | 3-a2 | CH$_2$ | h2 | |
| B-1-501 | 3-a2 | CO | h3 | |
| B-1-502 | 3-a2 | CH$_2$ | h3 | |
| B-1-503 | 3-a2 | CO | h4 | |
| B-1-504 | 3-a2 | CH$_2$ | h4 | |
| B-1-505 | 3-a2 | CO | h5 | |
| B-1-506 | 3-a2 | CH$_2$ | h5 | |
| B-1-507 | 3-a2 | CO | h6 | |
| B-1-508 | 3-a2 | CH$_2$ | h6 | |
| B-1-509 | 3-a2 | CO | h7 | |
| B-1-510 | 3-a2 | CH$_2$ | h7 | |
| B-1-511 | 3-a2 | CO | h8 | |
| B-1-512 | 3-a2 | CH$_2$ | h8 | |

TABLE 9

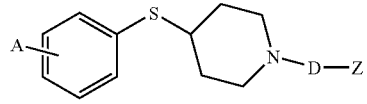

| Compound No. | A | D | Z | Physical Constant [ ] m.p. ° C. |
|---|---|---|---|---|
| B-1-513 | 4-a1 | CO | h1 | |
| B-1-514 | 4-a1 | CH$_2$ | h1 | |
| B-1-515 | 4-a1 | CO | h2 | |
| B-1-516 | 4-a1 | CH$_2$ | h2 | |
| B-1-517 | 4-a1 | CO | h3 | |
| B-1-518 | 4-a1 | CH$_2$ | h3 | |
| B-1-519 | 4-a1 | CO | h4 | |
| B-1-520 | 4-a1 | CH$_2$ | h4 | |
| B-1-521 | 4-a1 | CO | h5 | |
| B-1-522 | 4-a1 | CH$_2$ | h5 | |
| B-1-523 | 4-a1 | CO | h6 | |
| B-1-524 | 4-a1 | CH$_2$ | h6 | |
| B-1-525 | 4-a1 | CO | h7 | |
| B-1-526 | 4-a1 | CH$_2$ | h7 | |
| B-1-527 | 4-a1 | CO | h8 | |
| B-1-528 | 4-a1 | CH$_2$ | h8 | |
| B-1-529 | 3-a1 | CO | h1 | |
| B-1-530 | 3-a1 | CH$_2$ | h1 | |
| B-1-531 | 3-a1 | CO | h2 | |
| B-1-532 | 3-a1 | CH$_2$ | h2 | |
| B-1-533 | 3-a1 | CO | h3 | |
| B-1-534 | 3-a1 | CH$_2$ | h3 | |
| B-1-535 | 3-a1 | CO | h4 | |
| B-1-536 | 3-a1 | CH$_2$ | h4 | |
| B-1-537 | 3-a1 | CO | h5 | |
| B-1-538 | 3-a1 | CH$_2$ | h5 | |
| B-1-539 | 3-a1 | CO | h6 | |
| B-1-540 | 3-a1 | CH$_2$ | h6 | |
| B-1-541 | 3-a1 | CO | h7 | |
| B-1-542 | 3-a1 | CH$_2$ | h7 | |
| B-1-543 | 3-a1 | CO | h8 | |
| B-1-544 | 3-a1 | CH$_2$ | h8 | |
| B-1-545 | 4-a2 | CO | h1 | |
| B-1-546 | 4-a2 | CH$_2$ | h1 | |
| B-1-547 | 4-a2 | CO | h2 | |
| B-1-548 | 4-a2 | CH$_2$ | h2 | |
| B-1-549 | 4-a2 | CO | h3 | |
| B-1-550 | 4-a2 | CH$_2$ | h3 | |
| B-1-551 | 4-a2 | CO | h4 | |
| B-1-552 | 4-a2 | CH$_2$ | h4 | |
| B-1-553 | 4-a2 | CO | h5 | |
| B-1-554 | 4-a2 | CH$_2$ | h5 | |
| B-1-555 | 4-a2 | CO | h6 | |
| B-1-556 | 4-a2 | CH$_2$ | h6 | |
| B-1-557 | 4-a2 | CO | h7 | |
| B-1-558 | 4-a2 | CH$_2$ | h7 | |
| B-1-559 | 4-a2 | CO | h8 | |
| B-1-560 | 4-a2 | CH$_2$ | h8 | |
| B-1-561 | 3-a2 | CO | h1 | |
| B-1-562 | 3-a2 | CH$_2$ | h1 | |
| B-1-563 | 3-a2 | CO | h2 | |
| B-1-564 | 3-a2 | CH$_2$ | h2 | |
| B-1-565 | 3-a2 | CO | h3 | |
| B-1-566 | 3-a2 | CH$_2$ | h3 | |
| B-1-567 | 3-a2 | CO | h4 | |
| B-1-568 | 3-a2 | CH$_2$ | h4 | |
| B-1-569 | 3-a2 | CO | h5 | |
| B-1-570 | 3-a2 | CH$_2$ | h5 | |
| B-1-571 | 3-a2 | CO | h6 | |
| B-1-572 | 3-a2 | CH$_2$ | h6 | |
| B-1-573 | 3-a2 | CO | h7 | |
| B-1-574 | 3-a2 | CH$_2$ | h7 | |
| B-1-575 | 3-a2 | CO | h8 | |
| B-1-576 | 3-a2 | CH$_2$ | h8 | |

TABLE 10

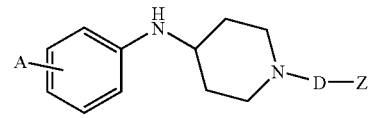

| Compound No. | A | D | Z | Physical Constant [ ] m.p. ° C. |
|---|---|---|---|---|
| B-1-577 | 4-a1 | CO | h1 | |
| B-1-578 | 4-a1 | CH$_2$ | h1 | $n_D^{20.5}$1.5668 |
| B-1-579 | 4-a1 | CO | h2 | |
| B-1-580 | 4-a1 | CH$_2$ | h2 | |
| B-1-581 | 4-a1 | CO | h3 | |
| B-1-582 | 4-a1 | CH$_2$ | h3 | |
| B-1-583 | 4-a1 | CO | h4 | |
| B-1-584 | 4-a1 | CH$_2$ | h4 | |
| B-1-585 | 4-a1 | CO | h5 | |
| B-1-586 | 4-a1 | CH$_2$ | h5 | |
| B-1-587 | 4-a1 | CO | h6 | |
| B-1-588 | 4-a1 | CH$_2$ | h6 | |
| B-1-589 | 4-a1 | CO | h7 | |
| B-1-590 | 4-a1 | CH$_2$ | h7 | |
| B-1-591 | 4-a1 | CO | h8 | |
| B-1-592 | 4-a1 | CH$_2$ | h8 | |
| B-1-593 | 3-a1 | CO | h1 | |
| B-1-594 | 3-a1 | CH$_2$ | h1 | |
| B-1-595 | 3-a1 | CO | h2 | |
| B-1-596 | 3-a1 | CH$_2$ | h2 | |
| B-1-597 | 3-a1 | CO | h3 | |
| B-1-598 | 3-a1 | CH$_2$ | h3 | |
| B-1-599 | 3-a1 | CO | h4 | |
| B-1-600 | 3-a1 | CH$_2$ | h4 | |
| B-1-601 | 3-a1 | CO | h5 | |
| B-1-602 | 3-a1 | CH$_2$ | h5 | |
| B-1-603 | 3-a1 | CO | h6 | |
| B-1-604 | 3-a1 | CH$_2$ | h6 | |
| B-1-605 | 3-a1 | CO | h7 | |
| B-1-606 | 3-a1 | CH$_2$ | h7 | |
| B-1-607 | 3-a1 | CO | h8 | |
| B-1-608 | 3-a1 | CH$_2$ | h8 | |
| B-1-609 | 4-a2 | CO | h1 | |
| B-1-610 | 4-a2 | CH$_2$ | h1 | |
| B-1-611 | 4-a2 | CO | h2 | |
| B-1-612 | 4-a2 | CH$_2$ | h2 | |
| B-1-613 | 4-a2 | CO | h3 | |
| B-1-614 | 4-a2 | CH$_2$ | h3 | |
| B-1-615 | 4-a2 | CO | h4 | |
| B-1-616 | 4-a2 | CH$_2$ | h4 | |
| B-1-617 | 4-a2 | CO | h5 | |
| B-1-618 | 4-a2 | CH$_2$ | h5 | |
| B-1-619 | 4-a2 | CO | h6 | |
| B-1-620 | 4-a2 | CH$_2$ | h6 | |
| B-1-621 | 4-a2 | CO | h7 | |
| B-1-622 | 4-a2 | CH$_2$ | h7 | |
| B-1-623 | 4-a2 | CO | h8 | |
| B-1-624 | 4-a2 | CH$_2$ | h8 | |
| B-1-625 | 3-a2 | CO | h1 | |
| B-1-626 | 3-a2 | CH$_2$ | h1 | |
| B-1-627 | 3-a2 | CO | h2 | |
| B-1-628 | 3-a2 | CH$_2$ | h2 | |
| B-1-629 | 3-a2 | CO | h3 | |
| B-1-630 | 3-a2 | CH$_2$ | h3 | |
| B-1-631 | 3-a2 | CO | h4 | |
| B-1-632 | 3-a2 | CH$_2$ | h4 | |
| B-1-633 | 3-a2 | CO | h5 | |
| B-1-634 | 3-a2 | CH$_2$ | h5 | |
| B-1-635 | 3-a2 | CO | h6 | |
| B-1-636 | 3-a2 | CH$_2$ | h6 | |
| B-1-637 | 3-a2 | CO | h7 | |
| B-1-638 | 3-a2 | CH$_2$ | h7 | |
| B-1-639 | 3-a2 | CO | h8 | |
| B-1-640 | 3-a2 | CH$_2$ | h8 | |

TABLE 11

| Compound No. | R9 | R4 | R1a | R1b | D | Z | Physical Constant [ ] m.p. °C. nD refractive index |
|---|---|---|---|---|---|---|---|
| B-2-1-1 | H | H | H | H | CH2 | h1 | $n_D^{20.4}$1.5693 |
| B-2-1-2 | H | H | H | H | CH2 | h2 | [50-52] |
| B-2-1-3 | H | H | H | H | CH2 | h3 | [81-84] |
| B-2-1-4 | H | H | H | H | CH2 | h4 | & NMR |
| B-2-1-5 | H | H | H | H | CH2 | h5 | [158-160] |
| B-2-1-6 | H | H | H | H | CH2 | h6 | $n_D^{20.1}$1.5531 |
| B-2-1-7 | H | H | H | H | CH2 | h7 | $n_D^{20.7}$1.5472 |
| B-2-1-8 | H | H | H | H | CH2 | h8 | [90-93] |
| B-2-1-9 | H | H | H | H | CH2CH2 | h1 | |
| B-2-1-10 | H | H | H | H | CH2CH2 | h2 | |
| B-2-1-11 | H | H | H | H | CH2CH2 | h3 | |
| B-2-1-12 | H | H | H | H | CH2CH2 | h4 | |
| B-2-1-13 | H | H | H | H | CH2CH2 | h5 | |
| B-2-1-14 | H | H | H | H | CH2CH2 | h6 | |
| B-2-1-15 | H | H | H | H | CH2CH2 | h7 | |
| B-2-1-16 | H | H | H | H | CH2CH2 | h8 | |
| B-2-1-17 | H | H | H | H | CH2CH2CH2 | h1 | |
| B-2-1-18 | H | H | H | H | CH2CH2CH2 | h2 | |
| B-2-1-19 | H | H | H | H | CH2CH2CH2 | h3 | |
| B-2-1-20 | H | H | H | H | CH2CH2CH2 | h4 | |
| B-2-1-21 | H | H | H | H | CH2CH2CH2 | h5 | |
| B-2-1-22 | H | H | H | H | CH2CH2CH2 | h6 | & NMR |
| B-2-1-23 | H | H | H | H | CH2CH2CH2 | h7 | |
| B-2-1-24 | H | H | H | H | CH2CH2CH2 | h8 | |
| B-2-1-25 | H | H | H | H | CH2CH2CH2CH2CH2CH2 | h1 | |
| B-2-1-26 | H | H | H | H | CH2CH2CH2CH2CH2CH2 | h2 | |
| B-2-1-27 | H | H | H | H | CH2CH2CH2CH2CH2CH2 | h3 | |
| B-2-1-28 | H | H | H | H | CH2CH2CH2CH2CH2CH2 | h4 | |
| B-2-1-29 | H | H | H | H | CH2CH2CH2CH2CH2CH2 | h5 | |
| B-2-1-30 | H | H | H | H | CH2CH2CH2CH2CH2CH2 | h6 | $n_D^{21.4}$1.5379 |
| B-2-1-31 | H | H | H | H | CH2CH2CH2CH2CH2CH2 | h7 | |
| B-2-1-32 | H | H | H | H | CH2CH2CH2CH2CH2CH2 | h8 | |
| B-2-1-33 | CH3 | H | H | H | CH2 | h1 | |
| B-2-1-34 | CH3 | H | H | H | CH2 | h2 | |
| B-2-1-35 | CH3 | H | H | H | CH2 | h3 | |
| B-2-1-36 | CH3 | H | H | H | CH2 | h4 | |
| B-2-1-37 | CH3 | H | H | H | CH2 | h5 | |
| B-2-1-38 | CH3 | H | H | H | CH2 | h6 | |
| B-2-1-39 | CH3 | H | H | H | CH2 | h7 | |
| B-2-1-40 | CH3 | H | H | H | CH2 | h8 | |
| B-2-1-41 | CH2CH3 | H | H | H | CH2 | h1 | |
| B-2-1-42 | CH2CH3 | H | H | H | CH2 | h2 | |
| B-2-1-43 | CH2CH3 | H | H | H | CH2 | h3 | |
| B-2-1-44 | CH2CH3 | H | H | H | CH2 | h4 | |
| B-2-1-45 | CH2CH3 | H | H | H | CH2 | h5 | |
| B-2-1-46 | CH2CH3 | H | H | H | CH2 | h6 | |
| B-2-1-47 | CH2CH3 | H | H | H | CH2 | h7 | |
| B-2-1-48 | CH2CH3 | H | H | H | CH2 | h8 | |
| B-2-1-49 | CH2CH2CH3 | H | H | H | CH2 | h1 | |
| B-2-1-50 | CH2CH2CH3 | H | H | H | CH2 | h2 | |
| B-2-1-51 | CH2CH2CH3 | H | H | H | CH2 | h3 | |
| B-2-1-52 | CH2CH2CH3 | H | H | H | CH2 | h4 | |
| B-2-1-53 | CH2CH2CH3 | H | H | H | CH2 | h5 | |
| B-2-1-54 | CH2CH2CH3 | H | H | H | CH2 | h6 | |
| B-2-1-55 | CH2CH2CH3 | H | H | H | CH2 | h7 | |
| B-2-1-56 | CH2CH2CH3 | H | H | H | CH2 | h8 | |
| B-2-1-57 | CH(CH3)2 | H | H | H | CH2 | h1 | |
| B-2-1-58 | CH(CH3)2 | H | H | H | CH2 | h2 | |
| B-2-1-59 | CH(CH3)2 | H | H | H | CH2 | h3 | |
| B-2-1-60 | CH(CH3)2 | H | H | H | CH2 | h4 | |
| B-2-1-61 | CH(CH3)2 | H | H | H | CH2 | h5 | |
| B-2-1-62 | CH(CH3)2 | H | H | H | CH2 | h6 | |
| B-2-1-63 | CH(CH3)2 | H | H | H | CH2 | h7 | |
| B-2-1-64 | CH(CH3)2 | H | H | H | CH2 | h8 | |
| B-2-1-65 | CH2C6H5 | H | H | H | CH2 | h1 | |
| B-2-1-66 | CH2C6H5 | H | H | H | CH2 | h2 | |
| B-2-1-67 | CH2C6H5 | H | H | H | CH2 | h3 | |

TABLE 11-continued

| Compound No. | R9 | R4 | R1a | R1b | D | Z | Physical Constant [ ] m.p. ° C. nD refractive index |
|---|---|---|---|---|---|---|---|
| B-2-1-68 | CH2C6H5 | H | H | H | CH2 | h4 | |
| B-2-1-69 | CH2C6H5 | H | H | H | CH2 | h5 | |
| B-2-1-70 | CH2C6H5 | H | H | H | CH2 | h6 | |
| B-2-1-71 | CH2C6H5 | H | H | H | CH2 | h7 | |
| B-2-1-72 | CH2C6H5 | H | H | H | CH2 | h8 | |
| B-2-1-73 | H | CH3 | H | H | CH2 | h1 | [78-81] |
| B-2-1-74 | H | CH3 | H | H | CH2 | h2 | |
| B-2-1-75 | H | CH3 | H | H | CH2 | h3 | |
| B-2-1-76 | H | CH3 | H | H | CH2 | h4 | |
| B-2-1-77 | H | CH3 | H | H | CH2 | h5 | |
| B-2-1-78 | H | CH3 | H | H | CH2 | h6 | |
| B-2-1-79 | H | CH3 | H | H | CH2 | h7 | |
| B-2-1-80 | H | CH3 | H | H | CH2 | h8 | |
| B-2-1-81 | H | H | CH3 | H | CH2 | h1 | |
| B-2-1-82 | H | H | CH3 | H | CH2 | h2 | |
| B-2-1-83 | H | H | CH3 | H | CH2 | h3 | |
| B-2-1-84 | H | H | CH3 | H | CH2 | h4 | |
| B-2-1-85 | H | H | CH3 | H | CH2 | h5 | |
| B-2-1-86 | H | H | CH3 | H | CH2 | h6 | |
| B-2-1-87 | H | H | CH3 | H | CH2 | h7 | |
| B-2-1-88 | H | H | CH3 | H | CH2 | h8 | |
| B-2-1-89 | H | H | Cl | H | CH2 | h1 | |
| B-2-1-90 | H | H | Cl | H | CH2 | h2 | |
| B-2-1-91 | H | H | Cl | H | CH2 | h3 | |
| B-2-1-92 | H | H | Cl | H | CH2 | h4 | |
| B-2-1-93 | H | H | Cl | H | CH2 | h5 | |
| B-2-1-94 | H | H | Cl | H | CH2 | h6 | |
| B-2-1-95 | H | H | Cl | H | CH2 | h7 | |
| B-2-1-96 | H | H | Cl | H | CH2 | h8 | |
| B-2-1-97 | H | H | F | H | CH2 | h1 | |
| B-2-1-98 | H | H | F | H | CH2 | h2 | |
| B-2-1-99 | H | H | F | H | CH2 | h3 | |
| B-2-1-100 | H | H | F | H | CH2 | h4 | |
| B-2-1-101 | H | H | F | H | CH2 | h5 | |
| B-2-1-102 | H | H | F | H | CH2 | h6 | |
| B-2-1-103 | H | H | F | H | CH2 | h7 | |
| B-2-1-104 | H | H | F | H | CH2 | h8 | |
| B-2-1-105 | H | H | H | CH3 | CH2 | h1 | [156-158] |
| B-2-1-106 | H | H | H | CH3 | CH2 | h2 | |
| B-2-1-107 | H | H | H | CH3 | CH2 | h3 | |
| B-2-1-108 | H | H | H | CH3 | CH2 | h4 | |
| B-2-1-109 | H | H | H | CH3 | CH2 | h5 | |
| B-2-1-110 | H | H | H | CH3 | CH2 | h6 | |
| B-2-1-111 | H | H | H | CH3 | CH2 | h7 | |
| B-2-1-112 | H | H | H | CH3 | CH2 | h8 | |
| B-2-1-113 | H | H | H | Cl | CH2 | h1 | |
| B-2-1-114 | H | H | H | Cl | CH2 | h2 | |
| B-2-1-115 | H | H | H | Cl | CH2 | h3 | |
| B-2-1-116 | H | H | H | Cl | CH2 | h4 | |
| B-2-1-117 | H | H | H | Cl | CH2 | h5 | |
| B-2-1-118 | H | H | H | Cl | CH2 | h6 | |
| B-2-1-119 | H | H | H | Cl | CH2 | h7 | |
| B-2-1-120 | H | H | H | Cl | CH2 | h8 | |
| B-2-1-121 | H | H | H | F | CH2 | h1 | |
| B-2-1-122 | H | H | H | F | CH2 | h2 | |
| B-2-1-123 | H | H | H | F | CH2 | h3 | |
| B-2-1-124 | H | H | H | F | CH2 | h4 | |
| B-2-1-125 | H | H | H | F | CH2 | h5 | |
| B-2-1-126 | H | H | H | F | CH2 | h6 | |
| B-2-1-127 | H | H | H | F | CH2 | h7 | |
| B-2-1-128 | H | H | H | F | CH2 | h8 | |

TABLE 12

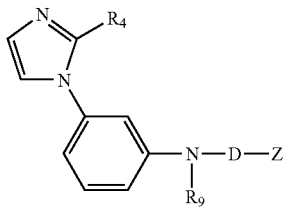

| Compound No. | R₉ | R₄ | D | Z | Physical Constant [ ] m.p. °C. $n_D$ refractive index |
|---|---|---|---|---|---|
| B-2-2-1 | H | H | CH₂ | H1 | [211-216] |
| B-2-2-2 | H | H | CH₂ | h2 | & NMR |
| B-2-2-3 | H | H | CH₂ | h3 | [175-178] |
| B-2-2-4 | H | H | CH₂ | h4 | |
| B-2-2-5 | H | H | CH₂ | h5 | [63-66] |
| B-2-2-6 | H | H | CH₂ | h6 | $n_D^{20.5}$ 1.5529 |
| B-2-2-7 | H | H | CH₂ | h7 | |
| B-2-2-8 | H | H | CH₂ | h8 | |
| B-2-2-9 | H | H | CH₂CH₂ | h1 | |
| B-2-2-10 | H | H | CH₂CH₂ | h2 | |
| B-2-2-11 | H | H | CH₂CH₂ | h3 | |
| B-2-2-12 | H | H | CH₂CH₂ | h4 | |
| B-2-2-13 | H | H | CH₂CH₂ | h5 | |
| B-2-2-14 | H | H | CH₂CH₂ | h6 | |
| B-2-2-15 | H | H | CH₂CH₂ | h7 | |
| B-2-2-16 | H | H | CH₂CH₂ | h8 | |
| B-2-2-17 | H | H | CH₂CH₂CH₂ | h1 | |
| B-2-2-18 | H | H | CH₂CH₂CH₂ | h2 | |
| B-2-2-19 | H | H | CH₂CH₂CH₂ | h3 | |
| B-2-2-20 | H | H | CH₂CH₂CH₂ | h4 | |
| B-2-2-21 | H | H | CH₂CH₂CH₂ | h5 | |
| B-2-2-22 | H | H | CH₂CH₂CH₂ | h6 | |
| B-2-2-23 | H | H | CH₂CH₂CH₂ | h7 | |
| B-2-2-24 | H | H | CH₂CH₂CH₂ | h8 | |
| B-2-2-25 | H | H | CH₂CH₂CH₂CH₂CH₂CH₂ | h1 | |
| B-2-2-26 | H | H | CH₂CH₂CH₂CH₂CH₂CH₂ | h2 | |
| B-2-2-27 | H | H | CH₂CH₂CH₂CH₂CH₂CH₂ | h3 | |
| B-2-2-28 | H | H | CH₂CH₂CH₂CH₂CH₂CH₂ | h4 | |
| B-2-2-29 | H | H | CH₂CH₂CH₂CH₂CH₂CH₂ | h5 | |
| B-2-2-30 | H | H | CH₂CH₂CH₂CH₂CH₂CH₂ | h6 | |
| B-2-2-31 | H | H | CH₂CH₂CH₂CH₂CH₂CH₂ | h7 | |
| B-2-2-32 | H | H | CH₂CH₂CH₂CH₂CH₂CH₂ | h8 | |
| B-2-2-33 | CH₃ | H | CH₂ | h1 | |
| B-2-2-34 | CH₃ | H | CH₂ | h2 | |
| B-2-2-35 | CH₃ | H | CH₂ | h3 | |
| B-2-2-36 | CH₃ | H | CH₂ | h4 | |
| B-2-2-37 | CH₃ | H | CH₂ | h5 | |
| B-2-2-38 | CH₃ | H | CH₂ | h6 | |
| B-2-2-39 | CH₃ | H | CH₂ | h7 | |
| B-2-2-40 | CH₃ | H | CH₂ | h8 | |
| B-2-2-41 | CH₂CH₃ | H | CH₂ | h1 | |
| B-2-2-42 | CH₂CH₃ | H | CH₂ | h2 | |
| B-2-2-43 | CH₂CH₃ | H | CH₂ | h3 | |
| B-2-2-44 | CH₂CH₃ | H | CH₂ | h4 | |
| B-2-2-45 | CH₂CH₃ | H | CH₂ | h5 | |
| B-2-2-46 | CH₂CH₃ | H | CH₂ | h6 | |
| B-2-2-47 | CH₂CH₃ | H | CH₂ | h7 | |
| B-2-2-48 | CH₂CH₃ | H | CH₂ | h8 | |
| B-2-2-49 | CH₂CH₂CH₃ | H | CH₂ | h1 | |
| B-2-2-50 | CH₂CH₂CH₃ | H | CH₂ | h2 | |
| B-2-2-51 | CH₂CH₂CH₃ | H | CH₂ | h3 | |
| B-2-2-52 | CH₂CH₂CH₃ | H | CH₂ | h4 | |
| B-2-2-53 | CH₂CH₂CH₃ | H | CH₂ | h5 | |
| B-2-2-54 | CH₂CH₂CH₃ | H | CH₂ | h6 | |
| B-2-2-55 | CH₂CH₂CH₃ | H | CH₂ | h7 | |
| B-2-2-56 | CH₂CH₂CH₃ | H | CH₂ | h8 | |
| B-2-2-57 | CH(CH₃)₂ | H | CH₂ | h1 | |
| B-2-2-58 | CH(CH₃)₂ | H | CH₂ | h2 | |
| B-2-2-59 | CH(CH₃)₂ | H | CH₂ | h3 | |
| B-2-2-60 | CH(CH₃)₂ | H | CH₂ | h4 | |
| B-2-2-61 | CH(CH₃)₂ | H | CH₂ | h5 | |
| B-2-2-62 | CH(CH₃)₂ | H | CH₂ | h6 | |
| B-2-2-63 | CH(CH₃)₂ | H | CH₂ | h7 | |
| B-2-2-64 | CH(CH₃)₂ | H | CH₂ | h8 | |

TABLE 12-continued

| Compound No. | R9 | R4 | D | Z | Physical Constant [ ] m.p. ° C. $n_D$ refractive index |
|---|---|---|---|---|---|
| B-2-2-65 | $CH_2C_6H_5$ | H | $CH_2$ | h1 | |
| B-2-2-66 | $CH_2C_6H_5$ | H | $CH_2$ | h2 | |
| B-2-2-67 | $CH_2C_6H_5$ | H | $CH_2$ | h3 | |
| B-2-2-68 | $CH_2C_6H_5$ | H | $CH_2$ | h4 | |
| B-2-2-69 | $CH_2C_6H_5$ | H | $CH_2$ | h5 | |
| B-2-2-70 | $CH_2C_6H_5$ | H | $CH_2$ | h6 | |
| B-2-2-71 | $CH_2C_6H_5$ | H | $CH_2$ | h7 | |
| B-2-2-72 | $CH_2C_6H_5$ | H | $CH_2$ | h8 | |
| B-2-2-73 | H | $CH_3$ | $CH_2$ | h1 | |
| B-2-2-74 | H | $CH_3$ | $CH_2$ | h2 | |
| B-2-2-75 | H | $CH_3$ | $CH_2$ | h3 | |
| B-2-2-76 | H | $CH_3$ | $CH_2$ | h4 | |
| B-2-2-77 | H | $CH_3$ | $CH_2$ | h5 | |
| B-2-2-78 | H | $CH_3$ | $CH_2$ | h6 | |
| B-2-2-79 | H | $CH_3$ | $CH_2$ | h7 | |
| B-2-2-80 | H | $CH_3$ | $CH_2$ | h8 | |

TABLE 13

| Compound No. | R9 | R6 | R1a | R1b | D | Z | Physical Constant [ ] m.p. ° C. $n_D$ refractive index |
|---|---|---|---|---|---|---|---|
| B-2-3-1 | H | H | H | H | $CH_2$ | h1 | |
| B-2-3-2 | H | H | H | H | $CH_2$ | h2 | |
| B-2-3-3 | H | H | H | H | $CH_2$ | h3 | |
| B-2-3-4 | H | H | H | H | $CH_2$ | h4 | |
| B-2-3-5 | H | H | H | H | $CH_2$ | h5 | |
| B-2-3-6 | H | H | H | H | $CH_2$ | h6 | |
| B-2-3-7 | H | H | H | H | $CH_2$ | h7 | |
| B-2-3-8 | H | H | H | H | $CH_2$ | h8 | |
| B-2-3-9 | H | H | H | H | $CH_2CH_2$ | h1 | |
| B-2-3-10 | H | H | H | H | $CH_2CH_2$ | h2 | |
| B-2-3-11 | H | H | H | H | $CH_2CH_2$ | h3 | |
| B-2-3-12 | H | H | H | H | $CH_2CH_2$ | h4 | |
| B-2-3-13 | H | H | H | H | $CH_2CH_2$ | h5 | |
| B-2-3-14 | H | H | H | H | $CH_2CH_2$ | h6 | |
| B-2-3-15 | H | H | H | H | $CH_2CH_2$ | h7 | |
| B-2-3-16 | H | H | H | H | $CH_2CH_2$ | h8 | |
| B-2-3-17 | H | H | H | H | $CH_2CH_2CH_2$ | h1 | |
| B-2-3-18 | H | H | H | H | $CH_2CH_2CH_2$ | h2 | |
| B-2-3-19 | H | H | H | H | $CH_2CH_2CH_2$ | h3 | |
| B-2-3-20 | H | H | H | H | $CH_2CH_2CH_2$ | h4 | |
| B-2-3-21 | H | H | H | H | $CH_2CH_2CH_2$ | h5 | |
| B-2-3-22 | H | H | H | H | $CH_2CH_2CH_2$ | h6 | |
| B-2-3-23 | H | H | H | H | $CH_2CH_2CH_2$ | h7 | |
| B-2-3-24 | H | H | H | H | $CH_2CH_2CH_2$ | h8 | |
| B-2-3-25 | H | H | H | H | $CH_2CH_2CH_2CH_2CH_2CH_2$ | h1 | |
| B-2-3-26 | H | H | H | H | $CH_2CH_2CH_2CH_2CH_2CH_2$ | h2 | |
| B-2-3-27 | H | H | H | H | $CH_2CH_2CH_2CH_2CH_2CH_2$ | h3 | |
| B-2-3-28 | H | H | H | H | $CH_2CH_2CH_2CH_2CH_2CH_2$ | h4 | |
| B-2-3-29 | H | H | H | H | $CH_2CH_2CH_2CH_2CH_2CH_2$ | h5 | |
| B-2-3-30 | H | H | H | H | $CH_2CH_2CH_2CH_2CH_2CH_2$ | h6 | |
| B-2-3-31 | H | H | H | H | $CH_2CH_2CH_2CH_2CH_2CH_2$ | h7 | |

TABLE 13-continued

| Compound No. | R9 | R6 | R1a | R1b | D | Z | Physical Constant [ ] m.p. ° C. nD refractive index |
|---|---|---|---|---|---|---|---|
| B-2-3-32 | H | H | H | H | CH2CH2CH2CH2CH2CH2 | h8 | |
| B-2-3-33 | CH3 | H | H | H | CH2 | h1 | |
| B-2-3-34 | CH3 | H | H | H | CH2 | h2 | |
| B-2-3-35 | CH3 | H | H | H | CH2 | h3 | |
| B-2-3-36 | CH3 | H | H | H | CH2 | h4 | |
| B-2-3-37 | CH3 | H | H | H | CH2 | h5 | |
| B-2-3-38 | CH3 | H | H | H | CH2 | h6 | |
| B-2-3-39 | CH3 | H | H | H | CH2 | h7 | |
| B-2-3-40 | CH3 | H | H | H | CH2 | h8 | |
| B-2-3-41 | CH2CH3 | H | H | H | CH2 | h1 | |
| B-2-3-42 | CH2CH3 | H | H | H | CH2 | h2 | |
| B-2-3-43 | CH2CH3 | H | H | H | CH2 | h3 | |
| B-2-3-44 | CH2CH3 | H | H | H | CH2 | h4 | |
| B-2-3-45 | CH2CH3 | H | H | H | CH2 | h5 | |
| B-2-3-46 | CH2CH3 | H | H | H | CH2 | h6 | |
| B-2-3-47 | CH2CH3 | H | H | H | CH2 | h7 | |
| B-2-3-48 | CH2CH3 | H | H | H | CH2 | h8 | |
| B-2-3-49 | CH2CH2CH3 | H | H | H | CH2 | h1 | |
| B-2-3-50 | CH2CH2CH3 | H | H | H | CH2 | h2 | |
| B-2-3-51 | CH2CH2CH3 | H | H | H | CH2 | h3 | |
| B-2-3-52 | CH2CH2CH3 | H | H | H | CH2 | h4 | |
| B-2-3-53 | CH2CH2CH3 | H | H | H | CH2 | h5 | |
| B-2-3-54 | CH2CH2CH3 | H | H | H | CH2 | h6 | |
| B-2-3-55 | CH2CH2CH3 | H | H | H | CH2 | h7 | |
| B-2-3-56 | CH2CH2CH3 | H | H | H | CH2 | h8 | |
| B-2-3-57 | CH(CH3)2 | H | H | H | CH2 | h1 | |
| B-2-3-58 | CH(CH3)2 | H | H | H | CH2 | h2 | |
| B-2-3-59 | CH(CH3)2 | H | H | H | CH2 | h3 | |
| B-2-3-60 | CH(CH3)2 | H | H | H | CH2 | h4 | |
| B-2-3-61 | CH(CH3)2 | H | H | H | CH2 | h5 | |
| B-2-3-62 | CH(CH3)2 | H | H | H | CH2 | h6 | |
| B-2-3-63 | CH(CH3)2 | H | H | H | CH2 | h7 | |
| B-2-3-64 | CH(CH3)2 | H | H | H | CH2 | h8 | |
| B-2-3-65 | CH2C6H5 | H | H | H | CH2 | h1 | |
| B-2-3-66 | CH2C6H5 | H | H | H | CH2 | h2 | |
| B-2-3-67 | CH2C6H5 | H | H | H | CH2 | h3 | |
| B-2-3-68 | CH2C6H5 | H | H | H | CH2 | h4 | |
| B-2-3-69 | CH2C6H5 | H | H | H | CH2 | h5 | |
| B-2-3-70 | CH2C6H5 | H | H | H | CH2 | h6 | |
| B-2-3-71 | CH2C6H5 | H | H | H | CH2 | h7 | |
| B-2-3-72 | CH2C6H5 | H | H | H | CH2 | h8 | |
| B-2-3-73 | H | CH3 | H | H | CH2 | h1 | |
| B-2-3-74 | H | CH3 | H | H | CH2 | h2 | |
| B-2-3-75 | H | CH3 | H | H | CH2 | h3 | |
| B-2-3-76 | H | CH3 | H | H | CH2 | h4 | |
| B-2-3-77 | H | CH3 | H | H | CH2 | h5 | |
| B-2-3-78 | H | CH3 | H | H | CH2 | h6 | |
| B-2-3-79 | H | CH3 | H | H | CH2 | h7 | |
| B-2-3-80 | H | CH3 | H | H | CH2 | h8 | |
| B-2-3-81 | H | H | CH3 | H | CH2 | h1 | |
| B-2-3-82 | H | H | CH3 | H | CH2 | h2 | |
| B-2-3-83 | H | H | CH3 | H | CH2 | h3 | |
| B-2-3-84 | H | H | CH3 | H | CH2 | h4 | |
| B-2-3-85 | H | H | CH3 | H | CH2 | h5 | |
| B-2-3-86 | H | H | CH3 | H | CH2 | h6 | |
| B-2-3-87 | H | H | CH3 | H | CH2 | h7 | |
| B-2-3-88 | H | H | CH3 | H | CH2 | h8 | |
| B-2-3-89 | H | H | Cl | H | CH2 | h1 | |
| B-2-3-90 | H | H | Cl | H | CH2 | h2 | |
| B-2-3-91 | H | H | Cl | H | CH2 | h3 | |
| B-2-3-92 | H | H | Cl | H | CH2 | h4 | |
| B-2-3-93 | H | H | Cl | H | CH2 | h5 | |
| B-2-3-94 | H | H | Cl | H | CH2 | h6 | |
| B-2-3-95 | H | H | Cl | H | CH2 | h7 | |
| B-2-3-96 | H | H | Cl | H | CH2 | h8 | |
| B-2-3-97 | H | H | F | H | CH2 | h1 | |
| B-2-3-98 | H | H | F | H | CH2 | h2 | |

TABLE 13-continued

| Compound No. | R9 | R6 | R1a | R1b | D | Z | Physical Constant [ ] m.p. ° C. nD refractive index |
|---|---|---|---|---|---|---|---|
| B-2-3-99 | H | H | F | H | CH2 | h3 | |
| B-2-3-100 | H | H | F | H | CH2 | h4 | |
| B-2-3-101 | H | H | F | H | CH2 | h5 | |
| B-2-3-102 | H | H | F | H | CH2 | h6 | |
| B-2-3-103 | H | H | F | H | CH2 | h7 | |
| B-2-3-104 | H | H | F | H | CH2 | h8 | |
| B-2-3-105 | H | H | H | CH3 | CH2 | h1 | |
| B-2-3-106 | H | H | H | CH3 | CH2 | h2 | |
| B-2-3-107 | H | H | H | CH3 | CH2 | h3 | |
| B-2-3-108 | H | H | H | CH3 | CH2 | h4 | |
| B-2-3-109 | H | H | H | CH3 | CH2 | h5 | |
| B-2-3-110 | H | H | H | CH3 | CH2 | h6 | |
| B-2-3-111 | H | H | H | CH3 | CH2 | h7 | |
| B-2-3-112 | H | H | H | CH3 | CH2 | h8 | |
| B-2-3-113 | H | H | H | Cl | CH2 | h1 | |
| B-2-3-114 | H | H | H | Cl | CH2 | h2 | |
| B-2-3-115 | H | H | H | Cl | CH2 | h3 | |
| B-2-3-116 | H | H | H | Cl | CH2 | h4 | |
| B-2-3-117 | H | H | H | Cl | CH2 | h5 | |
| B-2-3-118 | H | H | H | Cl | CH2 | h6 | |
| B-2-3-119 | H | H | H | Cl | CH2 | h7 | |
| B-2-3-120 | H | H | H | Cl | CH2 | h8 | |
| B-2-3-121 | H | H | H | F | CH2 | h1 | |
| B-2-3-122 | H | H | H | F | CH2 | h2 | |
| B-2-3-123 | H | H | H | F | CH2 | h3 | |
| B-2-3-124 | H | H | H | F | CH2 | h4 | |
| B-2-3-125 | H | H | H | F | CH2 | h5 | |
| B-2-3-126 | H | H | H | F | CH2 | h6 | |
| B-2-3-127 | H | H | H | F | CH2 | h7 | |
| B-2-3-128 | H | H | H | F | CH2 | h8 | |

TABLE 14

| Compound No. | R9 | R6a | R6b | R1a | R1b | D | Z | Physical Constant [ ] m.p. ° C. nD refractive index |
|---|---|---|---|---|---|---|---|---|
| B-2-4-1 | H | H | H | H | H | CH2 | h1 | [98-102] |
| B-2-4-2 | H | H | H | H | H | CH2 | h2 | |
| B-2-4-3 | H | H | H | H | H | CH2 | h3 | |
| B-2-4-4 | H | H | H | H | H | CH2 | h4 | |
| B-2-4-5 | H | H | H | H | H | CH2 | h5 | |
| B-2-4-6 | H | H | H | H | H | CH2 | h6 | |
| B-2-4-7 | H | H | H | H | H | CH2 | h7 | |
| B-2-4-8 | H | H | H | H | H | CH2 | h8 | |
| B-2-4-9 | H | H | H | H | H | CH2CH2 | h1 | |
| B-2-4-10 | H | H | H | H | H | CH2CH2 | h2 | |
| B-2-4-11 | H | H | H | H | H | CH2CH2 | h3 | |
| B-2-4-12 | H | H | H | H | H | CH2CH2 | h4 | |
| B-2-4-13 | H | H | H | H | H | CH2CH2 | h5 | |
| B-2-4-14 | H | H | H | H | H | CH2CH2 | h6 | |
| B-2-4-15 | H | H | H | H | H | CH2CH2 | h7 | |
| B-2-4-16 | H | H | H | H | H | CH2CH2 | h8 | |
| B-2-4-17 | H | H | H | H | H | CH2CH2CH2 | h1 | |
| B-2-4-18 | H | H | H | H | H | CH2CH2CH2 | h2 | |

TABLE 14-continued

[Structure shown with R6a, R6b on imidazole; R1a, R1b on phenyl; N-D-Z with R9 substituent]

| Compound No. | R9 | R6a | R6b | R1a | R1b | D | Z | Physical Constant [ ] m.p. °C. $n_D$ refractive index |
|---|---|---|---|---|---|---|---|---|
| B-2-4-19 | H | H | H | H | H | $CH_2CH_2CH_2$ | h3 | |
| B-2-4-20 | H | H | H | H | H | $CH_2CH_2CH_2$ | h4 | |
| B-2-4-21 | H | H | H | H | H | $CH_2CH_2CH_2$ | h5 | |
| B-2-4-22 | H | H | H | H | H | $CH_2CH_2CH_2$ | h6 | |
| B-2-4-23 | H | H | H | H | H | $CH_2CH_2CH_2$ | h7 | |
| B-2-4-24 | H | H | H | H | H | $CH_2CH_2CH_2$ | h8 | |
| B-2-4-25 | H | H | H | H | H | $CH_2CH_2CH_2CH_2CH_2CH_2$ | h1 | |
| B-2-4-26 | H | H | H | H | H | $CH_2CH_2CH_2CH_2CH_2CH_2$ | h2 | |
| B-2-4-27 | H | H | H | H | H | $CH_2CH_2CH_2CH_2CH_2CH_2$ | h3 | |
| B-2-4-28 | H | H | H | H | H | $CH_2CH_2CH_2CH_2CH_2CH_2$ | h4 | |
| B-2-4-29 | H | H | H | H | H | $CH_2CH_2CH_2CH_2CH_2CH_2$ | h5 | |
| B-2-4-30 | H | H | H | H | H | $CH_2CH_2CH_2CH_2CH_2CH_2$ | h6 | |
| B-2-4-31 | H | H | H | H | H | $CH_2CH_2CH_2CH_2CH_2CH_2$ | h7 | |
| B-2-4-32 | H | H | H | H | H | $CH_2CH_2CH_2CH_2CH_2CH_2$ | h8 | |
| B-2-4-33 | $CH_3$ | H | H | H | H | $CH_2$ | h1 | |
| B-2-4-34 | $CH_3$ | H | H | H | H | $CH_2$ | h2 | |
| B-2-4-35 | $CH_3$ | H | H | H | H | $CH_2$ | h3 | |
| B-2-4-36 | $CH_3$ | H | H | H | H | $CH_2$ | h4 | |
| B-2-4-37 | $CH_3$ | H | H | H | H | $CH_2$ | h5 | |
| B-2-4-38 | $CH_3$ | H | H | H | H | $CH_2$ | h6 | |
| B-2-4-39 | $CH_3$ | H | H | H | H | $CH_2$ | h7 | |
| B-2-4-40 | $CH_3$ | H | H | H | H | $CH_2$ | h8 | |
| B-2-4-41 | $CH_2CH_3$ | H | H | H | H | $CH_2$ | h1 | |
| B-2-4-42 | $CH_2CH_3$ | H | H | H | H | $CH_2$ | h2 | |
| B-2-4-43 | $CH_2CH_3$ | H | H | H | H | $CH_2$ | h3 | |
| B-2-4-44 | $CH_2CH_3$ | H | H | H | H | $CH_2$ | h4 | |
| B-2-4-45 | $CH_2CH_3$ | H | H | H | H | $CH_2$ | h5 | |
| B-2-4-46 | $CH_2CH_3$ | H | H | H | H | $CH_2$ | h6 | |
| B-2-4-47 | $CH_2CH_3$ | H | H | H | H | $CH_2$ | h7 | |
| B-2-4-48 | $CH_2CH_3$ | H | H | H | H | $CH_2$ | h8 | |
| B-2-4-49 | $CH_2CH_2CH_3$ | H | H | H | H | $CH_2$ | h1 | |
| B-2-4-50 | $CH_2CH_2CH_3$ | H | H | H | H | $CH_2$ | h2 | |
| B-2-4-51 | $CH_2CH_2CH_3$ | H | H | H | H | $CH_2$ | h3 | |
| B-2-4-52 | $CH_2CH_2CH_3$ | H | H | H | H | $CH_2$ | h4 | |
| B-2-4-53 | $CH_2CH_2CH_3$ | H | H | H | H | $CH_2$ | h5 | |
| B-2-4-54 | $CH_2CH_2CH_3$ | H | H | H | H | $CH_2$ | h6 | |
| B-2-4-55 | $CH_2CH_2CH_3$ | H | H | H | H | $CH_2$ | h7 | |
| B-2-4-56 | $CH_2CH_2CH_3$ | H | H | H | H | $CH_2$ | h8 | |
| B-2-4-57 | $CH(CH_3)_2$ | H | H | H | H | $CH_2$ | h1 | |
| B-2-4-58 | $CH(CH_3)_2$ | H | H | H | H | $CH_2$ | h2 | |
| B-2-4-59 | $CH(CH_3)_2$ | H | H | H | H | $CH_2$ | h3 | |
| B-2-4-60 | $CH(CH_3)_2$ | H | H | H | H | $CH_2$ | h4 | |
| B-2-4-61 | $CH(CH_3)_2$ | H | H | H | H | $CH_2$ | h5 | |
| B-2-4-62 | $CH(CH_3)_2$ | H | H | H | H | $CH_2$ | h6 | |
| B-2-4-63 | $CH(CH_3)_2$ | H | H | H | H | $CH_2$ | h7 | |
| B-2-4-64 | $CH(CH_3)_2$ | H | H | H | H | $CH_2$ | h8 | |
| B-2-4-65 | $CH_2C_6H_5$ | H | H | H | H | $CH_2$ | h1 | |
| B-2-4-66 | $CH_2C_6H_5$ | H | H | H | H | $CH_2$ | h2 | |
| B-2-4-67 | $CH_2C_6H_5$ | H | H | H | H | $CH_2$ | h3 | |
| B-2-4-68 | $CH_2C_6H_5$ | H | H | H | H | $CH_2$ | h4 | |
| B-2-4-69 | $CH_2C_6H_5$ | H | H | H | H | $CH_2$ | h5 | |
| B-2-4-70 | $CH_2C_6H_5$ | H | H | H | H | $CH_2$ | h6 | |
| B-2-4-71 | $CH_2C_6H_5$ | H | H | H | H | $CH_2$ | h7 | |
| B-2-4-72 | $CH_2C_6H_5$ | H | H | H | H | $CH_2$ | h8 | |
| B-2-4-73 | H | $CH_3$ | H | H | H | $CH_2$ | h1 | [80-85] |
| B-2-4-74 | H | $CH_3$ | H | H | H | $CH_2$ | h2 | |
| B-2-4-75 | H | $CH_3$ | H | H | H | $CH_2$ | h3 | |
| B-2-4-76 | H | $CH_3$ | H | H | H | $CH_2$ | h4 | |
| B-2-4-77 | H | $CH_3$ | H | H | H | $CH_2$ | h5 | |
| B-2-4-78 | H | $CH_3$ | H | H | H | $CH_2$ | h6 | |
| B-2-4-79 | H | $CH_3$ | H | H | H | $CH_2$ | h7 | |
| B-2-4-80 | H | $CH_3$ | H | H | H | $CH_2$ | h8 | |
| B-2-4-81 | H | H | $CH_3$ | H | H | $CH_2$ | h1 | [>300] |
| B-2-4-82 | H | H | $CH_3$ | H | H | $CH_2$ | h2 | |
| B-2-4-83 | H | H | $CH_3$ | H | H | $CH_2$ | h3 | |

TABLE 14-continued

| Compound No. | R₉ | R₆ₐ | R₆ᵦ | R₁ₐ | R₁ᵦ | D | Z | Physical Constant [ ] m.p. °C. n_D refractive index |
|---|---|---|---|---|---|---|---|---|
| B-2-4-84 | H | H | CH₃ | H | H | CH₂ | h4 | |
| B-2-4-85 | H | H | CH₃ | H | H | CH₂ | h5 | |
| B-2-4-86 | H | H | CH₃ | H | H | CH₂ | h6 | |
| B-2-4-87 | H | H | CH₃ | H | H | CH₂ | h7 | |
| B-2-4-88 | H | H | CH₃ | H | H | CH₂ | h8 | |
| B-2-4-89 | H | H | H | CH₃ | H | CH₂ | h1 | |
| B-2-4-90 | H | H | H | CH₃ | H | CH₂ | h2 | |
| B-2-4-91 | H | H | H | CH₃ | H | CH₂ | h3 | |
| B-2-4-92 | H | H | H | CH₃ | H | CH₂ | h4 | |
| B-2-4-93 | H | H | H | CH₃ | H | CH₂ | h5 | |
| B-2-4-94 | H | H | H | CH₃ | H | CH₂ | h6 | |
| B-2-4-95 | H | H | H | CH₃ | H | CH₂ | h7 | |
| B-2-4-96 | H | H | H | CH₃ | H | CH₂ | h8 | |
| B-2-4-97 | H | H | H | Cl | H | CH₂ | h1 | |
| B-2-4-98 | H | H | H | Cl | H | CH₂ | h2 | |
| B-2-4-99 | H | H | H | Cl | H | CH₂ | h3 | |
| B-2-4-100 | H | H | H | Cl | H | CH₂ | h4 | |
| B-2-4-101 | H | H | H | Cl | H | CH₂ | h5 | |
| B-2-4-102 | H | H | H | Cl | H | CH₂ | h6 | |
| B-2-4-103 | H | H | H | Cl | H | CH₂ | h7 | |
| B-2-4-104 | H | H | H | Cl | H | CH₂ | h8 | |
| B-2-4-105 | H | H | H | F | H | CH₂ | h1 | |
| B-2-4-106 | H | H | H | F | H | CH₂ | h2 | |
| B-2-4-107 | H | H | H | F | H | CH₂ | h3 | |
| B-2-4-108 | H | H | H | F | H | CH₂ | h4 | |
| B-2-4-109 | H | H | H | F | H | CH₂ | h5 | |
| B-2-4-110 | H | H | H | F | H | CH₂ | h6 | |
| B-2-4-111 | H | H | H | F | H | CH₂ | h7 | |
| B-2-4-112 | H | H | H | F | H | CH₂ | h8 | |
| B-2-4-113 | H | H | H | H | CH₃ | CH₂ | h1 | |
| B-2-4-114 | H | H | H | H | CH₃ | CH₂ | h2 | |
| B-2-4-115 | H | H | H | H | CH₃ | CH₂ | h3 | |
| B-2-4-116 | H | H | H | H | CH₃ | CH₂ | h4 | |
| B-2-4-117 | H | H | H | H | CH₃ | CH₂ | h5 | |
| B-2-4-118 | H | H | H | H | CH₃ | CH₂ | h6 | |
| B-2-4-119 | H | H | H | H | CH₃ | CH₂ | h7 | |
| B-2-4-120 | H | H | H | H | CH₃ | CH₂ | h8 | |
| B-2-4-121 | H | H | H | H | Cl | CH₂ | h1 | |
| B-2-4-122 | H | H | H | H | Cl | CH₂ | h2 | |
| B-2-4-123 | H | H | H | H | Cl | CH₂ | h3 | |
| B-2-4-124 | H | H | H | H | Cl | CH₂ | h4 | |
| B-2-4-125 | H | H | H | H | Cl | CH₂ | h5 | |
| B-2-4-126 | H | H | H | H | Cl | CH₂ | h6 | |
| B-2-4-127 | H | H | H | H | Cl | CH₂ | h7 | |
| B-2-4-128 | H | H | H | H | Cl | CH₂ | h8 | |
| B-2-4-129 | H | H | H | H | F | CH₂ | h1 | |
| B-2-4-130 | H | H | H | H | F | CH₂ | h2 | |
| B-2-4-131 | H | H | H | H | F | CH₂ | h3 | |
| B-2-4-132 | H | H | H | H | F | CH₂ | h4 | |
| B-2-4-133 | H | H | H | H | F | CH₂ | h5 | |
| B-2-4-134 | H | H | H | H | F | CH₂ | h6 | |
| B-2-4-135 | H | H | H | H | F | CH₂ | h7 | |
| B-2-4-136 | H | H | H | H | F | CH₂ | h8 | |

TABLE 15

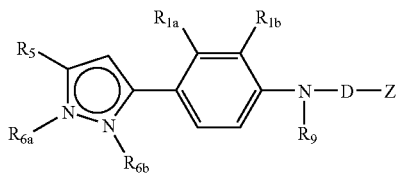

| Compound No. | R$_9$ | R$_5$ | R$_{6a}$ | R$_{6b}$ | R$_{1a}$ | R$_{1b}$ | D | Z | Physical Constant [ ] m.p. ° C. n$_D$ refractive index |
|---|---|---|---|---|---|---|---|---|---|
| B-2-5-1 | H | H | H | H | H | H | CH$_2$ | h1 | [103-108] |
| B-2-5-2 | H | H | H | H | H | H | CH$_2$ | h1 | [176-180] |
| B-2-5-3 | H | H | H | H | H | H | CH$_2$ | h2 | 2HCl salt |
| B-2-5-4 | H | H | H | H | H | H | CH$_2$ | h3 | [80-82] |
| B-2-5-5 | H | H | H | H | H | H | CH$_2$ | h4 | [132-135] |
| B-2-5-6 | H | H | H | H | H | H | CH$_2$ | h5 | |
| B-2-5-7 | H | H | H | H | H | H | CH$_2$ | h6 | [110-115] |
| B-2-5-8 | H | H | H | H | H | H | CH$_2$ | h7 | & NMR |
| B-2-5-9 | H | H | H | H | H | H | CH$_2$ | h8 | |
| B-2-5-10 | H | H | H | H | H | H | CH$_2$CH$_2$ | h1 | |
| B-2-5-11 | H | H | H | H | H | H | CH$_2$CH$_2$ | h2 | |
| B-2-5-12 | H | H | H | H | H | H | CH$_2$CH$_2$ | h3 | |
| B-2-5-13 | H | H | H | H | H | H | CH$_2$CH$_2$ | h4 | |
| B-2-5-14 | H | H | H | H | H | H | CH$_2$CH$_2$ | h5 | |
| B-2-5-15 | H | H | H | H | H | H | CH$_2$CH$_2$ | h6 | |
| B-2-5-16 | H | H | H | H | H | H | CH$_2$CH$_2$ | h7 | |
| B-2-5-17 | H | H | H | H | H | H | CH$_2$CH$_2$ | h8 | |
| B-2-5-18 | H | H | H | H | H | H | CH$_2$CH$_2$CH$_2$ | h1 | |
| B-2-5-19 | H | H | H | H | H | H | CH$_2$CH$_2$CH$_2$ | h2 | n$_D^{20.4}$1.5758 |
| B-2-5-20 | H | H | H | H | H | H | CH$_2$CH$_2$CH$_2$ | h3 | |
| B-2-5-21 | H | H | H | H | H | H | CH$_2$CH$_2$CH$_2$ | h4 | |
| B-2-5-22 | H | H | H | H | H | H | CH$_2$CH$_2$CH$_2$ | h5 | |
| B-2-5-23 | H | H | H | H | H | H | CH$_2$CH$_2$CH$_2$ | h6 | |
| B-2-5-24 | H | H | H | H | H | H | CH$_2$CH$_2$CH$_2$ | h7 | |
| B-2-5-25 | H | H | H | H | H | H | CH$_2$CH$_2$CH$_2$ | h8 | |
| B-2-5-26 | H | H | H | H | H | H | CH$_2$CH$_2$CH$_2$CH$_2$CH$_2$CH$_2$ | h1 | |
| B-2-5-27 | H | H | H | H | H | H | CH$_2$CH$_2$CH$_2$CH$_2$CH$_2$CH$_2$ | h2 | |
| B-2-5-28 | H | H | H | H | H | H | CH$_2$CH$_2$CH$_2$CH$_2$CH$_2$CH$_2$ | h3 | |
| B-2-5-29 | H | H | H | H | H | H | CH$_2$CH$_2$CH$_2$CH$_2$CH$_2$CH$_2$ | h4 | |
| B-2-5-30 | H | H | H | H | H | H | CH$_2$CH$_2$CH$_2$CH$_2$CH$_2$CH$_2$ | h5 | |
| B-2-5-31 | H | H | H | H | H | H | CH$_2$CH$_2$CH$_2$CH$_2$CH$_2$CH$_2$ | h6 | |
| B-2-5-32 | H | H | H | H | H | H | CH$_2$CH$_2$CH$_2$CH$_2$CH$_2$CH$_2$ | h7 | |
| B-2-5-33 | H | H | H | H | H | H | CH$_2$CH$_2$CH$_2$CH$_2$CH$_2$CH$_2$ | h8 | |
| B-2-5-34 | CH$_3$ | H | H | H | H | H | CH$_2$ | h1 | [113-117] |
| B-2-5-35 | CH$_3$ | H | H | H | H | H | CH$_2$ | h2 | |
| B-2-5-36 | CH$_3$ | H | H | H | H | H | CH$_2$ | h3 | |
| B-2-5-37 | CH$_3$ | H | H | H | H | H | CH$_2$ | h4 | |
| B-2-5-38 | CH$_3$ | H | H | H | H | H | CH$_2$ | h5 | |
| B-2-5-39 | CH$_3$ | H | H | H | H | H | CH$_2$ | h6 | |
| B-2-5-40 | CH$_3$ | H | H | H | H | H | CH$_2$ | h7 | |
| B-2-5-41 | CH$_3$ | H | H | H | H | H | CH$_2$ | h8 | |
| B-2-5-42 | CH$_2$CH$_3$ | H | H | H | H | H | CH$_2$ | h1 | [95-99] |
| B-2-5-43 | CH$_2$CH$_3$ | H | H | H | H | H | CH$_2$ | h2 | |
| B-2-5-44 | CH$_2$CH$_3$ | H | H | H | H | H | CH$_2$ | h3 | |
| B-2-5-45 | CH$_2$CH$_3$ | H | H | H | H | H | CH$_2$ | h4 | |
| B-2-5-46 | CH$_2$CH$_3$ | H | H | H | H | H | CH$_2$ | h5 | |
| B-2-5-47 | CH$_2$CH$_3$ | H | H | H | H | H | CH$_2$ | h6 | |
| B-2-5-48 | CH$_2$CH$_3$ | H | H | H | H | H | CH$_2$ | h7 | |
| B-2-5-49 | CH$_2$CH$_3$ | H | H | H | H | H | CH$_2$ | h8 | |
| B-2-5-50 | CH$_2$CH$_2$CH$_3$ | H | H | H | H | H | CH$_2$ | h1 | |
| B-2-5-51 | CH$_2$CH$_2$CH$_3$ | H | H | H | H | H | CH$_2$ | h2 | |
| B-2-5-52 | CH$_2$CH$_2$CH$_3$ | H | H | H | H | H | CH$_2$ | h3 | |
| B-2-5-53 | CH$_2$CH$_2$CH$_3$ | H | H | H | H | H | CH$_2$ | h4 | |
| B-2-5-54 | CH$_2$CH$_2$CH$_3$ | H | H | H | H | H | CH$_2$ | h5 | |
| B-2-5-55 | CH$_2$CH$_2$CH$_3$ | H | H | H | H | H | CH$_2$ | h6 | |
| B-2-5-56 | CH$_2$CH$_2$CH$_3$ | H | H | H | H | H | CH$_2$ | h7 | |
| B-2-5-57 | CH$_2$CH$_2$CH$_3$ | H | H | H | H | H | CH$_2$ | h8 | |
| B-2-5-58 | CH(CH$_3$)$_2$ | H | H | H | H | H | CH$_2$ | h1 | [89-92] |
| B-2-5-59 | CH(CH$_3$)$_2$ | H | H | H | H | H | CH$_2$ | h2 | |
| B-2-5-60 | CH(CH$_3$)$_2$ | H | H | H | H | H | CH$_2$ | h3 | |
| B-2-5-61 | CH(CH$_3$)$_2$ | H | H | H | H | H | CH$_2$ | h4 | |
| B-2-5-62 | CH(CH$_3$)$_2$ | H | H | H | H | H | CH$_2$ | h5 | |
| B-2-5-63 | CH(CH$_3$)$_2$ | H | H | H | H | H | CH$_2$ | h6 | |
| B-2-5-64 | CH(CH$_3$)$_2$ | H | H | H | H | H | CH$_2$ | h7 | |
| B-2-5-65 | CH(CH$_3$)$_2$ | H | H | H | H | H | CH$_2$ | h8 | |

TABLE 15-continued

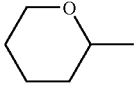

| Compound No. | $R_9$ | $R_5$ | $R_{6a}$ | $R_{6b}$ | $R_{1a}$ | $R_{1b}$ | D | Z | Physical Constant [ ] m.p. ° C. $n_D$ refractive index |
|---|---|---|---|---|---|---|---|---|---|
| B-2-5-66 | $CH_2C_6H_5$ | H | H | H | H | H | $CH_2$ | h1 | |
| B-2-5-67 | $CH_2C_6H_5$ | H | H | H | H | H | $CH_2$ | h2 | |
| B-2-5-68 | $CH_2C_6H_5$ | H | H | H | H | H | $CH_2$ | h3 | |
| B-2-5-69 | $CH_2C_6H_5$ | H | H | H | H | H | $CH_2$ | h4 | |
| B-2-5-70 | $CH_2C_6H_5$ | H | H | H | H | H | $CH_2$ | h5 | |
| B-2-5-71 | $CH_2C_6H_5$ | H | H | H | H | H | $CH_2$ | h6 | |
| B-2-5-72 | $CH_2C_6H_5$ | H | H | H | H | H | $CH_2$ | h7 | |
| B-2-5-73 | $CH_2C_6H_5$ | H | H | H | H | H | $CH_2$ | h8 | |
| B-2-5-74 | H | $CH_3$ | H | H | H | H | $CH_2$ | h1 | [115-119] |
| B-2-5-75 | H | $CH_3$ | H | H | H | H | $CH_2$ | h2 | |
| B-2-5-76 | H | $CH_3$ | H | H | H | H | $CH_2$ | h3 | |
| B-2-5-77 | H | $CH_3$ | H | H | H | H | $CH_2$ | h4 | |
| B-2-5-78 | H | $CH_3$ | H | H | H | H | $CH_2$ | h5 | |
| B-2-5-79 | H | $CH_3$ | H | H | H | H | $CH_2$ | h6 | |
| B-2-5-80 | H | $CH_3$ | H | H | H | H | $CH_2$ | h7 | |
| B-2-5-81 | H | $CH_3$ | H | H | H | H | $CH_2$ | h8 | |
| B-2-5-82 | H | H | $CH_3$ | H | H | H | $CH_2$ | h1 | [73-76] |
| B-2-5-83 | H | H | $CH_3$ | H | H | H | $CH_2$ | h2 | |
| B-2-5-84 | H | H | $CH_3$ | H | H | H | $CH_2$ | h3 | |
| B-2-5-85 | H | H | $CH_3$ | H | H | H | $CH_2$ | h4 | |
| B-2-5-86 | H | H | $CH_3$ | H | H | H | $CH_2$ | h5 | |
| B-2-5-87 | H | H | $CH_3$ | H | H | H | $CH_2$ | h6 | |
| B-2-5-88 | H | H | $CH_3$ | H | H | H | $CH_2$ | h7 | |
| B-2-5-89 | H | H | $CH_3$ | H | H | H | $CH_2$ | h8 | |
| B-2-5-90 | H | H | H | $CH_3$ | H | H | $CH_2$ | h1 | [49-54] |
| B-2-5-91 | H | H | H | $CH_3$ | H | H | $CH_2$ | h2 | |
| B-2-5-92 | H | H | H | $CH_3$ | H | H | $CH_2$ | h3 | |
| B-2-5-93 | H | H | H | $CH_3$ | H | H | $CH_2$ | h4 | |
| B-2-5-94 | H | H | H | $CH_3$ | H | H | $CH_2$ | h5 | |
| B-2-5-95 | H | H | H | $CH_3$ | H | H | $CH_2$ | h6 | |
| B-2-5-96 | H | H | H | $CH_3$ | H | H | $CH_2$ | h7 | |
| B-2-5-97 | H | H | H | $CH_3$ | H | H | $CH_2$ | h8 | |
| B-2-5-98 | H | H | tetrahydropyran-2-yl | — | H | H | $CH_2$ | h1 | [126-130] |
| B-2-5-99 | H | H | H | H | $CH_3$ | H | $CH_2$ | h1 | |
| B-2-5-100 | H | H | H | H | $CH_3$ | H | $CH_2$ | h2 | |
| B-2-5-101 | H | H | H | H | $CH_3$ | H | $CH_2$ | h3 | |
| B-2-5-102 | H | H | H | H | $CH_3$ | H | $CH_2$ | h4 | |
| B-2-5-103 | H | H | H | H | $CH_3$ | H | $CH_2$ | h5 | |
| B-2-5-104 | H | H | H | H | $CH_3$ | H | $CH_2$ | h6 | |
| B-2-5-105 | H | H | H | H | $CH_3$ | H | $CH_2$ | h7 | |
| B-2-5-106 | H | H | H | H | $CH_3$ | H | $CH_2$ | h8 | |
| B-2-5-107 | H | H | H | H | Cl | H | $CH_2$ | h1 | |
| B-2-5-108 | H | H | H | H | Cl | H | $CH_2$ | h2 | |
| B-2-5-109 | H | H | H | H | Cl | H | $CH_2$ | h3 | |
| B-2-5-110 | H | H | H | H | Cl | H | $CH_2$ | h4 | |
| B-2-5-111 | H | H | H | H | Cl | H | $CH_2$ | h5 | |
| B-2-5-112 | H | H | H | H | Cl | H | $CH_2$ | h6 | |
| B-2-5-113 | H | H | H | H | Cl | H | $CH_2$ | h7 | |
| B-2-5-114 | H | H | H | H | Cl | F | $CH_2$ | h8 | |
| B-2-5-115 | H | H | H | H | F | H | $CH_2$ | h1 | |
| B-2-5-116 | H | H | H | H | F | H | $CH_2$ | h2 | |
| B-2-5-117 | H | H | H | H | F | H | $CH_2$ | h3 | |
| B-2-5-118 | H | H | H | H | F | H | $CH_2$ | h4 | |
| B-2-5-119 | H | H | H | H | F | H | $CH_2$ | h5 | |
| B-2-5-120 | H | H | H | H | F | H | $CH_2$ | h6 | |
| B-2-5-121 | H | H | H | H | F | H | $CH_2$ | h7 | |
| B-2-5-122 | H | H | H | H | H | H | $CH_2$ | h8 | |
| B-2-5-123 | H | H | H | H | H | $CH_3$ | $CH_2$ | h1 | |
| B-2-5-124 | H | H | H | H | H | $CH_3$ | $CH_2$ | h2 | |
| B-2-5-125 | H | H | H | H | H | $CH_3$ | $CH_2$ | h3 | |

TABLE 15-continued

| Compound No. | $R_9$ | $R_5$ | $R_{6a}$ | $R_{6b}$ | $R_{1a}$ | $R_{1b}$ | D | Z | Physical Constant [ ] m.p. ° C. $n_D$ refractive index |
|---|---|---|---|---|---|---|---|---|---|
| B-2-5-126 | H | H | H | H | H | $CH_3$ | $CH_2$ | h4 | |
| B-2-5-127 | H | H | H | H | H | $CH_3$ | $CH_2$ | h5 | |
| B-2-5-128 | H | H | H | H | H | $CH_3$ | $CH_2$ | h6 | |
| B-2-5-129 | H | H | H | H | H | $CH_3$ | $CH_2$ | h7 | |
| B-2-5-130 | H | H | H | H | | $CH_3$ | $CH_2$ | h8 | |
| B-2-5-131 | H | H | H | H | H | Cl | $CH_2$ | h1 | |
| B-2-5-132 | H | H | H | H | H | Cl | $CH_2$ | h2 | |
| B-2-5-133 | H | H | H | H | H | Cl | $CH_2$ | h3 | |
| B-2-5-134 | H | H | H | H | H | Cl | $CH_2$ | h4 | |
| B-2-5-135 | H | H | H | H | H | Cl | $CH_2$ | h5 | |
| B-2-5-136 | H | H | H | H | H | Cl | $CH_2$ | h6 | |
| B-2-5-137 | H | H | H | H | H | Cl | $CH_2$ | h7 | |
| B-2-5-138 | H | H | H | H | H | Cl | $CH_2$ | h8 | |
| B-2-5-139 | H | H | H | H | H | F | $CH_2$ | h1 | |
| B-2-5-140 | H | H | H | H | H | F | $CH_2$ | h2 | |
| B-2-5-141 | H | H | H | H | H | F | $CH_2$ | h3 | |
| B-2-5-142 | H | H | H | H | H | F | $CH_2$ | h4 | |
| B-2-5-143 | H | H | H | H | H | F | $CH_2$ | h5 | |
| B-2-5-144 | H | H | H | H | H | F | $CH_2$ | h6 | |
| B-2-5-145 | H | H | H | H | H | F | $CH_2$ | h7 | |
| B-2-5-146 | H | H | H | H | H | F | $CH_2$ | h8 | |

TABLE 16

| Compound No. | $R_9$ | $R_5$ | $R_{6a}$ | $R_{6b}$ | D | Z | Physical Constant [ ] m.p. ° C. $n_D$ refractive index |
|---|---|---|---|---|---|---|---|
| B-2-6-1 | H | H | H | H | $CH_2$ | h1 | [96-99] |
| B-2-6-2 | H | H | H | H | $CH_2$ | h2 | [75-80] |
| B-2-6-3 | H | H | H | H | $CH_2$ | h3 | |
| B-2-6-4 | H | H | H | H | $CH_2$ | h4 | |
| B-2-6-5 | H | H | H | H | $CH_2$ | h5 | [188-190] |
| B-2-6-6 | H | H | H | H | $CH_2$ | h6 | [89-92] |
| B-2-6-7 | H | H | H | H | $CH_2$ | h7 | |
| B-2-6-8 | H | H | H | H | $CH_2$ | h8 | |
| B-2-6-9 | H | H | H | H | $CH_2CH_2$ | h1 | |
| B-2-6-10 | H | H | H | H | $CH_2CH_2$ | h2 | |
| B-2-6-11 | H | H | H | H | $CH_2CH_2$ | h3 | |
| B-2-6-12 | H | H | H | H | $CH_2CH_2$ | h4 | |
| B-2-6-13 | H | H | H | H | $CH_2CH_2$ | h5 | |
| B-2-6-14 | H | H | H | H | $CH_2CH_2$ | h6 | |
| B-2-6-15 | H | H | H | H | $CH_2CH_2$ | h7 | |
| B-2-6-16 | H | H | H | H | $CH_2CH_2$ | h8 | |
| B-2-6-17 | H | H | H | H | $CH_2CH_2CH_2$ | h1 | |
| B-2-6-18 | H | H | H | H | $CH_2CH_2CH_2$ | h2 | |
| B-2-6-19 | H | H | H | H | $CH_2CH_2CH_2$ | h3 | |
| B-2-6-20 | H | H | H | H | $CH_2CH_2CH_2$ | h4 | |
| B-2-6-21 | H | H | H | H | $CH_2CH_2CH_2$ | h5 | |
| B-2-6-22 | H | H | H | H | $CH_2CH_2CH_2$ | h6 | |
| B-2-6-23 | H | H | H | H | $CH_2CH_2CH_2$ | h7 | |
| B-2-6-24 | H | H | H | H | $CH_2CH_2CH_2$ | h8 | |

TABLE 16-continued

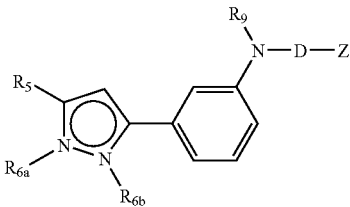

| Compound No. | $R_9$ | $R_5$ | $R_{6a}$ | $R_{6b}$ | D | Z | Physical Constant [ ] m.p. ° C. $n_D$ refractive index |
|---|---|---|---|---|---|---|---|
| B-2-6-25 | H | H | H | H | $CH_2CH_2CH_2CH_2CH_2CH_2$ | h1 | |
| B-2-6-26 | H | H | H | H | $CH_2CH_2CH_2CH_2CH_2CH_2$ | h2 | |
| B-2-6-27 | H | H | H | H | $CH_2CH_2CH_2CH_2CH_2CH_2$ | h3 | |
| B-2-6-28 | H | H | H | H | $CH_2CH_2CH_2CH_2CH_2CH_2$ | h4 | |
| B-2-6-29 | H | H | H | H | $CH_2CH_2CH_2CH_2CH_2CH_2$ | h5 | |
| B-2-6-30 | H | H | H | H | $CH_2CH_2CH_2CH_2CH_2CH_2$ | h6 | |
| B-2-6-31 | H | H | H | H | $CH_2CH_2CH_2CH_2CH_2CH_2$ | h7 | |
| B-2-6-32 | H | H | H | H | $CH_2CH_2CH_2CH_2CH_2CH_2$ | h8 | |
| B-2-6-33 | $CH_3$ | H | H | H | $CH_2$ | h1 | |
| B-2-6-34 | $CH_3$ | H | H | H | $CH_2$ | h2 | |
| B-2-6-35 | $CH_3$ | H | H | H | $CH_2$ | h3 | |
| B-2-6-36 | $CH_3$ | H | H | H | $CH_2$ | h4 | |
| B-2-6-37 | $CH_3$ | H | H | H | $CH_2$ | h5 | |
| B-2-6-38 | $CH_3$ | H | H | H | $CH_2$ | h6 | |
| B-2-6-39 | $CH_3$ | H | H | H | $CH_2$ | h7 | |
| B-2-6-40 | $CH_3$ | H | H | H | $CH_2$ | h8 | |
| B-2-6-41 | $CH_2CH_3$ | H | H | H | $CH_2$ | h1 | |
| B-2-6-42 | $CH_2CH_3$ | H | H | H | $CH_2$ | h2 | |
| B-2-6-43 | $CH_2CH_3$ | H | H | H | $CH_2$ | h3 | |
| B-2-6-44 | $CH_2CH_3$ | H | H | H | $CH_2$ | h4 | |
| B-2-6-45 | $CH_2CH_3$ | H | H | H | $CH_2$ | h5 | |
| B-2-6-46 | $CH_2CH_3$ | H | H | H | $CH_2$ | h6 | |
| B-2-6-47 | $CH_2CH_3$ | H | H | H | $CH_2$ | h7 | |
| B-2-6-48 | $CH_2CH_3$ | H | H | H | $CH_2$ | h8 | |
| B-2-6-49 | $CH_2CH_2CH_3$ | H | H | H | $CH_2$ | h1 | |
| B-2-6-50 | $CH_2CH_2CH_3$ | H | H | H | $CH_2$ | h2 | |
| B-2-6-51 | $CH_2CH_2CH_3$ | H | H | H | $CH_2$ | h3 | |
| B-2-6-52 | $CH_2CH_2CH_3$ | H | H | H | $CH_2$ | h4 | |
| B-2-6-53 | $CH_2CH_2CH_3$ | H | H | H | $CH_2$ | h5 | |
| B-2-6-54 | $CH_2CH_2CH_3$ | H | H | H | $CH_2$ | h6 | |
| B-2-6-55 | $CH_2CH_2CH_3$ | H | H | H | $CH_2$ | h7 | |
| B-2-6-56 | $CH_2CH_2CH_3$ | H | H | H | $CH_2$ | h8 | |
| B-2-6-57 | $CH(CH_3)_2$ | H | H | H | $CH_2$ | h1 | |
| B-2-6-58 | $CH(CH_3)_2$ | H | H | H | $CH_2$ | h2 | |
| B-2-6-59 | $CH(CH_3)_2$ | H | H | H | $CH_2$ | h3 | |
| B-2-6-60 | $CH(CH_3)_2$ | H | H | H | $CH_2$ | h4 | |
| B-2-6-61 | $CH(CH_3)_2$ | H | H | H | $CH_2$ | h5 | |
| B-2-6-62 | $CH(CH_3)_2$ | H | H | H | $CH_2$ | h6 | |
| B-2-6-63 | $CH(CH_3)_2$ | H | H | H | $CH_2$ | h7 | |
| B-2-6-64 | $CH(CH_3)_2$ | H | H | H | $CH_2$ | h8 | |
| B-2-6-65 | $CH_2C_6H_5$ | H | H | H | $CH_2$ | h1 | |
| B-2-6-66 | $CH_2C_6H_5$ | H | H | H | $CH_2$ | h2 | |
| B-2-6-67 | $CH_2C_6H_5$ | H | H | H | $CH_2$ | h3 | |
| B-2-6-68 | $CH_2C_6H_5$ | H | H | H | $CH_2$ | h4 | |
| B-2-6-69 | $CH_2C_6H_5$ | H | H | H | $CH_2$ | h5 | |
| B-2-6-70 | $CH_2C_6H_5$ | H | H | H | $CH_2$ | h6 | |
| B-2-6-71 | $CH_2C_6H_5$ | H | H | H | $CH_2$ | h7 | |
| B-2-6-72 | $CH_2C_6H_5$ | H | H | H | $CH_2$ | h8 | |
| B-2-6-73 | H | $CH_3$ | H | H | $CH_2$ | h1 | |
| B-2-6-74 | H | $CH_3$ | H | H | $CH_2$ | h2 | |
| B-2-6-75 | H | $CH_3$ | H | H | $CH_2$ | h3 | |
| B-2-6-76 | H | $CH_3$ | H | H | $CH_2$ | h4 | |
| B-2-6-77 | H | $CH_3$ | H | H | $CH_2$ | h5 | |
| B-2-6-78 | H | $CH_3$ | H | H | $CH_2$ | h6 | |
| B-2-6-79 | H | $CH_3$ | H | H | $CH_2$ | h7 | |
| B-2-6-80 | H | $CH_3$ | H | H | $CH_2$ | h8 | |
| B-2-6-81 | H | H | $CH_3$ | H | $CH_2$ | h1 | |
| B-2-6-82 | H | H | $CH_3$ | H | $CH_2$ | h2 | |
| B-2-6-83 | H | H | $CH_3$ | H | $CH_2$ | h3 | |
| B-2-6-84 | H | H | $CH_3$ | H | $CH_2$ | h4 | |
| B-2-6-85 | H | H | $CH_3$ | H | $CH_2$ | h5 | |
| B-2-6-86 | H | H | $CH_3$ | H | $CH_2$ | h6 | |
| B-2-6-87 | H | H | $CH_3$ | H | $CH_2$ | h7 | |
| B-2-6-88 | H | H | $CH_3$ | H | $CH_2$ | h8 | |

TABLE 16-continued

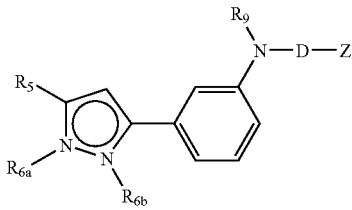

| Compound No. | $R_9$ | $R_5$ | $R_{6a}$ | $R_{6b}$ | D | Z | Physical Constant [ ] m.p. ° C. $n_D$ refractive index |
|---|---|---|---|---|---|---|---|
| B-2-6-89 | H | H | H | $CH_3$ | $CH_2$ | h1 | |
| B-2-6-90 | H | H | H | $CH_3$ | $CH_2$ | h2 | |
| B-2-6-91 | H | H | H | $CH_3$ | $CH_2$ | h3 | |
| B-2-6-92 | H | H | H | $CH_3$ | $CH_2$ | h4 | |
| B-2-6-93 | H | H | H | $CH_3$ | $CH_2$ | h5 | |
| B-2-6-94 | H | H | H | $CH_3$ | $CH_2$ | h6 | |
| B-2-6-95 | H | H | H | $CH_3$ | $CH_2$ | h7 | |
| B-2-6-96 | H | H | H | $CH_3$ | $CH_2$ | h8 | |

TABLE 17

| Compound No. | $R_9$ | $R_{1a}$ | $R_{1b}$ | D | Z | Physical Constant [ ] m.p. ° C. $n_D$ refractive index |
|---|---|---|---|---|---|---|
| B-2-7-1 | H | H | H | $CH_2$ | h1 | [57-62] |
| B-2-7-2 | H | H | H | $CH_2$ | h2 | |
| B-2-7-3 | H | H | H | $CH_2$ | h3 | |
| B-2-7-4 | H | H | H | $CH_2$ | h4 | |
| B-2-7-5 | H | H | H | $CH_2$ | h5 | |
| B-2-7-6 | H | H | H | $CH_2$ | h6 | |
| B-2-7-7 | H | H | H | $CH_2$ | h7 | |
| B-2-7-8 | H | H | H | $CH_2$ | h8 | |
| B-2-7-9 | H | H | H | $CH_2CH_2$ | h1 | |
| B-2-7-10 | H | H | H | $CH_2CH_2$ | h2 | |
| B-2-7-11 | H | H | H | $CH_2CH_2$ | h3 | |
| B-2-7-12 | H | H | H | $CH_2CH_2$ | h4 | |
| B-2-7-13 | H | H | H | $CH_2CH_2$ | h5 | |
| B-2-7-14 | H | H | H | $CH_2CH_2$ | h6 | |
| B-2-7-15 | H | H | H | $CH_2CH_2$ | h7 | |
| B-2-7-16 | H | H | H | $CH_2CH_2$ | h8 | |
| B-2-7-17 | H | H | H | $CH_2CH_2CH_2$ | h1 | |
| B-2-7-18 | H | H | H | $CH_2CH_2CH_2$ | h2 | |
| B-2-7-19 | H | H | H | $CH_2CH_2CH_2$ | h3 | |
| B-2-7-20 | H | H | H | $CH_2CH_2CH_2$ | h4 | |
| B-2-7-21 | H | H | H | $CH_2CH_2CH_2$ | h5 | |
| B-2-7-22 | H | H | H | $CH_2CH_2CH_2$ | h6 | |
| B-2-7-23 | H | H | H | $CH_2CH_2CH_2$ | h7 | |
| B-2-7-24 | H | H | H | $CH_2CH_2CH_2$ | h8 | |
| B-2-7-25 | H | H | H | $CH_2CH_2CH_2CH_2CH_2CH_2$ | h1 | |
| B-2-7-26 | H | H | H | $CH_2CH_2CH_2CH_2CH_2CH_2$ | h2 | |
| B-2-7-27 | H | H | H | $CH_2CH_2CH_2CH_2CH_2CH_2$ | h3 | |
| B-2-7-28 | H | H | H | $CH_2CH_2CH_2CH_2CH_2CH_2$ | h4 | |
| B-2-7-29 | H | H | H | $CH_2CH_2CH_2CH_2CH_2CH_2$ | h5 | |
| B-2-7-30 | H | H | H | $CH_2CH_2CH_2CH_2CH_2CH_2$ | h6 | |
| B-2-7-31 | H | H | H | $CH_2CH_2CH_2CH_2CH_2CH_2$ | h7 | |
| B-2-7-32 | H | H | H | $CH_2CH_2CH_2CH_2CH_2CH_2$ | h8 | |
| B-2-7-33 | $CH_3$ | H | H | $CH_2$ | h1 | |
| B-2-7-34 | $CH_3$ | H | H | $CH_2$ | h2 | |
| B-2-7-35 | $CH_3$ | H | H | $CH_2$ | h3 | |
| B-2-7-36 | $CH_3$ | H | H | $CH_2$ | h4 | |
| B-2-7-37 | $CH_3$ | H | H | $CH_2$ | h5 | |
| B-2-7-38 | $CH_3$ | H | H | $CH_2$ | h6 | |
| B-2-7-39 | $CH_3$ | H | H | $CH_2$ | h7 | |

TABLE 17-continued

| Compound No. | $R_9$ | $R_{1a}$ | $R_{1b}$ | D | Z | Physical Constant [ ] m.p. °C. $n_D$ refractive index |
|---|---|---|---|---|---|---|
| B-2-7-40 | CH$_3$ | H | H | CH$_2$ | h8 | |
| B-2-7-41 | CH$_2$CH$_3$ | H | H | CH$_2$ | h1 | |
| B-2-7-42 | CH$_2$CH$_3$ | H | H | CH$_2$ | h2 | |
| B-2-7-43 | CH$_2$CH$_3$ | H | H | CH$_2$ | h3 | |
| B-2-7-44 | CH$_2$CH$_3$ | H | H | CH$_2$ | h4 | |
| B-2-7-45 | CH$_2$CH$_3$ | H | H | CH$_2$ | h5 | |
| B-2-7-46 | CH$_2$CH$_3$ | H | H | CH$_2$ | h6 | |
| B-2-7-47 | CH$_2$CH$_3$ | H | H | CH$_2$ | h7 | |
| B-2-7-48 | CH$_2$CH$_3$ | H | H | CH$_2$ | h8 | |
| B-2-7-49 | CH$_2$CH$_2$CH$_3$ | H | H | CH$_2$ | h1 | |
| B-2-7-50 | CH$_2$CH$_2$CH$_3$ | H | H | CH$_2$ | h2 | |
| B-2-7-51 | CH$_2$CH$_2$CH$_3$ | H | H | CH$_2$ | h3 | |
| B-2-7-52 | CH$_2$CH$_2$CH$_3$ | H | H | CH$_2$ | h4 | |
| B-2-7-53 | CH$_2$CH$_2$CH$_3$ | H | H | CH$_2$ | h5 | |
| B-2-7-54 | CH$_2$CH$_2$CH$_3$ | H | H | CH$_2$ | h6 | |
| B-2-7-55 | CH$_2$CH$_2$CH$_3$ | H | H | CH$_2$ | h7 | |
| B-2-7-56 | CH$_2$CH$_2$CH$_3$ | H | H | CH$_2$ | h8 | |
| B-2-7-57 | CH(CH$_3$)$_2$ | H | H | CH$_2$ | h1 | |
| B-2-7-58 | CH(CH$_3$)$_2$ | H | H | CH$_2$ | h2 | |
| B-2-7-59 | CH(CH$_3$)$_2$ | H | H | CH$_2$ | h3 | |
| B-2-7-60 | CH(CH$_3$)$_2$ | H | H | CH$_2$ | h4 | |
| B-2-7-61 | CH(CH$_3$)$_2$ | H | H | CH$_2$ | h5 | |
| B-2-7-62 | CH(CH$_3$)$_2$ | H | H | CH$_2$ | h6 | |
| B-2-7-63 | CH(CH$_3$)$_2$ | H | H | CH$_2$ | h7 | |
| B-2-7-64 | CH(CH$_3$)$_2$ | H | H | CH$_2$ | h8 | |
| B-2-7-65 | CH$_2$C$_6$H$_5$ | H | H | CH$_2$ | h1 | |
| B-2-7-66 | CH$_2$C$_6$H$_5$ | H | H | CH$_2$ | h2 | |
| B-2-7-67 | CH$_2$C$_6$H$_5$ | H | H | CH$_2$ | h3 | |
| B-2-7-68 | CH$_2$C$_6$H$_5$ | H | H | CH$_2$ | h4 | |
| B-2-7-69 | CH$_2$C$_6$H$_5$ | H | H | CH$_2$ | h5 | |
| B-2-7-70 | CH$_2$C$_6$H$_5$ | H | H | CH$_2$ | h6 | |
| B-2-7-71 | CH$_2$C$_6$H$_5$ | H | H | CH$_2$ | h7 | |
| B-2-7-72 | CH$_2$C$_6$H$_5$ | H | H | CH$_2$ | h8 | |
| B-2-7-73 | H | CH$_3$ | H | CH$_2$ | h1 | |
| B-2-7-74 | H | CH$_3$ | H | CH$_2$ | h2 | |
| B-2-7-75 | H | CH$_3$ | H | CH$_2$ | h3 | |
| B-2-7-76 | H | CH$_3$ | H | CH$_2$ | h4 | |
| B-2-7-77 | H | CH$_3$ | H | CH$_2$ | h5 | |
| B-2-7-78 | H | CH$_3$ | H | CH$_2$ | h6 | |
| B-2-7-79 | H | CH$_3$ | H | CH$_2$ | h7 | |
| B-2-7-80 | H | CH$_3$ | H | CH$_2$ | h8 | |
| B-2-7-81 | H | Cl | H | CH$_2$ | h1 | |
| B-2-7-82 | H | Cl | H | CH$_2$ | h2 | |
| B-2-7-83 | H | Cl | H | CH$_2$ | h3 | |
| B-2-7-84 | H | Cl | H | CH$_2$ | h4 | |
| B-2-7-85 | H | Cl | H | CH$_2$ | h5 | |
| B-2-7-86 | H | Cl | H | CH$_2$ | h6 | |
| B-2-7-87 | H | Cl | H | CH$_2$ | h7 | |
| B-2-7-88 | H | Cl | H | CH$_2$ | h8 | |
| B-2-7-89 | H | F | H | CH$_2$ | h1 | |
| B-2-7-90 | H | F | H | CH$_2$ | h2 | |
| B-2-7-91 | H | F | H | CH$_2$ | h3 | |
| B-2-7-92 | H | F | H | CH$_2$ | h4 | |
| B-2-7-93 | H | F | H | CH$_2$ | h5 | |
| B-2-7-94 | H | F | H | CH$_2$ | h6 | |
| B-2-7-95 | H | F | H | CH$_2$ | h7 | |
| B-2-7-96 | H | F | H | CH$_2$ | h8 | |
| B-2-7-97 | H | H | CH$_3$ | CH$_2$ | h1 | |
| B-2-7-98 | H | H | CH$_3$ | CH$_2$ | h2 | |
| B-2-7-99 | H | H | CH$_3$ | CH$_2$ | h3 | |
| B-2-7-100 | H | H | CH$_3$ | CH$_2$ | h4 | |
| B-2-7-101 | H | H | CH$_3$ | CH$_2$ | h5 | |
| B-2-7-102 | H | H | CH$_3$ | CH$_2$ | h6 | |
| B-2-7-103 | H | H | CH$_3$ | CH$_2$ | h7 | |
| B-2-7-104 | H | H | CH$_3$ | CH$_2$ | h8 | |
| B-2-7-105 | H | H | Cl | CH$_2$ | h1 | |
| B-2-7-106 | H | H | Cl | CH$_2$ | h2 | |

TABLE 17-continued

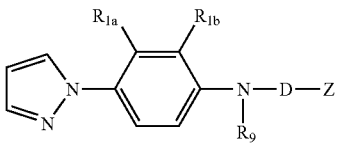

| Compound No. | $R_9$ | $R_{1a}$ | $R_{1b}$ | D | Z | Physical Constant [ ] m.p. ° C. $n_D$ refractive index |
|---|---|---|---|---|---|---|
| B-2-7-107 | H | H | Cl | $CH_2$ | h3 | |
| B-2-7-108 | H | H | Cl | $CH_2$ | h4 | |
| B-2-7-109 | H | H | Cl | $CH_2$ | h5 | |
| B-2-7-110 | H | H | Cl | $CH_2$ | h6 | |
| B-2-7-111 | H | H | Cl | $CH_2$ | h7 | |
| B-2-7-112 | H | H | Cl | $CH_2$ | h8 | |
| B-2-7-113 | H | H | F | $CH_2$ | h1 | |
| B-2-7-114 | H | H | F | $CH_2$ | h2 | |
| B-2-7-115 | H | H | F | $CH_2$ | h3 | |
| B-2-7-116 | H | H | F | $CH_2$ | h4 | |
| B-2-7-117 | H | H | F | $CH_2$ | h5 | |
| B-2-7-118 | H | H | F | $CH_2$ | h6 | |
| B-2-7-119 | H | H | F | $CH_2$ | h7 | |
| B-2-7-120 | H | H | F | $CH_2$ | h8 | |

TABLE 18

| Compound No. | $R_9$ | $R_6$ | $R_{1a}$ | $R_{1b}$ | D | Z | Physical Constant [ ] m.p. ° C. $n_D$ refractive index |
|---|---|---|---|---|---|---|---|
| B-2-8-1 | H | H | H | H | $CH_2$ | h1 | & NMR |
| B-2-8-2 | H | H | H | H | $CH_2$ | h2 | |
| B-2-8-3 | H | H | H | H | $CH_2$ | h3 | |
| B-2-8-4 | H | H | H | H | $CH_2$ | h4 | |
| B-2-8-5 | H | H | H | H | $CH_2$ | h5 | |
| B-2-8-6 | H | H | H | H | $CH_2$ | h6 | |
| B-2-8-7 | H | H | H | H | $CH_2$ | h7 | |
| B-2-8-8 | H | H | H | H | $CH_2$ | h8 | |
| B-2-8-9 | H | H | H | H | $CH_2CH_2$ | h1 | |
| B-2-8-10 | H | H | H | H | $CH_2CH_2$ | h2 | |
| B-2-8-11 | H | H | H | H | $CH_2CH_2$ | h3 | |
| B-2-8-12 | H | H | H | H | $CH_2CH_2$ | h4 | |
| B-2-8-13 | H | H | H | H | $CH_2CH_2$ | h5 | |
| B-2-8-14 | H | H | H | H | $CH_2CH_2$ | h6 | |
| B-2-8-15 | H | H | H | H | $CH_2CH_2$ | h7 | |
| B-2-8-16 | H | H | H | H | $CH_2CH_2$ | h8 | |
| B-2-8-17 | H | H | H | H | $CH_2CH_2CH_2$ | h1 | |
| B-2-8-18 | H | H | H | H | $CH_2CH_2CH_2$ | h2 | |
| B-2-8-19 | H | H | H | H | $CH_2CH_2CH_2$ | h3 | |
| B-2-8-20 | H | H | H | H | $CH_2CH_2CH_2$ | h4 | |
| B-2-8-21 | H | H | H | H | $CH_2CH_2CH_2$ | h5 | |
| B-2-8-22 | H | H | H | H | $CH_2CH_2CH_2$ | h6 | |
| B-2-8-23 | H | H | H | H | $CH_2CH_2CH_2$ | h7 | |
| B-2-8-24 | H | H | H | H | $CH_2CH_2CH_2$ | h8 | |
| B-2-8-25 | H | H | H | H | $CH_2CH_2CH_2CH_2CH_2CH_2$ | h1 | |
| B-2-8-26 | H | H | H | H | $CH_2CH_2CH_2CH_2CH_2CH_2$ | h2 | |
| B-2-8-27 | H | H | H | H | $CH_2CH_2CH_2CH_2CH_2CH_2$ | h3 | |
| B-2-8-28 | H | H | H | H | $CH_2CH_2CH_2CH_2CH_2CH_2$ | h4 | |
| B-2-8-29 | H | H | H | H | $CH_2CH_2CH_2CH_2CH_2CH_2$ | h5 | |
| B-2-8-30 | H | H | H | H | $CH_2CH_2CH_2CH_2CH_2CH_2$ | h6 | |
| B-2-8-31 | H | H | H | H | $CH_2CH_2CH_2CH_2CH_2CH_2$ | h7 | |
| B-2-8-32 | H | H | H | H | $CH_2CH_2CH_2CH_2CH_2CH_2$ | h8 | |
| B-2-8-33 | $CH_3$ | H | H | H | $CH_2$ | h1 | |
| B-2-8-34 | $CH_3$ | H | H | H | $CH_2$ | h2 | |
| B-2-8-35 | $CH_3$ | H | H | H | $CH_2$ | h3 | |
| B-2-8-36 | $CH_3$ | H | H | H | $CH_2$ | h4 | |

TABLE 18-continued

[Structure: pyrazole with R6 on N, connected to benzene ring with R1a, R1b substituents, and N(R9)-D-Z group]

| Compound No. | R$_9$ | R$_6$ | R$_{1a}$ | R$_{1b}$ | D | Z | Physical Constant [ ] m.p. °C. n$_D$ refractive index |
|---|---|---|---|---|---|---|---|
| B-2-8-37 | CH$_3$ | H | H | H | CH$_2$ | h5 | |
| B-2-8-38 | CH$_3$ | H | H | H | CH$_2$ | h6 | |
| B-2-8-39 | CH$_3$ | H | H | H | CH$_2$ | h7 | |
| B-2-8-40 | CH$_3$ | H | H | H | CH$_2$ | h8 | |
| B-2-8-41 | CH$_2$CH$_3$ | H | H | H | CH$_2$ | h1 | & NMR |
| B-2-8-42 | CH$_2$CH$_3$ | H | H | H | CH$_2$ | h2 | |
| B-2-8-43 | CH$_2$CH$_3$ | H | H | H | CH$_2$ | h3 | |
| B-2-8-44 | CH$_2$CH$_3$ | H | H | H | CH$_2$ | h4 | |
| B-2-8-45 | CH$_2$CH$_3$ | H | H | H | CH$_2$ | h5 | |
| B-2-8-46 | CH$_2$CH$_3$ | H | H | H | CH$_2$ | h6 | |
| B-2-8-47 | CH$_2$CH$_3$ | H | H | H | CH$_2$ | h7 | |
| B-2-8-48 | CH$_2$CH$_3$ | H | H | H | CH$_2$ | h8 | |
| B-2-8-49 | CH$_2$CH$_2$CH$_3$ | H | H | H | CH$_2$ | h1 | |
| B-2-8-50 | CH$_2$CH$_2$CH$_3$ | H | H | H | CH$_2$ | h2 | |
| B-2-8-51 | CH$_2$CH$_2$CH$_3$ | H | H | H | CH$_2$ | h3 | |
| B-2-8-52 | CH$_2$CH$_2$CH$_3$ | H | H | H | CH$_2$ | h4 | |
| B-2-8-53 | CH$_2$CH$_2$CH$_3$ | H | H | H | CH$_2$ | h5 | |
| B-2-8-54 | CH$_2$CH$_2$CH$_3$ | H | H | H | CH$_2$ | h6 | |
| B-2-8-55 | CH$_2$CH$_2$CH$_3$ | H | H | H | CH$_2$ | h7 | |
| B-2-8-56 | CH$_2$CH$_2$CH$_3$ | H | H | H | CH$_2$ | h8 | |
| B-2-8-57 | CH(CH$_3$)$_2$ | H | H | H | CH$_2$ | h1 | |
| B-2-8-58 | CH(CH$_3$)$_2$ | H | H | H | CH$_2$ | h2 | |
| B-2-8-59 | CH(CH$_3$)$_2$ | H | H | H | CH$_2$ | h3 | |
| B-2-8-60 | CH(CH$_3$)$_2$ | H | H | H | CH$_2$ | h4 | |
| B-2-8-61 | CH(CH$_3$)$_2$ | H | H | H | CH$_2$ | h5 | |
| B-2-8-62 | CH(CH$_3$)$_2$ | H | H | H | CH$_2$ | h6 | |
| B-2-8-63 | CH(CH$_3$)$_2$ | H | H | H | CH$_2$ | h7 | |
| B-2-8-64 | CH(CH$_3$)$_2$ | H | H | H | CH$_2$ | h8 | |
| B-2-8-65 | CH$_2$C$_6$H$_5$ | H | H | H | CH$_2$ | h1 | |
| B-2-8-66 | CH$_2$C$_6$H$_5$ | H | H | H | CH$_2$ | h2 | |
| B-2-8-67 | CH$_2$C$_6$H$_5$ | H | H | H | CH$_2$ | h3 | |
| B-2-8-68 | CH$_2$C$_6$H$_5$ | H | H | H | CH$_2$ | h4 | |
| B-2-8-69 | CH$_2$C$_6$H$_5$ | H | H | H | CH$_2$ | h5 | |
| B-2-8-70 | CH$_2$C$_6$H$_5$ | H | H | H | CH$_2$ | h6 | |
| B-2-8-71 | CH$_2$C$_6$H$_5$ | H | H | H | CH$_2$ | h7 | |
| B-2-8-72 | CH$_2$C$_6$H$_5$ | H | H | H | CH$_2$ | h8 | |
| B-2-8-73 | H | CH$_3$ | H | H | CH$_2$ | h1 | [157-159] |
| B-2-8-74 | H | CH$_3$ | H | H | CH$_2$ | h2 | |
| B-2-8-75 | H | CH$_3$ | H | H | CH$_2$ | h3 | |
| B-2-8-76 | H | CH$_3$ | H | H | CH$_2$ | h4 | |
| B-2-8-77 | H | CH$_3$ | H | H | CH$_2$ | h5 | |
| B-2-8-78 | H | CH$_3$ | H | H | CH$_2$ | h6 | |
| B-2-8-79 | H | CH$_3$ | H | H | CH$_2$ | h7 | |
| B-2-8-80 | H | CH$_3$ | H | H | CH$_2$ | h8 | |
| B-2-8-81 | H | H | CH$_3$ | H | CH$_2$ | h1 | |
| B-2-8-82 | H | H | CH$_3$ | H | CH$_2$ | h2 | |
| B-2-8-83 | H | H | CH$_3$ | H | CH$_2$ | h3 | |
| B-2-8-84 | H | H | CH$_3$ | H | CH$_2$ | h4 | |
| B-2-8-85 | H | H | CH$_3$ | H | CH$_2$ | h5 | |
| B-2-8-86 | H | H | CH$_3$ | H | CH$_2$ | h6 | |
| B-2-8-87 | H | H | CH$_3$ | H | CH$_2$ | h7 | |
| B-2-8-88 | H | H | CH$_3$ | H | CH$_2$ | h8 | |
| B-2-8-89 | H | H | Cl | H | CH$_2$ | h1 | |
| B-2-8-90 | H | H | Cl | H | CH$_2$ | h2 | |
| B-2-8-91 | H | H | Cl | H | CH$_2$ | h3 | |
| B-2-8-92 | H | H | Cl | H | CH$_2$ | h4 | |
| B-2-8-93 | H | H | Cl | H | CH$_2$ | h5 | |
| B-2-8-94 | H | H | Cl | H | CH$_2$ | h6 | |
| B-2-8-95 | H | H | Cl | H | CH$_2$ | h7 | |
| B-2-8-96 | H | H | Cl | H | CH$_2$ | h8 | |
| B-2-8-97 | H | H | F | H | CH$_2$ | h1 | |
| B-2-8-98 | H | H | F | H | CH$_2$ | h2 | |
| B-2-8-99 | H | H | F | H | CH$_2$ | h3 | |
| B-2-8-100 | H | H | F | H | CH$_2$ | h4 | |
| B-2-8-101 | H | H | F | H | CH$_2$ | h5 | |
| B-2-8-102 | H | H | F | H | CH$_2$ | h6 | |
| B-2-8-103 | H | H | F | H | CH$_2$ | h7 | |

TABLE 18-continued

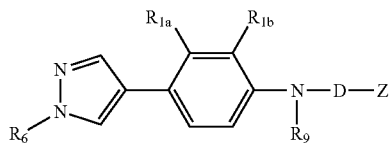

| Compound No. | $R_9$ | $R_6$ | $R_{1a}$ | $R_{1b}$ | D | Z | Physical Constant [ ] m.p. °C. $n_D$ refractive index |
|---|---|---|---|---|---|---|---|
| B-2-8-104 | H | H | F | H | CH$_2$ | h8 | |
| B-2-8-105 | H | H | H | CH$_3$ | CH$_2$ | h1 | |
| B-2-8-106 | H | H | H | CH$_3$ | CH$_2$ | h2 | |
| B-2-8-107 | H | H | H | CH$_3$ | CH$_2$ | h3 | |
| B-2-8-108 | H | H | H | CH$_3$ | CH$_2$ | h4 | |
| B-2-8-109 | H | H | H | CH$_3$ | CH$_2$ | h5 | |
| B-2-8-110 | H | H | H | CH$_3$ | CH$_2$ | h6 | |
| B-2-8-111 | H | H | H | CH$_3$ | CH$_2$ | h7 | |
| B-2-8-112 | H | H | H | CH$_3$ | CH$_2$ | h8 | |
| B-2-8-113 | H | H | H | Cl | CH$_2$ | h1 | |
| B-2-8-114 | H | H | H | Cl | CH$_2$ | h2 | |
| B-2-8-115 | H | H | H | Cl | CH$_2$ | h3 | |
| B-2-8-116 | H | H | H | Cl | CH$_2$ | h4 | |
| B-2-8-117 | H | H | H | Cl | CH$_2$ | h5 | |
| B-2-8-118 | H | H | H | Cl | CH$_2$ | h6 | |
| B-2-8-119 | H | H | H | Cl | CH$_2$ | h7 | |
| B-2-8-120 | H | H | H | Cl | CH$_2$ | h8 | |
| B-2-8-121 | H | H | H | F | CH$_2$ | h1 | |
| B-2-8-122 | H | H | H | F | CH$_2$ | h2 | |
| B-2-8-123 | H | H | H | F | CH$_2$ | h3 | |
| B-2-8-124 | H | H | H | F | CH$_2$ | h4 | |
| B-2-8-125 | H | H | H | F | CH$_2$ | h5 | |
| B-2-8-126 | H | H | H | F | CH$_2$ | h6 | |
| B-2-8-127 | H | H | H | F | CH$_2$ | h7 | |
| B-2-8-128 | H | H | H | F | CH$_2$ | h8 | |

TABLE 19

| Compound No. | D | Z | Physical Constant [ ] m.p. °C. $n_D$ refractive index |
|---|---|---|---|
| B-2-9-1 | CH$_2$ | h1 | [129-131] |
| B-2-9-2 | CH$_2$ | h2 | |
| B-2-9-3 | CH$_2$ | h3 | |
| B-2-9-4 | CH$_2$ | h4 | |
| B-2-9-5 | CH$_2$ | h5 | |
| B-2-9-6 | CH$_2$ | h6 | |
| B-2-9-7 | CH$_2$ | h7 | |
| B-2-9-8 | CH$_2$ | h8 | |
| B-2-9-9 | CH$_2$CH$_2$ | h1 | |
| B-2-9-10 | CH$_2$CH$_2$ | h2 | |
| B-2-9-11 | CH$_2$CH$_2$ | h3 | |
| B-2-9-12 | CH$_2$CH$_2$ | h4 | |
| B-2-9-13 | CH$_2$CH$_2$ | h5 | |
| B-2-9-14 | CH$_2$CH$_2$ | h6 | |
| B-2-9-15 | CH$_2$CH$_2$ | h7 | |
| B-2-9-16 | CH$_2$CH$_2$ | h8 | |
| B-2-9-17 | CH$_2$CH$_2$CH$_2$ | h1 | |
| B-2-9-18 | CH$_2$CH$_2$CH$_2$ | h2 | |
| B-2-9-19 | CH$_2$CH$_2$CH$_2$ | h3 | |
| B-2-9-20 | CH$_2$CH$_2$CH$_2$ | h4 | |
| B-2-9-21 | CH$_2$CH$_2$CH$_2$ | h5 | |
| B-2-9-22 | CH$_2$CH$_2$CH$_2$ | h6 | |
| B-2-9-23 | CH$_2$CH$_2$CH$_2$ | h7 | |
| B-2-9-24 | CH$_2$CH$_2$CH$_2$ | h8 | |
| B-2-9-25 | CH$_2$CH$_2$CH$_2$CH$_2$CH$_2$CH$_2$ | h1 | |
| B-2-9-26 | CH$_2$CH$_2$CH$_2$CH$_2$CH$_2$CH$_2$ | h2 | |
| B-2-9-27 | CH$_2$CH$_2$CH$_2$CH$_2$CH$_2$CH$_2$ | h3 | |

TABLE 19-continued

| Compound No. | D | Z | Physical Constant [ ] m.p. °C. $n_D$ refractive index |
|---|---|---|---|
| B-2-9-28 | CH$_2$CH$_2$CH$_2$CH$_2$CH$_2$CH$_2$ | h4 | |
| B-2-9-29 | CH$_2$CH$_2$CH$_2$CH$_2$CH$_2$CH$_2$ | h5 | |
| B-2-9-30 | CH$_2$CH$_2$CH$_2$CH$_2$CH$_2$CH$_2$ | h6 | |
| B-2-9-31 | CH$_2$CH$_2$CH$_2$CH$_2$CH$_2$CH$_2$ | h7 | |
| B-2-9-32 | CH$_2$CH$_2$CH$_2$CH$_2$CH$_2$CH$_2$ | h8 | |

TABLE 20

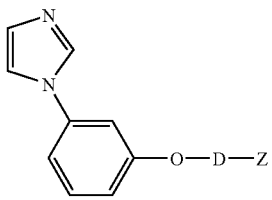

| Compound No. | D | Z | Physical Constant [ ] m.p. °C. $n_D$ refractive index |
|---|---|---|---|
| B-2-10-1 | CH$_2$ | h1 | |
| B-2-10-2 | CH$_2$ | h2 | |

TABLE 20-continued

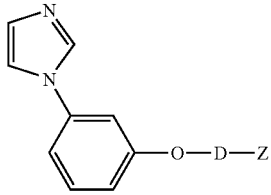

| Compound No. | D | Z | Physical Constant [ ] m.p. °C. $n_D$ refractive index |
|---|---|---|---|
| B-2-10-3 | $CH_2$ | h3 | |
| B-2-10-4 | $CH_2$ | h4 | |
| B-2-10-5 | $CH_2$ | h5 | |
| B-2-10-6 | $CH_2$ | h6 | |
| B-2-10-7 | $CH_2$ | h7 | |
| B-2-10-8 | $CH_2$ | h8 | |
| B-2-10-9 | $CH_2CH_2$ | h1 | |
| B-2-10-10 | $CH_2CH_2$ | h2 | |
| B-2-10-11 | $CH_2CH_2$ | h3 | |
| B-2-10-12 | $CH_2CH_2$ | h4 | |
| B-2-10-13 | $CH_2CH_2$ | h5 | |
| B-2-10-14 | $CH_2CH_2$ | h6 | |
| B-2-10-15 | $CH_2CH_2$ | h7 | |
| B-2-10-16 | $CH_2CH_2$ | h8 | |
| B-2-10-17 | $CH_2CH_2CH_2$ | h1 | |
| B-2-10-18 | $CH_2CH_2CH_2$ | h2 | |
| B-2-10-19 | $CH_2CH_2CH_2$ | h3 | |
| B-2-10-20 | $CH_2CH_2CH_2$ | h4 | |
| B-2-10-21 | $CH_2CH_2CH_2$ | h5 | |
| B-2-10-22 | $CH_2CH_2CH_2$ | h6 | |
| B-2-10-23 | $CH_2CH_2CH_2$ | h7 | |
| B-2-10-24 | $CH_2CH_2CH_2$ | h8 | |
| B-2-10-25 | $CH_2CH_2CH_2CH_2CH_2CH_2$ | h1 | |
| B-2-10-26 | $CH_2CH_2CH_2CH_2CH_2CH_2$ | h2 | |
| B-2-10-27 | $CH_2CH_2CH_2CH_2CH_2CH_2$ | h3 | |
| B-2-10-28 | $CH_2CH_2CH_2CH_2CH_2CH_2$ | h4 | |
| B-2-10-29 | $CH_2CH_2CH_2CH_2CH_2CH_2$ | h5 | |
| B-2-10-30 | $CH_2CH_2CH_2CH_2CH_2CH_2$ | h6 | |
| B-2-10-31 | $CH_2CH_2CH_2CH_2CH_2CH_2$ | h7 | |
| B-2-10-32 | $CH_2CH_2CH_2CH_2CH_2CH_2$ | h8 | |

TABLE 21

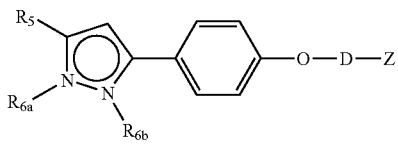

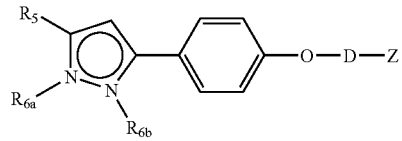

| Compound No. | $R_5$ | $R_{6a}$ | $R_{6b}$ | D | Z | Physical Constant [ ] m.p. °C. $n_D$ refractive index |
|---|---|---|---|---|---|---|
| B-2-11-1 | H | H | H | $CH_2$ | h1 | [180-184] |
| B-2-11-2 | H | H | H | $CH_2$ | h2 | [126-128] |
| B-2-11-3 | H | H | H | $CH_2$ | h3 | |
| B-2-11-4 | H | H | H | $CH_2$ | h4 | |
| B-2-11-5 | H | H | H | $CH_2$ | h5 | |
| B-2-11-6 | H | H | H | $CH_2$ | h6 | |
| B-2-11-7 | H | H | H | $CH_2$ | h7 | |
| B-2-11-8 | H | H | H | $CH_2$ | h8 | |
| B-2-11-9 | H | H | H | $CH_2CH_2$ | h1 | |
| B-2-11-10 | H | H | H | $CH_2CH_2$ | h2 | |
| B-2-11-11 | H | H | H | $CH_2CH_2$ | h3 | |
| B-2-11-12 | H | H | H | $CH_2CH_2$ | h4 | |
| B-2-11-13 | H | H | H | $CH_2CH_2$ | h5 | |
| B-2-11-14 | H | H | H | $CH_2CH_2$ | h6 | |
| B-2-11-15 | H | H | H | $CH_2CH_2$ | h7 | |
| B-2-11-16 | H | H | H | $CH_2CH_2$ | h8 | |
| B-2-11-17 | H | H | H | $CH_2CH_2CH_2$ | h1 | |
| B-2-11-18 | H | H | H | $CH_2CH_2CH_2$ | h2 | |
| B-2-11-19 | H | H | H | $CH_2CH_2CH_2$ | h3 | |
| B-2-11-20 | H | H | H | $CH_2CH_2CH_2$ | h4 | |
| B-2-11-21 | H | H | H | $CH_2CH_2CH_2$ | h5 | |
| B-2-11-22 | H | H | H | $CH_2CH_2CH_2$ | h6 | |
| B-2-11-23 | H | H | H | $CH_2CH_2CH_2$ | h7 | |
| B-2-11-24 | H | H | H | $CH_2CH_2CH_2$ | h8 | |
| B-2-11-25 | H | H | H | $CH_2CH_2CH_2CH_2CH_2CH_2$ | h1 | |
| B-2-11-26 | H | H | H | $CH_2CH_2CH_2CH_2CH_2CH_2$ | h2 | |
| B-2-11-27 | H | H | H | $CH_2CH_2CH_2CH_2CH_2CH_2$ | h3 | |
| B-2-11-28 | H | H | H | $CH_2CH_2CH_2CH_2CH_2CH_2$ | h4 | |
| B-2-11-29 | H | H | H | $CH_2CH_2CH_2CH_2CH_2CH_2$ | h5 | |
| B-2-11-30 | H | H | H | $CH_2CH_2CH_2CH_2CH_2CH_2$ | h6 | |
| B-2-11-31 | H | H | H | $CH_2CH_2CH_2CH_2CH_2CH_2$ | h7 | |
| B-2-11-32 | H | H | H | $CH_2CH_2CH_2CH_2CH_2CH_2$ | h8 | |
| B-2-11-33 | $CH_3$ | H | H | $CH_2$ | h1 | |
| B-2-11-34 | $CH_3$ | H | H | $CH_2$ | h2 | |
| B-2-11-35 | $CH_3$ | H | H | $CH_2$ | h3 | |
| B-2-11-36 | $CH_3$ | H | H | $CH_2$ | h4 | |
| B-2-11-37 | $CH_3$ | H | H | $CH_2$ | h5 | |
| B-2-11-38 | $CH_3$ | H | H | $CH_2$ | h6 | |
| B-2-11-39 | $CH_3$ | H | H | $CH_2$ | h7 | |
| B-2-11-40 | $CH_3$ | H | H | $CH_2$ | h8 | |
| B-2-11-41 | H | $CH_3$ | H | $CH_2$ | h1 | |
| B-2-11-42 | H | $CH_3$ | H | $CH_2$ | h2 | |
| B-2-11-43 | H | $CH_3$ | H | $CH_2$ | h3 | |
| B-2-11-44 | H | $CH_3$ | H | $CH_2$ | h4 | |
| B-2-11-45 | H | $CH_3$ | H | $CH_2$ | h5 | |
| B-2-11-46 | H | $CH_3$ | H | $CH_2$ | h6 | |
| B-2-11-47 | H | $CH_3$ | H | $CH_2$ | h7 | |
| B-2-11-48 | H | $CH_3$ | H | $CH_2$ | h8 | |
| B-2-11-49 | H | H | $CH_3$ | $CH_2$ | h1 | |
| B-2-11-50 | H | H | $CH_3$ | $CH_2$ | h2 | |
| B-2-11-51 | H | H | $CH_3$ | $CH_2$ | h3 | |
| B-2-11-52 | H | H | $CH_3$ | $CH_2$ | h4 | |
| B-2-11-53 | H | H | $CH_3$ | $CH_2$ | h5 | |
| B-2-11-54 | H | H | $CH_3$ | $CH_2$ | h6 | |
| B-2-11-55 | H | H | $CH_3$ | $CH_2$ | h7 | |
| B-2-11-56 | H | H | $CH_3$ | $CH_2$ | h8 | |

TABLE 22

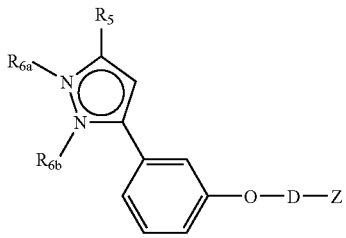

| Compound No. | $R_5$ | $R_{6a}$ | $R_{6b}$ | D | Z | Physical Constant [ ] m.p. °C. $n_D$ refractive index |
|---|---|---|---|---|---|---|
| B-2-12-1 | H | H | H | $CH_2$ | h1 | |
| B-2-12-2 | H | H | H | $CH_2$ | h2 | |
| B-2-12-3 | H | H | H | $CH_2$ | h3 | |
| B-2-12-4 | H | H | H | $CH_2$ | h4 | |
| B-2-12-5 | H | H | H | $CH_2$ | h5 | |
| B-2-12-6 | H | H | H | $CH_2$ | h6 | |
| B-2-12-7 | H | H | H | $CH_2$ | h7 | |
| B-2-12-8 | H | H | H | $CH_2$ | h8 | |
| B-2-12-9 | H | H | H | $CH_2CH_2$ | h1 | |
| B-2-12-10 | H | H | H | $CH_2CH_2$ | h2 | |
| B-2-12-11 | H | H | H | $CH_2CH_2$ | h3 | |
| B-2-12-12 | H | H | H | $CH_2CH_2$ | h4 | |
| B-2-12-13 | H | H | H | $CH_2CH_2$ | h5 | |
| B-2-12-14 | H | H | H | $CH_2CH_2$ | h6 | |
| B-2-12-15 | H | H | H | $CH_2CH_2$ | h7 | |
| B-2-12-16 | H | H | H | $CH_2CH_2$ | h8 | |
| B-2-12-17 | H | H | H | $CH_2CH_2CH_2$ | h1 | |
| B-2-12-18 | H | H | H | $CH_2CH_2CH_2$ | h2 | |
| B-2-12-19 | H | H | H | $CH_2CH_2CH_2$ | h3 | |
| B-2-12-20 | H | H | H | $CH_2CH_2CH_2$ | h4 | |
| B-2-12-21 | H | H | H | $CH_2CH_2CH_2$ | h5 | |
| B-2-12-22 | H | H | H | $CH_2CH_2CH_2$ | h6 | |
| B-2-12-23 | H | H | H | $CH_2CH_2CH_2$ | h7 | |
| B-2-12-24 | H | H | H | $CH_2CH_2CH_2$ | h8 | |
| B-2-12-25 | H | H | H | $CH_2CH_2CH_2CH_2CH_2CH_2$ | h1 | |
| B-2-12-26 | H | H | H | $CH_2CH_2CH_2CH_2CH_2CH_2$ | h2 | |
| B-2-12-27 | H | H | H | $CH_2CH_2CH_2CH_2CH_2CH_2$ | h3 | |
| B-2-12-28 | H | H | H | $CH_2CH_2CH_2CH_2CH_2CH_2$ | h4 | |
| B-2-12-29 | H | H | H | $CH_2CH_2CH_2CH_2CH_2CH_2$ | h5 | |
| B-2-12-30 | H | H | H | $CH_2CH_2CH_2CH_2CH_2CH_2$ | h6 | |
| B-2-12-31 | H | H | H | $CH_2CH_2CH_2CH_2CH_2CH_2$ | h7 | |
| B-2-12-32 | H | H | H | $CH_2CH_2CH_2CH_2CH_2CH_2$ | h8 | |
| B-2-12-33 | $CH_3$ | H | H | $CH_2$ | h1 | |
| B-2-12-34 | $CH_3$ | H | H | $CH_2$ | h2 | |
| B-2-12-35 | $CH_3$ | H | H | $CH_2$ | h3 | |
| B-2-12-36 | $CH_3$ | H | H | $CH_2$ | h4 | |
| B-2-12-37 | $CH_3$ | H | H | $CH_2$ | h5 | |
| B-2-12-38 | $CH_3$ | H | H | $CH_2$ | h6 | |
| B-2-12-39 | $CH_3$ | H | H | $CH_2$ | h7 | |
| B-2-12-40 | $CH_3$ | H | H | $CH_2$ | h8 | |
| B-2-12-41 | H | $CH_3$ | H | $CH_2$ | h1 | |
| B-2-12-42 | H | $CH_3$ | H | $CH_2$ | h2 | |
| B-2-12-43 | H | $CH_3$ | H | $CH_2$ | h3 | |
| B-2-12-44 | H | $CH_3$ | H | $CH_2$ | h4 | |
| B-2-12-45 | H | $CH_3$ | H | $CH_2$ | h5 | |
| B-2-12-46 | H | $CH_3$ | H | $CH_2$ | h6 | |
| B-2-12-47 | H | $CH_3$ | H | $CH_2$ | h7 | |
| B-2-12-48 | H | $CH_3$ | H | $CH_2$ | h8 | |
| B-2-12-49 | H | H | $CH_3$ | $CH_2$ | h1 | |
| B-2-12-50 | H | H | $CH_3$ | $CH_2$ | h2 | |
| B-2-12-51 | H | H | $CH_3$ | $CH_2$ | h3 | |
| B-2-12-52 | H | H | $CH_3$ | $CH_2$ | h4 | |
| B-2-12-53 | H | H | $CH_3$ | $CH_2$ | h5 | |
| B-2-12-54 | H | H | $CH_3$ | $CH_2$ | h6 | |

TABLE 22-continued

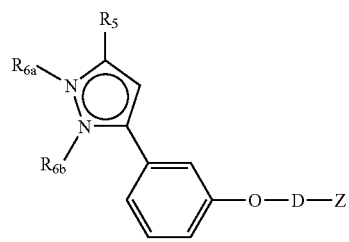

| Compound No. | $R_5$ | $R_{6a}$ | $R_{6b}$ | D | Z | Physical Constant [ ] m.p. °C. $n_D$ refractive index |
|---|---|---|---|---|---|---|
| B-2-12-55 | H | H | $CH_3$ | $CH_2$ | h7 | |
| B-2-12-56 | H | H | $CH_3$ | $CH_2$ | h8 | |

TABLE 23

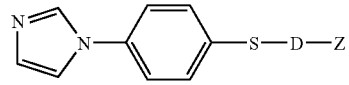

| Compound No. | D | Z | Physical Constant [ ] m.p. °C. $n_D$ refractive index |
|---|---|---|---|
| B-2-13-1 | $CH_2$ | h1 | & NMR |
| B-2-13-2 | $CH_2$ | h2 | |
| B-2-13-3 | $CH_2$ | h3 | |
| B-2-13-4 | $CH_2$ | h4 | |
| B-2-13-5 | $CH_2$ | h5 | |
| B-2-13-6 | $CH_2$ | h6 | |
| B-2-13-7 | $CH_2$ | h7 | |
| B-2-13-8 | $CH_2$ | h8 | |
| B-2-13-9 | $CH_2CH_2$ | h1 | |
| B-2-13-10 | $CH_2CH_2$ | h2 | |
| B-2-13-11 | $CH_2CH_2$ | h3 | |
| B-2-13-12 | $CH_2CH_2$ | h4 | |
| B-2-13-13 | $CH_2CH_2$ | h5 | |
| B-2-13-14 | $CH_2CH_2$ | h6 | |
| B-2-13-15 | $CH_2CH_2$ | h7 | |
| B-2-13-16 | $CH_2CH_2$ | h8 | |
| B-2-13-17 | $CH_2CH_2CH_2$ | h1 | |
| B-2-13-18 | $CH_2CH_2CH_2$ | h2 | |
| B-2-13-19 | $CH_2CH_2CH_2$ | h3 | |
| B-2-13-20 | $CH_2CH_2CH_2$ | h4 | |
| B-2-13-21 | $CH_2CH_2CH_2$ | h5 | |
| B-2-13-22 | $CH_2CH_2CH_2$ | h6 | |
| B-2-13-23 | $CH_2CH_2CH_2$ | h7 | |
| B-2-13-24 | $CH_2CH_2CH_2$ | h8 | |
| B-2-13-25 | $CH_2CH_2CH_2CH_2CH_2CH_2$ | h1 | |
| B-2-13-26 | $CH_2CH_2CH_2CH_2CH_2CH_2$ | h2 | |
| B-2-13-27 | $CH_2CH_2CH_2CH_2CH_2CH_2$ | h3 | |
| B-2-13-28 | $CH_2CH_2CH_2CH_2CH_2CH_2$ | h4 | |
| B-2-13-29 | $CH_2CH_2CH_2CH_2CH_2CH_2$ | h5 | |
| B-2-13-30 | $CH_2CH_2CH_2CH_2CH_2CH_2$ | h6 | |
| B-2-13-31 | $CH_2CH_2CH_2CH_2CH_2CH_2$ | h7 | |
| B-2-13-32 | $CH_2CH_2CH_2CH_2CH_2CH_2$ | h8 | |

TABLE 24

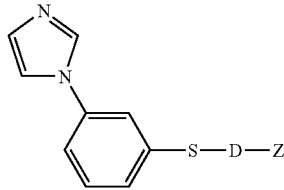

| Compound No. | D | Z | Physical Constant [ ] m.p. °C. $n_D$ refractive index |
|---|---|---|---|
| B-2-14-1 | $CH_2$ | h1 | |
| B-2-14-2 | $CH_2$ | h2 | |
| B-2-14-3 | $CH_2$ | h3 | |
| B-2-14-4 | $CH_2$ | h4 | |
| B-2-14-5 | $CH_2$ | h5 | |
| B-2-14-6 | $CH_2$ | h6 | |
| B-2-14-7 | $CH_2$ | h7 | |
| B-2-14-8 | $CH_2$ | h8 | |
| B-2-14-9 | $CH_2CH_2$ | h1 | |
| B-2-14-10 | $CH_2CH_2$ | h2 | |
| B-2-14-11 | $CH_2CH_2$ | h3 | |
| B-2-14-12 | $CH_2CH_2$ | h4 | |
| B-2-14-13 | $CH_2CH_2$ | h5 | |
| B-2-14-14 | $CH_2CH_2$ | h6 | |
| B-2-14-15 | $CH_2CH_2$ | h7 | |
| B-2-14-16 | $CH_2CH_2$ | h8 | |
| B-2-14-17 | $CH_2CH_2CH_2$ | h1 | |
| B-2-14-18 | $CH_2CH_2CH_2$ | h2 | |
| B-2-14-19 | $CH_2CH_2CH_2$ | h3 | |
| B-2-14-20 | $CH_2CH_2CH_2$ | h4 | |
| B-2-14-21 | $CH_2CH_2CH_2$ | h5 | |
| B-2-14-22 | $CH_2CH_2CH_2$ | h6 | |
| B-2-14-23 | $CH_2CH_2CH_2$ | h7 | |
| B-2-14-24 | $CH_2CH_2CH_2$ | h8 | |
| B-2-14-25 | $CH_2CH_2CH_2CH_2CH_2CH_2$ | h1 | |
| B-2-14-26 | $CH_2CH_2CH_2CH_2CH_2CH_2$ | h2 | |
| B-2-14-27 | $CH_2CH_2CH_2CH_2CH_2CH_2$ | h3 | |
| B-2-14-28 | $CH_2CH_2CH_2CH_2CH_2CH_2$ | h4 | |
| B-2-14-29 | $CH_2CH_2CH_2CH_2CH_2CH_2$ | h5 | |
| B-2-14-30 | $CH_2CH_2CH_2CH_2CH_2CH_2$ | h6 | |
| B-2-14-31 | $CH_2CH_2CH_2CH_2CH_2CH_2$ | h7 | |
| B-2-14-32 | $CH_2CH_2CH_2CH_2CH_2CH_2$ | h8 | |

TABLE 25

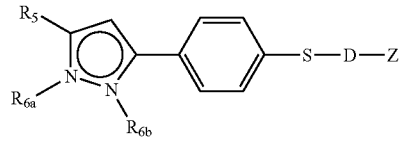

| Compound No. | $R_5$ | $R_{6a}$ | $R_{6b}$ | D | Z | Physical Constant [ ] m.p. °C. $n_D$ refractive index |
|---|---|---|---|---|---|---|
| B-2-15-1 | H | H | H | $CH_2$ | h1 | |
| B-2-15-2 | H | H | H | $CH_2$ | h2 | |
| B-2-15-3 | H | H | H | $CH_2$ | h3 | |
| B-2-15-4 | H | H | H | $CH_2$ | h4 | |
| B-2-15-5 | H | H | H | $CH_2$ | h5 | |
| B-2-15-6 | H | H | H | $CH_2$ | h6 | |
| B-2-15-7 | H | H | H | $CH_2$ | h7 | |
| B-2-15-8 | H | H | H | $CH_2$ | h8 | |
| B-2-15-9 | H | H | H | $CH_2CH_2$ | h1 | |
| B-2-15-10 | H | H | H | $CH_2CH_2$ | h2 | |
| B-2-15-11 | H | H | H | $CH_2CH_2$ | h3 | |
| B-2-15-12 | H | H | H | $CH_2CH_2$ | h4 | |
| B-2-15-13 | H | H | H | $CH_2CH_2$ | h5 | |
| B-2-15-14 | H | H | H | $CH_2CH_2$ | h6 | |
| B-2-15-15 | H | H | H | $CH_2CH_2$ | h7 | |
| B-2-15-16 | H | H | H | $CH_2CH_2$ | h8 | |
| B-2-15-17 | H | H | H | $CH_2CH_2CH_2$ | h1 | |
| B-2-15-18 | H | H | H | $CH_2CH_2CH_2$ | h2 | |
| B-2-15-19 | H | H | H | $CH_2CH_2CH_2$ | h3 | |
| B-2-15-20 | H | H | H | $CH_2CH_2CH_2$ | h4 | |
| B-2-15-21 | H | H | H | $CH_2CH_2CH_2$ | h5 | |
| B-2-15-22 | H | H | H | $CH_2CH_2CH_2$ | h6 | |
| B-2-15-23 | H | H | H | $CH_2CH_2CH_2$ | h7 | |
| B-2-15-24 | H | H | H | $CH_2CH_2CH_2$ | h8 | |
| B-2-15-25 | H | H | H | $CH_2CH_2CH_2CH_2CH_2CH_2$ | h1 | |
| B-2-15-26 | H | H | H | $CH_2CH_2CH_2CH_2CH_2CH_2$ | h2 | |
| B-2-15-27 | H | H | H | $CH_2CH_2CH_2CH_2CH_2CH_2$ | h3 | |
| B-2-15-28 | H | H | H | $CH_2CH_2CH_2CH_2CH_2CH_2$ | h4 | |
| B-2-15-29 | H | H | H | $CH_2CH_2CH_2CH_2CH_2CH_2$ | h5 | |
| B-2-15-30 | H | H | H | $CH_2CH_2CH_2CH_2CH_2CH_2$ | h6 | |
| B-2-15-31 | H | H | H | $CH_2CH_2CH_2CH_2CH_2CH_2$ | h7 | |
| B-2-15-32 | H | H | H | $CH_2CH_2CH_2CH_2CH_2CH_2$ | h8 | |
| B-2-15-33 | $CH_3$ | H | H | $CH_2$ | h1 | |
| B-2-15-34 | $CH_3$ | H | H | $CH_2$ | h2 | |
| B-2-15-35 | $CH_3$ | H | H | $CH_2$ | h3 | |
| B-2-15-36 | $CH_3$ | H | H | $CH_2$ | h4 | |
| B-2-15-37 | $CH_3$ | H | H | $CH_2$ | h5 | |
| B-2-15-38 | $CH_3$ | H | H | $CH_2$ | h6 | |
| B-2-15-39 | $CH_3$ | H | H | $CH_2$ | h7 | |
| B-2-15-40 | $CH_3$ | H | H | $CH_2$ | h8 | |
| B-2-15-41 | H | $CH_3$ | H | $CH_2$ | h1 | |
| B-2-15-42 | H | $CH_3$ | H | $CH_2$ | h2 | |
| B-2-15-43 | H | $CH_3$ | H | $CH_2$ | h3 | |
| B-2-15-44 | H | $CH_3$ | H | $CH_2$ | h4 | |
| B-2-15-45 | H | $CH_3$ | H | $CH_2$ | h5 | |
| B-2-15-46 | H | $CH_3$ | H | $CH_2$ | h6 | |
| B-2-15-47 | H | $CH_3$ | H | $CH_2$ | h7 | |
| B-2-15-48 | H | $CH_3$ | H | $CH_2$ | h8 | |
| B-2-15-49 | H | H | $CH_3$ | $CH_2$ | h1 | |
| B-2-15-50 | H | H | $CH_3$ | $CH_2$ | h2 | |
| B-2-15-51 | H | H | $CH_3$ | $CH_2$ | h3 | |
| B-2-15-52 | H | H | $CH_3$ | $CH_2$ | h4 | |
| B-2-15-53 | H | H | $CH_3$ | $CH_2$ | h5 | |
| B-2-15-54 | H | H | $CH_3$ | $CH_2$ | h6 | |
| B-2-15-55 | H | H | $CH_3$ | $CH_2$ | h7 | |
| B-2-15-56 | H | H | $CH_3$ | $CH_2$ | h8 | |

TABLE 26

[Structure: pyrazole with R5, R6a, R6b substituents connected to phenyl-S-D-Z]

| Compound No. | R5 | R6a | R6b | D | Z | Physical Constant [ ] m.p. °C. nD refractive index |
|---|---|---|---|---|---|---|
| B-2-16-1 | H | H | H | CH₂ | h1 | |
| B-2-16-2 | H | H | H | CH₂ | h2 | |
| B-2-16-3 | H | H | H | CH₂ | h3 | |
| B-2-16-4 | H | H | H | CH₂ | h4 | |
| B-2-16-5 | H | H | H | CH₂ | h5 | |
| B-2-16-6 | H | H | H | CH₂ | h6 | |
| B-2-16-7 | H | H | H | CH₂ | h7 | |
| B-2-16-8 | H | H | H | CH₂ | h8 | |
| B-2-16-9 | H | H | H | CH₂CH₂ | h1 | |
| B-2-16-10 | H | H | H | CH₂CH₂ | h2 | |
| B-2-16-11 | H | H | H | CH₂CH₂ | h3 | |
| B-2-16-12 | H | H | H | CH₂CH₂ | h4 | |
| B-2-16-13 | H | H | H | CH₂CH₂ | h5 | |
| B-2-16-14 | H | H | H | CH₂CH₂ | h6 | |
| B-2-16-15 | H | H | H | CH₂CH₂ | h7 | |
| B-2-16-16 | H | H | H | CH₂CH₂ | h8 | |
| B-2-16-17 | H | H | H | CH₂CH₂CH₂ | h1 | |
| B-2-16-18 | H | H | H | CH₂CH₂CH₂ | h2 | |
| B-2-16-19 | H | H | H | CH₂CH₂CH₂ | h3 | |
| B-2-16-20 | H | H | H | CH₂CH₂CH₂ | h4 | |
| B-2-16-21 | H | H | H | CH₂CH₂CH₂ | h5 | |
| B-2-16-22 | H | H | H | CH₂CH₂CH₂ | h6 | |
| B-2-16-23 | H | H | H | CH₂CH₂CH₂ | h7 | |
| B-2-16-24 | H | H | H | CH₂CH₂CH₂ | h8 | |
| B-2-16-25 | H | H | H | CH₂CH₂CH₂CH₂CH₂ | h1 | |
| B-2-16-26 | H | H | H | CH₂CH₂CH₂CH₂CH₂ | h2 | |
| B-2-16-27 | H | H | H | CH₂CH₂CH₂CH₂CH₂ | h3 | |
| B-2-16-28 | H | H | H | CH₂CH₂CH₂CH₂CH₂ | h4 | |
| B-2-16-29 | H | H | H | CH₂CH₂CH₂CH₂CH₂ | h5 | |
| B-2-16-30 | H | H | H | CH₂CH₂CH₂CH₂CH₂ | h6 | |
| B-2-16-31 | H | H | H | CH₂CH₂CH₂CH₂CH₂ | h7 | |
| B-2-16-32 | H | H | H | CH₂CH₂CH₂CH₂CH₂ | h8 | |
| B-2-16-33 | CH₃ | H | H | CH₂ | h1 | |
| B-2-16-34 | CH₃ | H | H | CH₂ | h2 | |
| B-2-16-35 | CH₃ | H | H | CH₂ | h3 | |
| B-2-16-36 | CH₃ | H | H | CH₂ | h4 | |
| B-2-16-37 | CH₃ | H | H | CH₂ | h5 | |
| B-2-16-38 | CH₃ | H | H | CH₂ | h6 | |
| B-2-16-39 | CH₃ | H | H | CH₂ | h7 | |
| B-2-16-40 | CH₃ | H | H | CH₂ | h8 | |
| B-2-16-41 | H | CH₃ | H | CH₂ | h1 | |
| B-2-16-42 | H | CH₃ | H | CH₂ | h2 | |
| B-2-16-43 | H | CH₃ | H | CH₂ | h3 | |
| B-2-16-44 | H | CH₃ | H | CH₂ | h4 | |
| B-2-16-45 | H | CH₃ | H | CH₂ | h5 | |
| B-2-16-46 | H | CH₃ | H | CH₂ | h6 | |
| B-2-16-47 | H | CH₃ | H | CH₂ | h7 | |
| B-2-16-48 | H | CH₃ | H | CH₂ | h8 | |
| B-2-16-49 | H | H | CH₃ | CH₂ | h1 | |
| B-2-16-50 | H | H | CH₃ | CH₂ | h2 | |
| B-2-16-51 | H | H | CH₃ | CH₂ | h3 | |
| B-2-16-52 | H | H | CH₃ | CH₂ | h4 | |
| B-2-16-53 | H | H | CH₃ | CH₂ | h5 | |
| B-2-16-54 | H | H | CH₃ | CH₂ | h6 | |
| B-2-16-55 | H | H | CH₃ | CH₂ | h7 | |
| B-2-16-56 | H | H | CH₃ | CH₂ | h8 | |

TABLE 27

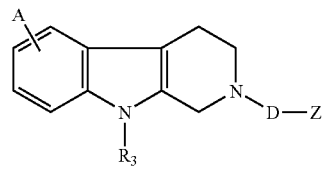

| Compound No. | A | R₃ | D | Z | Physical Constant [ ] m.p. °C |
|---|---|---|---|---|---|
| B-3-1 | — | H | CH₂ | h1 | [150-153] |
| B-3-2 | — | H | CH₂ | h2 | |
| B-3-3 | — | H | CH₂ | h3 | |
| B-3-4 | 6-OMe | H | CH₂ | h1 | |
| B-3-5 | 6-OMe | H | CH₂ | h2 | |
| B-3-6 | 6-OMe | H | CH₂ | h3 | |
| B-3-7 | 6-(1-imidazolyl) | H | CH₂ | h1 | |
| B-3-8 | 6-(1-imidazolyl) | H | CH₂ | h2 | |
| B-3-9 | 6-(1-imidazolyl) | H | CH₂ | h3 | |
| B-3-10 | — | H | CO | h1 | [129-133] |
| B-3-11 | — | H | CO | h2 | |
| B-3-12 | — | H | CO | h3 | |
| B-3-13 | 6-OMe | H | CO | h1 | |
| B-3-14 | 6-OMe | H | CO | h2 | |
| B-3-15 | 6-OMe | H | CO | h3 | |
| B-3-16 | 6-(1-imidazolyl) | H | CO | h1 | |
| B-3-17 | 6-(1-imidazolyl) | H | CO | h2 | |
| B-3-18 | 6-(1-imidazolyl) | H | CO | h3 | |
| B-3-19 | — | Me | CH₂ | h1 | |
| B-3-20 | — | Me | CH₂ | h2 | |
| B-3-21 | — | Me | CH₂ | h3 | |
| B-3-22 | 6-OMe | Me | CH₂ | h1 | |
| B-3-23 | 6-OMe | Me | CH₂ | h2 | |
| B-3-24 | 6-OMe | Me | CH₂ | h3 | |
| B-3-25 | 6-(1-imidazolyl) | Me | CH₂ | h1 | |
| B-3-26 | 6-(1-imidazolyl) | Me | CH₂ | h2 | |
| B-3-27 | 6-(1-imidazolyl) | Me | CH₂ | h3 | |
| B-3-28 | — | Me | CO | h1 | |
| B-3-29 | — | Me | CO | h2 | |
| B-3-30 | — | Me | CO | h3 | |
| B-3-31 | 6-OMe | Me | CO | h1 | |
| B-3-32 | 6-OMe | Me | CO | h2 | |
| B-3-33 | 6-OMe | Me | CO | h3 | |
| B-3-34 | 6-(1-imidazolyl) | Me | CO | h1 | |

TABLE 27-continued

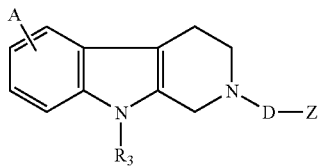

| Compound No. | A | R₃ | D | Z | Physical Constant [ ] m.p. ° C. |
|---|---|---|---|---|---|
| B-3-35 | 6-(1-imidazolyl) | Me | CO | h2 | |
| B-3-36 | 6-(1-imidazolyl) | Me | CO | h3 | |
| B-3-37 | — | CH₂Ph | CH₂ | h1 | |
| B-3-38 | — | CH₂Ph | CH₂ | h2 | |
| B-3-39 | — | CH₂Ph | CH₂ | h3 | |
| B-3-40 | 6-OMe | CH₂Ph | CH₂ | h1 | |
| B-3-41 | 6-OMe | CH₂Ph | CH₂ | h2 | |
| B-3-42 | 6-OMe | CH₂Ph | CH₂ | h3 | |
| B-3-43 | 6-(1-imidazolyl) | CH₂Ph | CH₂ | h1 | |
| B-3-44 | 6-(1-imidazolyl) | CH₂Ph | CH₂ | h2 | |
| B-3-45 | 6-(1-imidazolyl) | CH₂Ph | CH₂ | h3 | |
| B-3-46 | — | CH₂Ph | CO | h1 | |
| B-3-47 | — | CH₂Ph | CO | h2 | |
| B-3-48 | — | CH₂Ph | CO | h3 | |
| B-3-49 | 6-OMe | CH₂Ph | CO | h1 | |
| B-3-50 | 6-OMe | CH₂Ph | CO | h2 | |
| B-3-51 | 6-OMe | CH₂Ph | CO | h3 | |
| B-3-52 | 6-(1-imidazolyl) | CH₂Ph | CO | h1 | |
| B-3-53 | 6-(1-imidazolyl) | CH₂Ph | CO | h2 | |
| B-3-54 | 6-(1-imidazolyl) | CH₂Ph | CO | h3 | |

TABLE 28

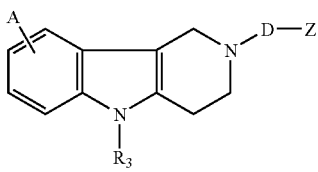

| Compound No. | A | R₃ | D | Z | Physical Constant [ ] m.p. ° C. |
|---|---|---|---|---|---|
| B-3-55 | — | H | CH₂ | h1 | & NMR |
| B-3-56 | — | H | CH₂ | h2 | |
| B-3-57 | — | H | CH₂ | h3 | |
| B-3-58 | 8-OMe | H | CH₂ | h1 | [176-180] |
| B-3-59 | 8-OMe | H | CH₂ | h2 | |
| B-3-60 | 8-OMe | H | CH₂ | h3 | |
| B-3-61 | 8-(1-imidazolyl) | H | CH₂ | h1 | [206-210] |
| B-3-62 | 8-(1-imidazolyl) | H | CH₂ | h2 | |
| B-3-63 | 8-(1-imidazolyl) | H | CH₂ | h3 | |
| B-3-64 | — | H | CO | h1 | [253-257] |
| B-3-65 | — | H | CO | h2 | |
| B-3-66 | — | H | CO | h3 | |
| B-3-67 | 8-OMe | H | CO | h1 | |
| B-3-68 | 8-OMe | H | CO | h2 | |
| B-3-69 | 8-OMe | H | CO | h3 | |
| B-3-70 | 8-(1-imidazolyl) | H | CO | h1 | |
| B-3-71 | 8-(1-imidazolyl) | H | CO | h2 | |
| B-3-72 | 8-(1-imidazolyl) | H | CO | h3 | |
| B-3-73 | — | Me | CH₂ | h1 | [179-183] |
| B-3-74 | — | Me | CH₂ | h2 | |
| B-3-75 | — | Me | CH₂ | h3 | |
| B-3-76 | 8-OMe | Me | CH₂ | h1 | |
| B-3-77 | 8-OMe | Me | CH₂ | h2 | |
| B-3-78 | 8-OMe | Me | CH₂ | h3 | |
| B-3-79 | 8-(1-imidazolyl) | Me | CH₂ | h1 | |
| B-3-80 | 8-(1-imidazolyl) | Me | CH₂ | h2 | |
| B-3-81 | 8-(1-imidazolyl) | Me | CH₂ | h3 | |
| B-3-82 | — | Me | CO | h1 | |
| B-3-83 | — | Me | CO | h2 | |
| B-3-84 | — | Me | CO | h3 | |

TABLE 28-continued

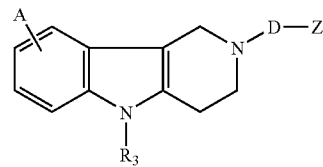

| Compound No. | A | R₃ | D | Z | Physical Constant [ ] m.p. ° C. |
|---|---|---|---|---|---|
| B-3-85 | 8-OMe | Me | CO | h1 | |
| B-3-86 | 8-OMe | Me | CO | h2 | |
| B-3-87 | 8-OMe | Me | CO | h3 | |
| B-3-88 | 8-(1-imidazolyl) | Me | CO | h1 | |
| B-3-89 | 8-(1-imidazolyl) | Me | CO | h2 | |
| B-3-90 | 8-(1-imidazolyl) | Me | CO | h3 | |
| B-3-91 | — | CH₂Ph | CH₂ | h1 | |
| B-3-92 | — | CH₂Ph | CH₂ | h2 | |
| B-3-93 | — | CH₂Ph | CH₂ | h3 | |
| B-3-94 | 8-OMe | CH₂Ph | CH₂ | h1 | |
| B-3-95 | 8-OMe | CH₂Ph | CH₂ | h2 | |
| B-3-96 | 8-OMe | CH₂Ph | CH₂ | h3 | |
| B-3-97 | 8-(1-imidazolyl) | CH₂Ph | CH₂ | h1 | |
| B-3-98 | 8-(1-imidazolyl) | CH₂Ph | CH₂ | h2 | |
| B-3-99 | 8-(1-imidazolyl) | CH₂Ph | CH₂ | h3 | |
| B-3-100 | — | CH₂Ph | CO | h1 | |
| B-3-101 | — | CH₂Ph | CO | h2 | |
| B-3-102 | — | CH₂Ph | CO | h3 | |
| B-3-103 | 8-OMe | CH₂Ph | CO | h1 | |
| B-3-104 | 8-OMe | CH₂Ph | CO | h2 | |
| B-3-105 | 8-OMe | CH₂Ph | CO | h3 | |
| B-3-106 | 8-(1-imidazolyl) | CH₂Ph | CO | h1 | |
| B-3-107 | 8-(1-imidazolyl) | CH₂Ph | CO | h2 | |
| B-3-108 | 8-(1-imidazolyl) | CH₂Ph | CO | h3 | |

TABLE 29

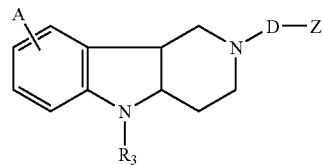

| Compound No. | A | R₃ | D | Z | Physical Constant [ ] m.p. ° C. |
|---|---|---|---|---|---|
| B-3-109 | — | H | CH₂ | h1 | [137-140] |
| B-3-110 | — | H | CH₂ | h2 | |
| B-3-111 | — | H | CH₂ | h3 | |
| B-3-112 | 8-OMe | H | CH₂ | h1 | |
| B-3-113 | 8-OMe | H | CH₂ | h2 | |
| B-3-114 | 8-OMe | H | CH₂ | h3 | |
| B-3-115 | 8-(1-imidazolyl) | H | CH₂ | h1 | |
| B-3-116 | 8-(1-imidazolyl) | H | CH₂ | h2 | |
| B-3-117 | 8-(1-imidazolyl) | H | CH₂ | h3 | |
| B-3-118 | — | H | CO | h1 | |
| B-3-119 | — | H | CO | h2 | |
| B-3-120 | — | H | CO | h3 | |
| B-3-121 | 8-OMe | H | CO | h1 | |
| B-3-122 | 8-OMe | H | CO | h2 | |
| B-3-123 | 8-OMe | H | CO | h3 | |
| B-3-124 | 8-(1-imidazolyl) | H | CO | h1 | |
| B-3-125 | 8-(1-imidazolyl) | H | CO | h2 | |
| B-3-126 | 8-(1-imidazolyl) | H | CO | h3 | |
| B-3-127 | — | Me | CH₂ | h1 | |
| B-3-128 | — | Me | CH₂ | h2 | |
| B-3-129 | — | Me | CH₂ | h3 | |
| B-3-130 | 8-OMe | Me | CH₂ | h1 | |
| B-3-131 | 8-OMe | Me | CH₂ | h2 | |
| B-3-132 | 8-OMe | Me | CH₂ | h3 | |
| B-3-133 | 8-(1-imidazolyl) | Me | CH₂ | h1 | |
| B-3-134 | 8-(1-imidazolyl) | Me | CH₂ | h2 | |

TABLE 29-continued

| Compound No. | A | R₃ | D | Z | Physical Constant [ ] m.p. ° C. |
|---|---|---|---|---|---|
| B-3-135 | 8-(1-imidazolyl) | Me | CH₂ | h3 | |
| B-3-136 | — | Me | CO | h1 | |
| B-3-137 | — | Me | CO | h2 | |
| B-3-138 | — | Me | CO | h3 | |
| B-3-139 | 8-OMe | Me | CO | h1 | |
| B-3-140 | 8-OMe | Me | CO | h2 | |
| B-3-141 | 8-OMe | Me | CO | h3 | |
| B-3-142 | 8-(1-imidazolyl) | Me | CO | h1 | |
| B-3-143 | 8-(1-imidazolyl) | Me | CO | h2 | |
| B-3-144 | 8-(1-imidazolyl) | Me | CO | h3 | |
| B-3-145 | — | CH₂Ph | CH₂ | h1 | & NMR |
| B-3-146 | — | CH₂Ph | CH₂ | h2 | |
| B-3-147 | — | CH₂Ph | CH₂ | h3 | |
| B-3-148 | 8-OMe | CH₂Ph | CH₂ | h1 | |
| B-3-149 | 8-OMe | CH₂Ph | CH₂ | h2 | |
| B-3-150 | 8-OMe | CH₂Ph | CH₂ | h3 | |
| B-3-151 | 8-(1-imidazolyl) | CH₂Ph | CH₂ | h1 | |
| B-3-152 | 8-(1-imidazolyl) | CH₂Ph | CH₂ | h2 | |
| B-3-153 | 8-(1-imidazolyl) | CH₂Ph | CH₂ | h3 | |
| B-3-154 | — | CH₂Ph | CO | h1 | |
| B-3-155 | — | CH₂Ph | CO | h2 | |
| B-3-156 | — | CH₂Ph | CO | h3 | |
| B-3-157 | 8-OMe | CH₂Ph | CO | h1 | |
| B-3-158 | 8-OMe | CH₂Ph | CO | h2 | |
| B-3-159 | 8-OMe | CH₂Ph | CO | h3 | |
| B-3-160 | 8-(1-imidazolyl) | CH₂Ph | CO | h1 | |
| B-3-161 | 8-(1-imidazolyl) | CH₂Ph | CO | h2 | |
| B-3-162 | 8-(1-imidazolyl) | CH₂Ph | CO | h3 | |

$^1$H-NMR Data (Deuterated Chloro Solvent, Internal Standard TMS)

Unit is δ, a numerical value in parenthesis indicates a proton ratio, and symbols are as follows; s: singlet, d: doublet, t: triplet, q: quartet, m: multiplet, br: broad and brs: broad singlet.

Compound B-1-11
1.7(s, 3H), 2.0(s, 6H), 2.1(s, 3H), 2.3(s, 3H), 2.9(d, 1H), 3.0-3.4(m, 4H), 3.7(m, 1H), 3.9(m, 2H), 4.0(d, 1H), 4.3(m, 1H), 6.9(d, 2H), 7.2(d, 2H), 7.25(s, 1H), 7.3(s, 1H), 7.8(s, 1H)

Compound B-1-13
1.6(s, 3H), 1.8(m, 2H), 1.9(s, 3H), 2.0(s, 3H), 2.1(s, 3H), 2.3(s, 3H), 2.5(m, 2H), 2.7(m, 1H), 3.0-4.2(m, 8H), 6.9(d, 2H), 7.2(d, 2H), 7.25(s, 1H), 7.3(s, 1H), 7.7(s, 1H)

Compound B-1-28
1.4(s, 3H), 1.92(s, 3H), 1.97(s, 3H), 2.0(s, 3H), 2.3(s, 3H), 2.6(m, 4H), 2.7(m, 3H), 3.0(d, 1H), 3.1(m, 4H), 6.7(m, 3H), 7.2(m, 3H), 7.7(s, 1H)

Compound B-1-37
1.7(s, 3H), 2.1(s, 3H), 2.15(s, 6H), 2.9(d, 1H), 3.0-3.4(m, 4H), 3.7(m, 1H), 3.9(m, 2H), 3.9(d, 1H), 4.2(m, 1H), 6.5(d, 1H), 6.9(d, 2H), 7.55(d, 1H), 7.6(d, 2H)

Compound B-1-39
1.6(s, 3H), 1.7(m, 2H), 2.0(s, 3H), 2.1(s, 3H), 2.15(s, 3H), 2.5-2.6(m, 2H), 2.7-2.8(m, 1H), 3.0-4.2(m, 8H), 6.5(d, 1H), 6.8(d, 2H), 7.1(d, 1H), 7.6(d, 2H)

Compound B-1-148
1.1(s, 3H), 1.6(m, 1H), 1.8(m, 3H), 1.9(s, 3H), 2.1(s, 6H), 2.5(m, 4H), 2.7(m, 2H), 2.9(m, 2H), 3.5(m, 4H), 6.5(s, 1H), 6.6(m, 2H), 7.1(s, 1H), 7.2(m, 2H), 7.7(s, 1H)

Compound B-1-326
1.43(s, 3H), 2.03(s, 3H), 2.12(s, 6H), 2.60(s, 2H), 2.5-2.8(m, 4H), 2.80(d, 1H), 3.10(d, 1H), 3.40(br, 2H), 3.75(br, 2H), 4.25(br, 1H), 7.22(s, 1H), 7.30(s, 1H), 7.43(d, 2H), 7.52(d, 2H), 7.90(s, 1H)

Compound B-1-332
1.43(s, 3H), 2.0(s, 6H), 2.03(s, 3H), 2.51(s, 3H), 2.4-2.8(m, 4H), 2.6(s, 2H), 2.81(d, 1H), 3.0(d, 1H), 3.4(br, 2H), 3.75(br, 2H), 7.22(s, 1H), 7.30(s, 1H), 7.43(d, 2H), 7.52(d, 2H), 7.90(s, 1H)

Compound B-2-1-4
1.3(s, 3H), 1.8(m, 1H), 2.0(m, 1H), 2.1(s, 6H), 2.15(s, 3H), 2.7(t, 2H), 3.3(d, 2H), 4.2(t, 1H), 4.7(br, 1H), 6.7(d, 2H), 7.2(m, 4H), 7.7(s, 1H)

Compound B-2-1-22
1.4(s, 3H), 1.4-1.8(m, 10H), 2.0(s, 3H), 2.05(s, 3H), 2.1(s, 3H), 2.3(s, 3H), 2.8(d, 1H), 3.0(d, 1H), 3.1(t, 2H), 3.8(br, 1H), 6.6(d, 2H), 7.2(m, 4H), 7.7(s, 1H)

Compound B-2-2-2
1.3(s, 3H), 1.8(m, 1H), 1.9(m, 1H), 2.0(s, 3H), 2.1(s, 3H), 2.2(s, 3H), 2.7(m, 2H), 3.3(m, 2H), 4.3(m, 1H), 6.5-6.7(m, 3H), 7.1(s, 1H), 7.2(s, 1H), 7.2(m, 1H), 7.8(s, 1H)

Compound B-2-5-7
1.5(s, 3H), 1.9(s, 3H), 2.0(s, 3H), 2.1(s, 3H), 2.3(s, 3H), 3.3(s, 2H), 4.0(br, 1H), 6.4(d, 1H), 6.7(d, 2H), 7.5(d, 2H), 7.55(d, 1H)

Compound B-2-8-1
1.5(s, 3H), 2.0(s, 3H), 2.05(s, 3H), 2.1(s, 3H), 2.8(d, 1H), 3.2(d, 1H), 3.3(s, 2H), 4.3(br, 2H), 6.6(d, 2H), 7.3(d, 2H), 7.7(s, 2H)

Compound B-2-8-41
1.0(t, 3h), 1.4(s, 3H), 2.0(s, 3H), 2.05(s, 3H), 2.1(s, 3H), 2.8(d, 1H), 3.0(d, 1H), 3.5(m, 4H), 6.7(d, 2H), 7.3(d, 2H), 7.7(s, 2H)

Compound B-2-13-1
1.6(s, 3H), 2.0(s, 3H), 2.0(s, 3H), 2.1(s, 3H), 2.5(br, 2H), 3.0(d, 1H), 3.2(d, 1H), 3.3(s, 2H), 7.2(s, 1H), 7.3(d, 2H), 7.3(s, 1H), 7.4(d, 2H), 7.8(s, 1H)

Compound B-3-55
1.5(s, 3H), 2.02(s, 3H), 2.04(s, 3H), 2.07(s, 3H), 2.14(s, 3H), 2.7-2.9(m, 7H), 3.0-3.2(m, 3H), 3.8(d, 1H), 3.9(d, 1H), 7.0(m, 2H), 7.27(m, 1H), 7.3(d, 1H), 7.7(bs, 1H)

Compound B-3-145
1.4(s, 3H), 1.8(m, 2H), 2.06(s, 3H), 2.09(s, 3H), 2.10(s, 3H), 2.3-2.4(m, 4H), 2.5-2.8(m, 2H), 3.0(m, 3H), 3.5(m, 1H), 4.0(d, 1H), 4.3(dd, 1H), 6.3(d, 1H), 6.6(m, 1H), 6.9-7.0(m, 2H), 7.2-7.3(m, 5H)

[Preparation of Pharmaceutical Preparation]
Pharmaceutical preparations containing the compounds of the present invention were prepared by the following process.

| Oral agent (Tablets containing 10 mg of active ingredient) | |
|---|---|
| Compound of the present invention | 10 mg |
| Lactose | 81.4 mg |
| Cornstarch | 20 mg |

-continued

| Oral agent (Tablets containing 10 mg of active ingredient) | |
|---|---|
| Hydroxypropyl cellulose | 4 mg |
| Calcium carboxymethyl cellulose | 4 mg |
| Magnesium stearate | 0.6 mg |
| Total | 120 mg |

According to the formulation described above, 50 g of the compound of the present invention, 407 g of lactose and 100 g of cornstarch were uniformly mixed using a fluidized bed granulation coating apparatus (manufactured by Okawara Corporation). To the mixture, 200 g of an aqueous 10% hydroxypropyl cellulose solution was sprayed, followed by granulation. After drying, the resulting granules were passed through a 20-mesh sheave and 20 g of calcium carboxymethyl cellulose and 3 g of magnesium stearate were added, followed by compressing using a rotary tablet machine (manufactured by Hata Iron Works Co., Ltd.) and Uski measuring 7 mm×8.4 R to obtain tables each containing 120 mg of an active ingredient.

EXAMPLE 18

[In Vitro Lipid Peroxidation Inhibition]

An in vitro lipid peroxidation inhibition of the compounds of the present invention was evaluated by measuring a lipid peroxidation activity in a rat brain homogenate according to a process of Malvy, c., et al., Biochemical and Biophysical Research Communications, 1980, Vol. 95, p. 734-737. That is, a rat brain was extracted and a 5-fold amount of an aqueous phosphoric acid buffered saline solution (pH 7.4) (hereinafter abbreviated to PBS) was added to the brain under ice cooling, followed by homogenization using a Teflon homogenizer and further centrifugation at 10,000 g for 20 minutes to prepare a brain homogenate as a supernatant. To the brain homogenate thus prepared, 500 µM cysteine, 5 µM sulfuric acid monobasic iron and 100 mM KCl were added, followed by incubation at 37° C. for 30 minutes. Malondialdehyde produced by the composition of lipid peroxidation was measured by a thiobarbituric acid process. A 50% inhibitory concentration (hereinafter abbreviated to $IC_{50}$) of the compounds of the present invention was determined from measured values. The results are shown in Table 30. It has been found that the compounds of the present invention have an in vitro lipid peroxidation inhibition.

TABLE 30

| Compound No. | In vitro lipid peroxidation inhibition 50% inhibitory concentration ($IC_{50}$ µM) |
|---|---|
| B-1-1 | 0.40 |
| B-1-2 | 0.31 |
| B-1-18 | 0.25 |
| B-1-4 | 0.42 |
| B-2-1-1 | 0.35 |
| B-2-2-1 | 0.47 |
| B-2-5-1 | 0.42 |
| B-2-5-3 | 0.21 |
| B-2-5-82 | 0.40 |
| B-2-9-1 | 0.43 |
| B-3-1 | 0.34 |
| B-3-10 | 0.50 |
| B-3-58 | 0.54 |

TABLE 30-continued

| Compound No. | In vitro lipid peroxidation inhibition 50% inhibitory concentration ($IC_{50}$ µM) |
|---|---|
| R-1 | 0.23 |
| R-2 | 0.23 |

EXAMPLE 19

[Tissue Migration Properties]

Tissue migration properties of the compounds of the present invention were evaluated by measuring an ex vivo lipid peroxidation inhibition. A solution or suspension prepared by dissolving or suspending each of test compounds in an aqueous physiological saline solution or a 1% poly oxy ethylene hydrogenated castor oil (NIKKOL HCO-60, manufactured by Nikko Chemicals Co., Ltd.) physiological saline solution was intraperitoneally administered to SD male rats (one group: 3 rats, 6 weeks old) (available from Nippon SLC Co., Ltd.) at a dose of 100 mg/kg. 30 Minutes after administration, rats were bled to death by cutting the carotid artery and then the brain, heart and kidney were extracted. A lipid peroxidation activity of each tissue homogenate was measured by the process described in Example 18. An inhibition ratio in each tissue of the compounds of the present invention was determined from the amount of lipid peroxidation produced of a control group (physiological saline administration group) and a test compound administration group. The results are shown in Table 31. As is apparent from the results, the compounds of the present invention have excellent tissue migration properties.

TABLE 31

| Compound No. | Ex vivo lipid peroxidation inhibition inhibition ratio (%) | | |
|---|---|---|---|
| | Brain | Heart | Kidney |
| B-1-1 | 96 | 88 | 95 |
| B-1-2 | 79 | 93 | 89 |
| B-1-18 | 77 | 88 | 89 |
| B-1-4 | 94 | 88 | 90 |
| B-2-1-1 | 96 | 88 | 91 |
| B-2-2-1 | 97 | 81 | 86 |
| B-2-5-1 | 96 | 88 | 88 |
| B-2-5-3 | 95 | 83 | 91 |
| B-2-5-82 | 99 | 86 | 92 |
| B-2-9-1 | 95 | 95 | 91 |
| B-3-1 | 98 | 90 | 94 |
| B-3-10 | 97 | 94 | 90 |
| B-3-58 | 96 | 94 | 91 |
| R-1 | 68 | 59 | 75 |
| R-2 | 45 | 57 | 84 |

EXAMPLE 20

[In Vivo Antioxidative Activity]

An in vivo antioxidative activity of the compounds of the present invention was evaluated from an abnormal behavior due to administration of ferrous chloride into spinal subarachnoid cavity of mice as well as an inhibitory effect of a fatality rate according to the process described in J. Med. Chem., 1997, Vol. 40, p. 559-573. Using Slc:ICR male mice (one group: 3 to 7 mice, 5 weeks old) (available from Nippon SLC Co., Ltd.), 5 µl of a 50 mM ferrous chloride physiological saline solution was administered to the spinal canal through the space between the fifth lumbar vertebrae and the sixth lumbar vertebrae. 20 to 60 minutes after administration of ferrous chloride, symptoms were observed and a score after 60 minutes was determined from symptoms shown in Table 32. Each of test compounds was dissolved or suspended in a physiological saline solution or a 1% poly oxy ethylene hydrogenated castor oil (NIKKOL HCO-60, manufactured by Nikko Chemicals Co., Ltd.) physiological saline solution and the resulting solution or suspension was intraperitoneally or orally administered 30 minutes before administration of ferrous chloride. a 50% inhibitory dose (hereinafter abbreviated to $ID_{50}$) of the compounds of the present invention was determined from the score of a control group (physiological saline administration group) and the score of a test compound administration group. The results are shown in Table 33. As is apparent from the results, the compounds of the present invention have an in vivo antioxidation action.

TABLE 32

| Score | Symptoms |
|---|---|
| 0 | Normal |
| 1 | Mice frequently bite hypogastrium or hind part end |
| 2 | at least one of the following changes is observed |
| | (1) mice frequently bite hind part while rolling |
| | (2) hypersensitive reaction and attack reaction against external stimulation |
| | (3) tremor |
| 3 | clonic convulsion |
| 4 | tonic convulsion or hind part paralysis |
| 5 | Death |

TABLE 33

| | In vivo antioxidation action 50% inhibitory concentration ($ID_{50}$ mg/kg) | |
|---|---|---|
| Compound No. | Intraperitoneal administration | Oral administration |
| B-1-1 | 4.4 | 19 |
| B-1-2 | 27 | 13 |
| B-1-18 | 4.7 | 7.4 |
| B-1-4 | 6.2 | 13 |
| B-2-1-1 | 4.5 | 11 |
| B-2-2-1 | 12 | 13 |
| B-2-5-1 | 16 | 17 |
| B-2-5-3 | 6.2 | 19 |
| B-2-5-82 | 15 | 14 |
| B-2-9-1 | 4.1 | 7.4 |
| B-3-1 | 5.4 | 14 |
| R-1 | >30 | >30 |
| R-2 | 20 | 53 |

As a control, compounds (R-1) and (R-2) of the following formulas described in International Publication WO00/006550 were used.

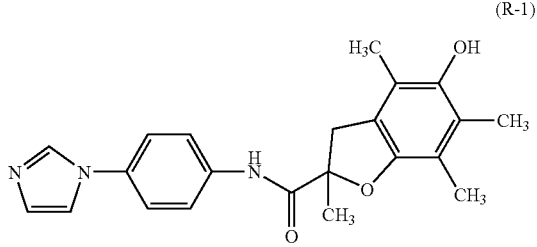
(R-1)

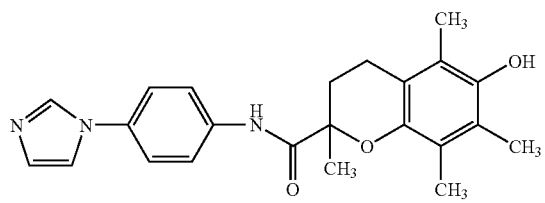
(R-2)

EXAMPLE 21

[Retina Migration Properties]

Retina migration properties of the compounds of the present invention were evaluated. To SD male rats (one group: 3 rats, 6 weeks old), a solution or suspension prepared by dissolving or suspending each of the test compounds in a 0.1N hydrochloric acid solution or a 1% poly oxy ethylene hydrogenated castor oil (NIKKOL HCO-60) solution was orally administered. After 30 minutes, both eyes were extracted and the retina was separated under ice cooling. A 5% homogenate solution of the retina was prepared in a 0.1M tris-hydrochloric acid buffer (pH 7.4) under ice cooling using a polytron homogenizer for a trace amount (NS-310E: manufactured by Nichion Irika Kiki Co., Ltd.) and, after autoxidation at 37° C. for one hour, the amount of lipid peroxidation produced was determined by a thiobarbituric acid process (MASUGI et al., vitamin 51, 21-29, 1977). A 30% inhibitory dose ($ID_{30}$) was determined from the inhibition ratio at each dose. The results are shown in Table 34. As is apparent from the results, the compounds of the present invention have an ex vivo retinal lipid peroxidation production inhibitory action and is also excellent in retina migration properties.

TABLE 34

| Compound No. | Lipid peroxidation inhibition 30% inhibitory concentration ($ID_{30}$ mg/kg, oral administration.) in ex vivo retina |
|---|---|
| B-1-2 | 5.7 |
| B-1-18 | 12 |
| B-1-4 | 6.5 |
| B-2-2-1 | 7.9 |

EXAMPLE 22

[66 kDa Protein Increase Inhibitory Action]

An action for inhibition of an increase in 66 kDa protein in the retina of rats irradiated with ultraviolet light of the compounds of the present invention was evaluated. To Wistar male rats (7 to 9 weeks old), a solution or suspension prepared by dissolving or suspending each of test compounds in a 0.1N hydrochloric acid solution or a 1% poly oxy ethylene hydrogenated castor oil (NIKKOL HCO-60) solution was orally administered. After 30 minutes, right eye was irradiated with UV-A (12 mW/cm$^2$) using a UV spot light source for 30 minutes. Left eye was not irradiated (control). During irradiation with UV-A and 2 hours before and after irradiation, rats were bred under an atmosphere where room light is screened. 48 hours after irradiation, the retina was separated. In the same manner as in Example 21, a 5% homogenate solution was prepared. Regarding a change in retinal protein, SDS-polyacrylamide electrophoresis was carried out according to the process of Lammli (Nature, 277, 680-685, 1970). Using a 4.5% gel (pH 6.8) as a concentrated gel, a 10% gel (pH 8.8) as a separated gel, the specimen was migrated in a buffer for migration (25 mM tris, 192 mM glycine 0.1% SDS) at 20 mA constant current (limit 300 V). After migration, the specimen was fixed by 15% TCA and ethanol:acetic acid: water (25:8:65) and then stained with ethanol:acetic acid: water (9:2:9) containing 0.25% Coomassie Brilliant Blue R-250. Then, the specimen was decolored with ethanol:acetic acid:water (25:8:65) and the 66 kDa protein after migration was analyzed by a densitograph. The amount of the protein in the specimen was determined by a Lowry process. The results are shown in Table 35. As is apparent from the results, the compounds of the present invention remarkably inhibit an increase in 66 kDa protein.

TABLE 35

| Compound No. (N = 3) | 66 kDa protein ratio in retina of rats irradiated with ultraviolet light (right eye: irradiated/left eye: non-irradiated) |
|---|---|
| Normal group | 1 |
| Control group | 2.51 |
| B-1-18 (10 mg/kg, p.o.) | 1.50 |

EXAMPLE 23

[5-lipoxygenase (5-LO) and 15-lipoxygenase (15-LO) Inhibitory Action]

A 5-LO inhibitory activity was measured by a partially modified process of a process of Carter et al. (Carter G. W, et al, J. Pharmacol. Exp. Ther.: 256, 929-37, 1991). That is, human peripheral blood mononuclear cells and each of test compounds dissolved in DMSO (final concentration: 1%) were preincubated (37° C., 15 minutes) in a Hanks' balanced salt solution and 30 μM A23187 was further added, followed by incubation (37° C., 30 minutes). The amount of leukotriene $B_4$ produced as a result of incubation was determined by enzyme immunoassay and a 50% production inhibitory concentration (μM) against 5-LO of each test compound was calculated. The results are shown in Table 36.

A 15-LO inhibitory activity was measured by a partially modified process of a process of Auerbach et al. (Auerbach B. J, et al., Anal. Biochem.: 201, 375-80, 1992). That is, 15-LO obtained from reticulocyte of rabbit and each of test compounds dissolved in DMSO (final concentration: 1%) were preincubated (4° C., 15 minutes) in phosphoric acid buffer (pH 7.4) and 256 μM linoleic acid was further added, followed by incubation (4° C., 10 minutes). The amount of 15-HETE produced as a result of incubation was determined by spectrophotometry ($OD_{660nm}$) and 50% production inhibitory concentration (μM) against 15-LO of each test compound was calculated. The results are shown in Table 36. Compounds (R-3) and (R-4) (edaravone) of the following formulas were used as a control drug.

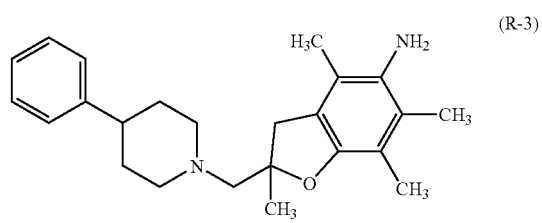
(R-3)

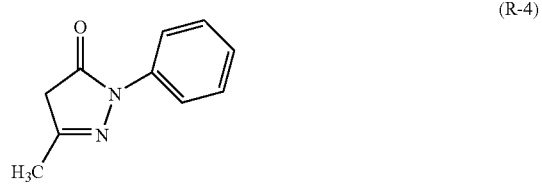
(R-4)

As is apparent from the results, the compounds of the present invention have 5-lipoxygenase (5-LO) and 15-lipoxygenase (15-LO) inhibitory action.

TABLE 36

| | Lipoxygenase inhibitory action 50% inhibitory dose ($IC_{50}$ μM) | |
|---|---|---|
| Compound No. | 5-LO | 15-LO |
| B-1-18 | 2.55 | 1.54 |
| B-1-34 | 0.162 | 5.56 |
| B-2-5-1 | 0.16 | 1.40 |
| B-3-1 | 2.80 | 1.57 |
| R-3 | >10 (34%) | 3.26 |
| R-4 | >10 (32%) | 5.57 |

EXAMPLE 24

[Acute Oral Toxicity]

A single dose of each of the compounds of the present invention was orally administered to male mice. After observing for 7 days, a mortality rate was determined. The results are shown in Table 37. The compound (R-3) was used as a control drug. As is apparent from the results, the compounds of the present invention have low acute oral toxicity.

TABLE 37

| Compound No. | Mouse acute oral toxicity ($LD_{50}$ mg/kg) |
|---|---|
| B-1-18 | >1000 |
| B-2-5-1 | >2000 |
| B-3-1 | >300 |
| R-3 | <300 |

The invention claimed is:

1. A compound represented by the formula (1):

B-D-Z (1)

[wherein B represents the following formula(B-1):

(B-1)

A represents an imidazolyl or pyrazolyl group represented by the following formula (A-1), (A-2), (A-3) or (A-4):

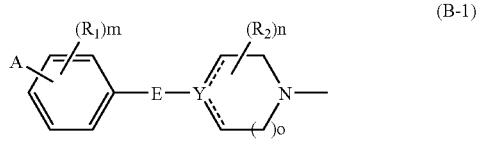

(A-1)

(A-2)

(A-3)

(A-4)

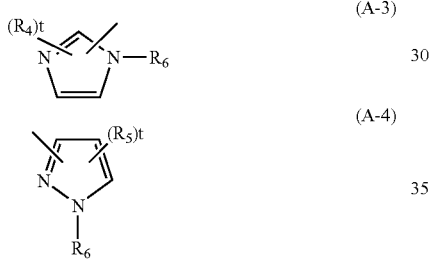

(wherein $R_4$ and $R_5$ each independently represents a $C_{1-6}$ alkyl group which may be substituted with G1, a $C_{1-6}$ alkoxy group which may be substituted with G1, a $C_{1-6}$ alkylsulfonyl group which may be substituted with G1, or a halogen atom; $R_6$ represents a hydrogen atom, a $C_{1-6}$ alkyl group which may be substituted with G1, a $C_{1-6}$ alkylcarbonyl group which may be substituted with G1, or a benzoyl group which may be substituted with G1, or a tetrahydropyranyl group;

G1 represents a cyano group, a formyl group, a hydroxyl group, a $C_{1-6}$ alkoxy group, an amino group, a monomethylainino group, a dimethylamino group or a halogen atom, s represents 0 or an integer of 1 to 3, t represents 0 or an integer of 1 or 2, and $R_4$(s) or $R_5$(s) may be the same or different when s or t is 2 or more);

$R_1$ represents a halogen atom, a nitro group, a cyano group, a hydroxyl group, a $C_{1-6}$ alkyl group which may be substituted with G2, a $C_{1-6}$ alkoxy group which may be substituted with G2, a $C_{1-6}$ alkylthio group which may be substituted with G2, a $C_{1-6}$ alkylcarbonyl group which may be substituted with G2, an amino group (which may be substituted with one or two $C_{1-6}$ alkyl groups), a benzoyl group which may be substituted with G2, or a benzyl group which may be substituted with G2;

$R_2$ represents a $C_{1-6}$ alkyl group which may be substituted with G2;

G2 represents a cyano group, a formyl group, a hydroxyl group, a $C_6$ alkoxy group, a $C_{1-6}$ alkoxycarbonyl group, a nitro group, an amino group, a monomethylamino group, a dimethylamino group or a halogen atom;

m represents 0 or an integer of 1 to 4, and $R_1$(s) may be the same or different when m is 2 or more;

n represents 0 or an integer of 1 to 8, and $R_2$(s) may be the same or different when n is 2 or more;

o represents an integer of 1;

in the formula (B-1), the dotted line represents a single bond or a double bond and does not simultaneously represent a double bond;

Y represents a carbon atom or a nitrogen atom, which may have a substituent selected from the group consisting of a hydrogen and a hydroxyl or a multiple bond that satisfies a valence;

E represents an oxygen atom, a sulfur atom or the following formula (1a) when Y represents a carbon atom;

(1a)

(wherein $R_{60}$ represents a hydrogen atom, a $C_{1-6}$ alkylcarbonyl group, or a benzoyl group (which may be substituted with a nitro group, a halogen atom, a hydroxyl group, a $C_{1-6}$ alkoxy group, or a $C_{1-6}$ alkyl group); $R_7$ and $R_8$ each independently represents a hydrogen atom, a cyano group, a hydroxyl group, a halogen atom, a $C_{1-6}$ alkyl group, a $C_{1-6}$ alkoxy group, a $C_{2-6}$ alkenyl group, a $C_{2-6}$ alkynyl group, a $C_{2-6}$ alkenyloxy group, a $C_{2-6}$ alkynyloxy group, a $C_{1-6}$ acyloxy group, a $C_{3-6}$ cycloalkyl group which may be substituted with G2, or a phenyl group which may be substituted with G2;

j and k independently represent 0 or an integer of 1;

l represents 0 or an integer of 1 to 16;

$R_7$(s) and $R_8$(s) may be the same or different when l is 2 or more);

E represents the formula (1a) when Y represents a nitrogen atom;

D represents the formula (1a);

Z represents a 2,3-dihydrobenzofuran-2-yl group which is substituted with G3, or a 2,3-dihydrobenzofuran-3-yl group which is substituted with G3;

G3 represents the formula: $NHR_{10}$

{wherein $R_{10}$ represents a hydrogen atom, a $C_{1-6}$ alkylcarbonyl group, or a benzoyl group (which may be substituted with a nitro group, a halogen atom, a hydroxyl group, a $C_{1-6}$ alkoxy group, or a $C_{1-6}$ alkyl group)};

or the formula: $OR_{11}$

{wherein $R_{11}$ represents a hydrogen atom, a $C_{1-6}$ alkylcarbonyl group, or a benzoyl group (which may be substituted with a hydroxyl group, a $C_{1-6}$ alkoxy group, a halogen atom, or a $C_{1-6}$ alkyl group)}]

or a pharmaceutically acceptable salt thereof.

2. The compound according to claim 1, wherein Z represents a group represented by the following formula (Z-2) or (Z-5):

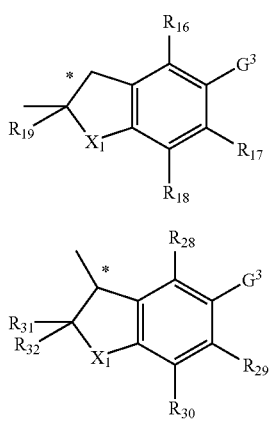

(Z-2)

(Z-5)

[wherein * represents an asymmetric carbon atom; $X_1$ represents an oxygen atom; $R_{16}$ to $R_{19}$ and $R_{28}$ to $R_{32}$ each independently represents a hydrogen atom or a $C_{1-6}$ alkyl group, and G3 represents the formula: $NHR_{10}$ {wherein $R_{10}$ represents a hydrogen atom, a $C_{1-6}$ alkylcarbonyl group, or a benzoyl group (which may be substituted with a nitro group, a halogen atom, a hydroxyl group, a $C_{1-6}$ alkoxy group, or a $C_{1-6}$ alkyl group)};

or the formula: $OR_{11}$

{wherein $R_{11}$ represents a hydrogen atom, a $C_{1-6}$ alkylcarbonyl group, or a benzoyl group (which may be substituted with a hydroxyl group, a $C_{1-6}$ alkoxy group, a halogen atom, or a $C_{1-6}$ alkyl group)}]

or a pharmaceutically acceptable salt thereof.

3. A pharmaceutical composition comprising one or more compounds or pharmaceutically acceptable salts thereof according to claim 1 or 2 and an excipient.

\* \* \* \* \*

UNITED STATES PATENT AND TRADEMARK OFFICE
CERTIFICATE OF CORRECTION

PATENT NO. : 7,553,837 B2
APPLICATION NO. : 10/566820
DATED : June 30, 2009
INVENTOR(S) : Nobuhiro Umeda et al.

It is certified that error appears in the above-identified patent and that said Letters Patent is hereby corrected as shown below:

On cover page, item (75) Inventors,

Please delete "Hiroko Momoe" and insert -- Hiroko Moroe --.

Signed and Sealed this

Twenty-ninth Day of September, 2009

David J. Kappos
*Director of the United States Patent and Trademark Office*